United States Patent
Pauls et al.

(10) Patent No.: US 8,680,282 B2
(45) Date of Patent: Mar. 25, 2014

(54) CYCLIC INHIBITORS OF CARNITINE PALMITOYLTRANSFERASE AND TREATING CANCER

(75) Inventors: Heinz W. Pauls, Oakville (CA); Bryan T. Forrest, Toronto (CA); Peter Brent Sampson, Oakville (CA); Yong Liu, North York (CA); Radoslaw Laufer, Oakville (CA); Yunhui Lang, Markham (CA); Miklos Feher, Toronto (CA); Yi Yao, Mississauga (CA); Guohua Pan, Oakville (CA)

(73) Assignee: University Health Network, Toronto (CA)

( * ) Notice: Subject to any disclaimer, the term of this patent is extended or adjusted under 35 U.S.C. 154(b) by 640 days.

(21) Appl. No.: 12/671,154

(22) PCT Filed: Aug. 1, 2008

(86) PCT No.: PCT/CA2008/001415
§ 371 (c)(1),
(2), (4) Date: Sep. 30, 2010

(87) PCT Pub. No.: WO2009/015485
PCT Pub. Date: Feb. 5, 2009

(65) Prior Publication Data
US 2011/0015174 A1 Jan. 20, 2011

Related U.S. Application Data

(60) Provisional application No. 60/962,826, filed on Aug. 1, 2007.

(51) Int. Cl.
*C07D 211/58* (2006.01)
*A61K 31/4468* (2006.01)

(52) U.S. Cl.
USPC .............................. 546/223; 546/224; 514/329

(58) Field of Classification Search
USPC .................................. 546/223, 224; 514/329
See application file for complete search history.

(56) References Cited

U.S. PATENT DOCUMENTS

| | | | |
|---|---|---|---|
| 4,673,763 A | 6/1987 | Buckler et al. | |
| 4,767,781 A | 8/1988 | Shinagawa et al. | 514/513 |
| 5,593,967 A | 1/1997 | Horwell et al. | |
| 5,847,125 A | 12/1998 | McDonald et al. | |
| 6,369,073 B1 | 4/2002 | Giannessi | |
| 6,495,565 B2 * | 12/2002 | Duan et al. | 514/314 |
| 6,528,684 B1 | 3/2003 | Giannessi | |
| 6,656,936 B1 | 12/2003 | Savle et al. | |
| 6,822,115 B2 | 11/2004 | Giannessi | |
| 2002/0187534 A1 | 12/2002 | Pizer | |
| 2003/0125315 A1 | 7/2003 | Mjalli | |
| 2004/0072802 A1 | 4/2004 | Duan et al. | |
| 2005/0059705 A1 | 3/2005 | Mjalli | |
| 2006/0058287 A1 | 3/2006 | Axten | |
| 2010/0105900 A1 | 4/2010 | Pauls | |

FOREIGN PATENT DOCUMENTS

| | | |
|---|---|---|
| CA | 2192088 | 2/1996 |
| CA | 2373360 | 11/2000 |
| CA | 2366800 | 4/2003 |
| CA | 2572208 | 5/2006 |
| CN | 1919865 | 2/2007 |
| DE | 2217169 | 10/1973 |
| EP | 0127098 | 12/1984 |
| EP | 1203766 | 5/2002 |
| EP | 1484313 | 12/2004 |
| EP | 1806342 | 7/2007 |
| WO | WO 99/65881 | 6/1999 |
| WO | WO 99/42435 | 8/1999 |
| WO | WO 99/59957 | 11/1999 |
| WO | WO 01/96310 | 12/2001 |
| WO | WO 03/010129 | 2/2003 |
| WO | WO 2004/063143 | 7/2004 |
| WO | WO 2005/077354 | 8/2005 |
| WO | WO 2005/105802 | 11/2005 |
| WO | WO 2006/002474 | 1/2006 |
| WO | WO 2006/092204 | 9/2006 |
| WO | WO 2008/015081 | 2/2008 |

OTHER PUBLICATIONS

"Scientific Discussion of Angiox." EMEA 2005 online: "http://www.ema.europa.eu/docs/en_GB/document_library/EPAR_Scientific_Discussion/human/000562/WC500025072.pdf" available Sep. 28, 2004.*

Online "https://www.google.com/search?q=Bivalirudin+ Trifluoroacetate&hl=en&rls=com.microsoft%3Aen-us%3AIESearchBox&sa=X&ei=ywLJUM_XOZLE0AGjgYGYCw&ved=0CB0QpwUoBg&source=lnt&tbs=cdr%3A1%2Ccd_min%3A%2Ccd_max%3A2007&tbm=" accessed Dec. 12, 2012.*

(Continued)

*Primary Examiner* — David K O Dell
(74) *Attorney, Agent, or Firm* — McCarter & English, LLP; Steven G. Davis; Wei Song

(57) ABSTRACT

A CPT1 inhibitor compound is represented by Structural Formula (I) or a pharmaceutically acceptable salt thereof: or a pharmaceutically acceptable salt thereof. A pharmaceutical composition comprises a compound represented by Structural Formula (I) or a pharmaceutically acceptable salt thereof. A method of treating a subject having cancer comprises administering to the subject a therapeutically effective amount of a compound represented by Structural Formula (I) or a pharmaceutically acceptable salt thereof.

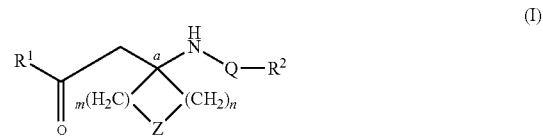

11 Claims, No Drawings

(56) References Cited

OTHER PUBLICATIONS

International Search Report and Written Opinion for Application No. PCT/CA2008/000440, dated Jun. 23, 2008.
International Preliminary Report on Patentability for Application No. PCT/CA2008/000440, dated Sep. 15, 2009.
International Preliminary Report on Patentability for Application No. PCT/CA2008/001415, dated Feb. 2, 2010.
Chemical Abstracts Registry No. 886148-32-9 (AKos Consulting and Solutions GMBH) Feb. 7, 2006.
Giannessi, et al., "Reversible Carnitine Palmitoyltransferase Inhibitors with Broad Chemical Diversity as Potential Antidiabetic Agents", J. Med. Chem., 2001, vol. 44, pp. 2383-2386.
Giannessi, et al., "Discovery of a Long-Chain Carbamoyl Aminocarnitine Derivative, a Reversible Carnitine Palmitoyltransferase Inhibitor with Antiketotic and Antidiabetic Activity", J. Med. Chem., 2003, vol. 46, pp. 303-309.
Synthesis of novel, achiral, and reversible inhibitors of carnitine palmitoyltransferase I. Brinkman, John A. et al., Sandoz Research Institute, Sandoz Pharmaceutical Corporation, East Hanover, NJ, ESA. Book of Abstracts, 213th ACS National Meeting, San Francisco, Apr. 13-17, 1997, ORGN-565. Publisher: American Chemical Society, Washington DC CODEN: 64AOAA Conference; Meeting Abstract written in English. AN 1997:162827 CAPLUS (Copyright © 2008 ACS on SciFinder®).
Zhang, et al., "Total synthesis and reassignment of stereochemistry of obyanamide", Tetrahedron, 2006, vol. 62, pp. 9966-9972.
Zhang, et al., "Synthesis of Obyanamide, a Marine Cytotoxic Cyclic Depsipepetide", Chinese Chemical Letters, 2006, vol. 17, pp. 285-288.
PCT International Search Report and Written Opinion—(PCT/CA2008/001415) Date of Mailing Nov. 18, 2008.
Gilmore, et al., "Synthesis and structure-activity relationship of a novel, achiral series of TNF-alpha converting enzyme inhibitors", Bioorganic & Medicinal Chemistry Letters, 2006, vol. 16, pp. 2699-2704.
STN International, File CAPLUS, CAPLUS accession No. 2004:310829, Document No. 140:303552, Duan, et al., "Preparation of beta-amino acid derivatives as inhibitors of matrix metalloproteases and TNF-alpha", English Abstract.
STN International, File CAPLUS, CAPLUS accession No. 1989:22986, Document No. 110:22986, Dobrev, et al., "The influence of steric factors on the dehydration of 3-benzoylaminopropionic acids by acetic anhydride"; Comptes Rendus de l'Academie des Sciences, 1988, English Abstract.
STN International, File CAPLUS, CAPLUS accession No. 1974 :94833, Document No. 80:94833, Arnaudov, et al., "Infrared-spectroscopic study of hydrogen bodning in 3-(acylamino)propanoic acids", Godishnik na Sofiiskiya Universitet Sv. Kliment Okhridski, Khimicheski Fakultet, 1973, English Abstract.

* cited by examiner

CYCLIC INHIBITORS OF CARNITINE PALMITOYLTRANSFERASE AND TREATING CANCER

RELATED APPLICATIONS

This application is the U.S. National Stage of International Application No. PCT/CA2008/001415, filed Aug. 1, 2008, which claims the priority benefit of U.S. Provisional application No. 60/962,826, filed Aug. 1, 2007. The entire contents of the above applications are incorporated herein by reference.

BACKGROUND OF THE INVENTION

Fatty acids are catabolized, mostly, in the mitochondria through the β-oxidation pathway, where the carnitine palmitoyltransferase (CPT) system plays a key role in transporting long chain fatty acids (FAs) from the cytoplasm to the mitochondrial matrix. The CPT enzymatic system includes the members CPT1A and CPT1B, which are localized in the outer mitochondrial membrane, and CPT2, localized to the inner mitochondrial membrane. While CPT2 seems to be found in the mitochondrial membranes, regardless of the location of the organelle, the CPT1 isoforms have been found to vary with tissue. CPT1A occurs in the liver and CPT1B has been found in muscle. A new protein having sequence homology with CPT1 has been recently identified and given then name CPT1C.

Applicants described in a co-pending U.S. Provisional Application No. 60/893,649, filed on Mar. 8, 2007 (the entire teachings of which are incorporated herein by reference), that CPT1C is a determinant of cell growth and survival, in particular under hypoxic conditions, such as in a tumor in which the cells are rapidly dividing to the point where hypoxic conditions develop locally in the patient tissue: (a) CPT1C has been found to be up-regulated transcriptionally by p53 in vitro and in vivo; (b) depletion of CPT1C in mouse embryonic (ES) stem cells using a gene-trap was found to result in a decrease of cell proliferation, a smaller cell size and a spontaneous activation of the intrinsic mitochondrial apoptosis pathway evidenced by reduced mitochondrial membrane potential and increased caspase activation; (c) CPT1C-deficient mouse ES cells were more sensitive to glucose deprivation or hypoxia, a condition widely observed in tumors; (d) examination by electron microscopy showed swelling of the mitochondria of the CPT1C-depleted ES cells and lipid droplets in the cell, neither being present in the ES cells heterozygous for CPT1C; (e) CPT1C expression was shown to increase in human breast, lung and colon cancer cells lines subjected to hypoxic conditions; (f) CPT1C mRNA levels were measured in paired tumor and matched normal tissues and found to be increased in 15 out of 19 of the lung tumor tissues examined; and (g) growth of human cancer cells in which CPT1C expression was knocked down by small interference RNA was inhibited and further reduced under hypoxic conditions.

In addition, Applicants described in a co-pending U.S. Provisional Application No. 60/893,999, filed on Mar. 27, 2007 (the entire teachings of which are incorporated herein by reference), that CPT1A expression is increased in a large portion of lung tumor tissues compared to normal lung tissues, and that molecular depletion or pharmacological inhibition of CPT1A leads to cell death and growth inhibition of cancer cells.

Therefore, agents which inhibit CPT1, in particular, CPT1A and/or CPT1C, have the potential to treat conditions associated with altered fatty acid metabolism. There is a need for additional agents which can act as glucosylceramide synthase inhibitors.

SUMMARY OF THE INVENTION

It has now been discovered that compounds represented by Structural Formula (I) and pharmaceutically acceptable salts thereof can effectively inhibit CPT, in particular CPT1A. As such, these CPT inhibitors can be used for treating cancer. In addition, these compounds can be used for treating diabetes. Based upon this discovery, novel CPT inhibitors, pharmaceutical compositions comprising CPT inhibitors, and methods of treatment using CPT inhibitors are disclosed herein.

The CPT inhibitors disclosed herein are represented by Structural Formula (I), or a pharmaceutically acceptable salt thereof:

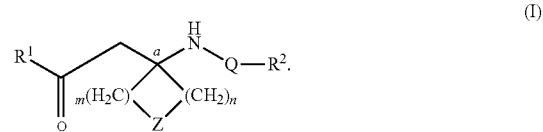

(I)

$R^1$ is —OH or —OC$_{1-6}$ alkyl.

Z is —N($R^4$)—, —N$^+$($R^4R^5$)X$^-$— or —C($R^4R^5$)—.

Q is —C(=O)—, —C(=S)—, —C(O)NH—, —C(S)NH—, —S(O)—, —S(O)$_2$—, —S(O)NH—, —S(O)$_2$—NH—, —C(=NH)—, —C(=NH)—N($R^3$)—, —C(O)N($R^3$)—, —C(S)N($R^3$)—, —S(O)—N($R^3$)— or —S(O)$_2$—N($R^3$)—.

$R^2$ and $R^3$ are each independently a substituted or unsubstituted aliphatic group, a substituted or unsubstituted aryl group, or a substituted or unsubstituted heteroaryl group, or $R^2$ and $R^3$ taken together with the nitrogen atom of N($R^2R^3$) form a substituted or unsubstituted non-aromatic heterocyclic ring.

Each of $R^4$ and $R^5$ independently is —H or C$_{1-6}$ alkyl.

X$^-$ is a pharmaceutically acceptable counter ion.

Each of n and m independently is 1, 2 or 3.

In one embodiment, the present invention is directed to a compound represented by Structural Formula (I), or a pharmaceutically acceptable salt thereof, wherein values for the variables of Structural Formula (I) are as described above, provided that when Q is —C(=O)—, —C(=S)—, —C(O)NH—, —C(S)NH— or —S(O)$_2$—, and each of n and m is 2, then $R^2$ is not a C3-C7 alkyl group substituted with a substituted phenoxy group, and when Q is —C(=O)— and $R^2$ is a substituted or unsubstituted phenyl, and when one of n and m is 1 and the other of n and m is 1 or 2 (or only 2), or each of n and m is 2, then Z is —N$^+$($R^4R^5$)X$^-$—.

In another embodiment, the present invention is directed to a pharmaceutical composition comprising a pharmaceutically acceptable carrier and a compound represented by Structural Formula (I) or a pharmaceutically acceptable salt thereof. Values for the variables of Structural Formula (I) are as described above, provided that when Q is —C(=O)—, —C(=S)—, —C(O)NH—, —C(S)NH— or —S(O)$_2$—, and each of n and m is 2, then $R^2$ is not a C3-C7 alkyl group substituted with a substituted phenoxy group, and when Q is —C(=O)— and $R^2$ is a substituted or unsubstituted phenyl, and when one of n and m is 1 and the other of n and m is 2, or each of n and m is 2, then Z is —N$^+$($R^4R^5$)X$^-$—.

In yet another embodiment, the present invention is directed to a method of treating a subject having cancer, comprising administering to the subject a therapeutically effective amount of a compound represented by Structural Formula (I) or a pharmaceutically acceptable salt thereof. Values for the variables of Structural Formula (I) are as described above. The cancer is selected from the group consisting of lung cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma.

In yet another embodiment, the present invention is directed to a method of treating a subject having cancer, comprising administering to the subject a therapeutically effective amount of a compound represented by Structural Formula (I) or a pharmaceutically acceptable salt thereof. Values for the variables of Structural Formula (I) are as described above, provided that when Q is —C(=O)— and $R^2$ is a substituted or unsubstituted phenyl, and when one of n and m is 1 and the other of n and m is 2, or each of n and m is 2, then Z is —$N^+(R^4R^5)X^-$—.

The present invention also includes a method of treating a subject with a condition or disease selected from the group consisting of diabetes; a condition or disease mediated by metalloproteases, tumor necrosis factor, aggrecanase or a combination thereof; and a condition or disease mediated by Cholecystokinins. The method comprises administering to the subject a therapeutically effective amount of a compound represented by Structural Formula (I) or a pharmaceutically acceptable salt thereof. Values for the variables of Structural Formula (I) are as described above, provided that when Q is —C(=O)—, —C(=S)—, —C(O)NH—, —C(S)NH— or —$S(O)_2$—, and each of n and m is 2, then $R^2$ is not a C3-C7 alkyl group substituted with a substituted phenoxy group, and when Q is —C(=O)— and $R^2$ is a substituted or unsubstituted phenyl, and when one of n and m is 1 and the other of n and m is 2, or each of n and m is 2, then Z is —$N^+(R^4R^5)X^-$—.

Also, included in the present invention is the use of a compound represented by Structural Formula (I) or a pharmaceutically acceptable salt thereof for the manufacture of a medicament for treating a subject having cancer selected from the group consisting of lung cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma, wherein values for the variables of Structural Formula (I) are as described above.

Also, included in the present invention is the use of a compound represented by Structural Formula (I) or a pharmaceutically acceptable salt thereof for the manufacture of a medicament. In one embodiment, the medicament is for treating a subject having cancer, wherein values for the variables of Structural Formula (I) are as described above, provided that when Q is —C(=O)— and $R^2$ is a substituted or unsubstituted phenyl, and when one of n and m is 1 and the other of n and m is 2, or each of n and m is 2, then Z is —$N^+(R^4R^5)X^-$—. In another embodiment, the medicament is for treating a subject with a condition or disease selected from the group consisting of diabetes; a condition or disease mediated by metalloproteases, tumor necrosis factor, aggrecanase or a combination thereof and a condition or disease mediated by Cholecystokinins, wherein values for the variables of Structural Formula (I) are as described above, provided that when Q is —C(=O)—, —C(=S)—, —C(O)NH—, —C(S)NH— or —$S(O)_2$—, and each of n and m is 2, then $R^2$ is not a C3-C7 alkyl group substituted with a substituted phenoxy group, and when Q is —C(=O)— and $R^2$ is a substituted or unsubstituted phenyl, and when one of n and m is 1 and the other of n and m is 2, or each of n and m is 2, then Z is —$N^+(R^4R^5)X^-$—.

Also, included in the present invention is the use of a compound represented by Structural Formula (I) or a pharmaceutically acceptable salt thereof for therapy, such as treating cancer, diabetes, a condition or disease mediated by metalloproteases, tumor necrosis factor, aggrecanase or a combination thereof, or a condition or disease mediated by Cholecystokinins. Values for the variables of Structural Formula (I) are as described above, provided that when Q is —C(=O)—, —C(=S)—, —C(O)NH—, —C(S)NH— or —$S(O)_2$—, and each of n and m is 2, then $R^2$ is not a C3-C7 alkyl group substituted with a substituted phenoxy group, and when Q is —C(=O)— and $R^2$ is a substituted or unsubstituted phenyl, and when one of n and m is 1 and the other of n and m is 2, or each of n and m is 2, then Z is —$N^+(R^4R^5)X^-$—.

Also, included in the present invention is the use of a compound represented by Structural Formula (I) or a pharmaceutically acceptable salt thereof for treating a subject having cancer selected from the group consisting of lung cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma, wherein values for the variables of Structural Formula (I) are as described above.

Also, included in the present invention is the use of a compound represented by Structural Formula (I) or a pharmaceutically acceptable salt thereof for treating a subject having cancer, wherein values for the variables of Structural Formula (I) are as described above, provided that wherein when Q is —C(=O)— and $R^2$ is a substituted or unsubstituted phenyl, and when one of n and m is 1 and the other of n and m is 2, or each of n and m is 2, then Z is —$N^+(R^4R^5)X^-$—.

Also, included in the present invention is the use of a compound represented by Structural Formula (I) or a pharmaceutically acceptable salt thereof for treating a subject having diabetes, a condition or disease mediated by metalloproteases, tumor necrosis factor, aggrecanase or a combination thereof, or a condition or disease mediated by Cholecystokinins. Values for the variables of Structural Formula (I) are as described above, provided that when Q is —C(=O)—, —C(=S)—, —C(O)NH—, —C(S)NH— or —$S(O)_2$—, and each of n and m is 2, then $R^2$ is not a C3-C7 alkyl group substituted with a substituted phenoxy group, and when Q is —C(=O)— and $R^2$ is a substituted or unsubstituted phenyl, and when one of n and m is 1 and the other of n and m is 2, or each of n and m is 2, then Z is —$N^+(R^4R^5)X^-$—.

The compounds of the invention are inhibitors of CPT1, in particular CPT1A and/or CPT1C. As such, they can be used for treating various disorders associated with fatty acid metabolism, including cancer and diabetes.

DETAILED DESCRIPTION OF THE INVENTION

In one aspect, the invention is directed to a compound represented by Structural Formula (I), or a pharmaceutically acceptable salt thereof. A first set of values and preferred values for the variables in Structural Formula (I) are provided in the following paragraphs.

Z is —$N(R^4)$—, —$N^+(R^4R^5)X^-$—, or —$C(R^4R^5)$—. Preferably, Z is —$N(R^4)$— or —$N^+(R^4R^5)X^-$—. More preferably, Z is —$N^+(R^4R^5)X^-$—.

$X^-$ is a pharmaceutically acceptable counter ion. Suitable pharmaceutically acceptable counter ions include acetate, trifluoroacetate, benzenesulfonate, benzoate, citrate, ethanesulfonate, fumarate, gluconate, glycolate, lactate, methanesulfonate, p-toluenesulfonate, tartrate, chloride, bromide, iodide, perchlorate and the like.

n and m are each independently 1, 2 or 3. Preferably, each of n and m is 1 or 2, and the sum of n and m is 3 or 4. In some preferred embodiments, the sum of n and m is 3 or 4 (e.g., 4) and Z is —N$^+$(R$^4$R$^5$)X$^-$—.

Q is —C(=O)—, —C(=S)NH—, —S(O)—, —S(O)$_2$—, —S(O)NH—, —S(O)$_2$NH—, —C(=NH)—, —C(=NH)—N(R$^3$)—, —C(O)N(R$^3$)—, —C(S)N(R$^3$)—, —S(O)—N(R$^3$)— or —S(O)$_2$—N(R$^3$)—. In some preferred embodiments, Q is —C(O)NH—, —S(O)$_2$—, —C(=O)—, or —S(O)$_2$—NH— (e.g., —C(O)NH— or —S(O)$_2$—).

R$^1$ is —OH or —OC$_{1-6}$ alkyl. Preferably, R$^1$ is —OH, —OCH$_3$ or —OC$_2$H$_5$. In some preferred embodiments, R$^1$ is —OH or —O$^-$ (e.g., when Z is —N$^+$(R$^4$R$^5$)X$^-$—.

Each R$^2$ independently is a substituted or unsubstituted aliphatic group, a substituted or unsubstituted aryl group, or a substituted or unsubstituted heteroaryl group. Preferably, R$^2$ is an aryl or a heteroaryl group optionally substituted with one or more substituents, or an aliphatic group optionally substituted with one or more substituents. More preferably, R$^2$ is a C1-C20 aliphatic group optionally substituted with one or more substituents, a monocyclic aryl group optionally substituted with one or more substituents, or a monocyclic heteroaryl group optionally substituted with one or more substituents. Even more preferably, R$^2$ is a C1-C20 alkyl group optionally substituted with one or more substituents, a monocyclic aryl group optionally substituted with one or more substituents, or a monocyclic heteroaryl group optionally substituted with one or more substituents. Yet, even more preferably, R$^2$ is a C1-C15 alkyl group optionally substituted with one or more substituents, a monocyclic aryl group optionally substituted with one or more substituents, or a monocyclic heteroaryl group optionally substituted with one or more substituents.

Specific values of the aryl and heteroaryl groups represented by R$^2$ include:

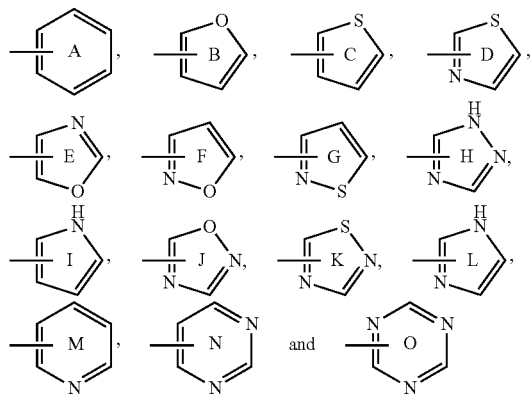

wherein each of rings A-O is optionally and independently substituted with one or more substituents. Alternatively, specific values of the aryl and heteroaryl groups represented by R$^2$ include:

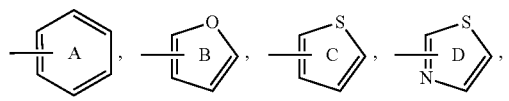

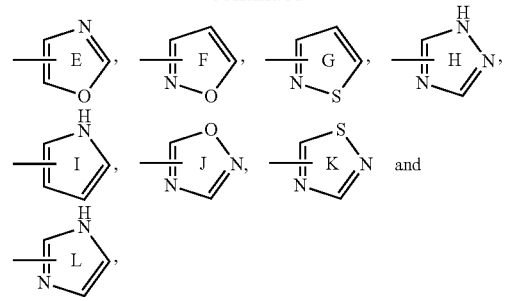

wherein each of rings A-L is optionally and independently substituted with one or more substituents. Typically, the aryl or the heteroaryl group represented by R$^2$ is selected from:

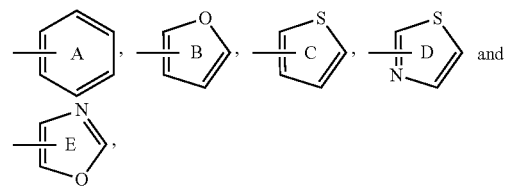

wherein each rings A-E is optionally and independently substituted with one or more substituents. More typically, the aryl or the heteroaryl group represented by R$^2$ is selected from:

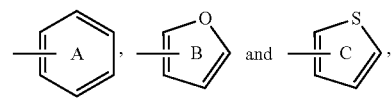

wherein each rings A-C is optionally and independently substituted with one or more substituents. In some embodiments R$^2$ is monosubstituted, e.g., with C$_1$-C$_{10}$ alkyl), —O(C$_1$-C$_{10}$ alkyl), or —(C$_1$-C$_{10}$)-Ph (e.g., phenethyl). In some embodiments, Q is —C(O)NH—, —S(O)$_2$—, —C(=O)—, or —S(O)$_2$—NH— (e.g., —C(O)NH— or —S(O)$_2$—).

A common value for R$^2$ is

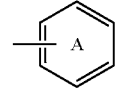

wherein ring A is optionally substituted with one or more substituents. In some preferred embodiments, A is substituted with at least one substitutents, for example, A is substituted on the para position. In some embodiments R$^2$ is monosubstituted, e.g., with C$_1$-C$_{10}$ alkyl), —O(C$_1$-C$_{10}$ alkyl), or —(C$_1$-C$_{10}$)-Ph (e.g., phenethyl). In some embodiments, Q is —C(O)NH—, —S(O)$_2$—, —C(=O)—, or —S(O)$_2$—NH— (e.g., —C(O)NH— or —S(O)$_2$—).

Suitable substituents for the aliphatic group represented by R$^2$ include halogen, Ar$^1$, —NO$_2$, —CN, —NCS, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —S(O)R$^{12}$, —S(O)$_2$R$^{12}$, —SO$_3$R$^{12}$, —SO$_2$N(R$^{11}$)$_2$, —SO$_2$N(R$^{11}$)—NR$^{11}$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$, and —NR$^{11}$SO$_2$R$^{12}$. Preferred substituents for the aliphatic group represented by $R^2$ include $Ar^1$, —$NO_2$, —CN, —$OR^{10}$, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO_2R^{12}$. Alternatively, preferred substituents for the aliphatic group represented by $R^2$ include $Ar^1$, —$NO_2$, —CN, —OH, —OAk, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO_2R^{12}$, wherein Ak is C1-C10 aliphatic group optionally substituted with halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy; or ii) an optionally substituted monocyclic aryl or heteroaryl group. More preferred substituents for the aliphatic group represented by $R^2$ include halogen, $Ar^1$, —$OR^{10}$ and —$SR^{10}$. Alternatively, more preferred substitutents for the aliphatic group represented by $R^2$ include halogen, $Ar^1$, —OH, —OAk and —$SR^{10}$. Specific examples of substituents for the aliphatic group represented by $R^2$ include halogen, C1-C3 haloalkyl, —O—$CH_2$—($C_{1-3}$ haloalkyl), Ph, —O-Ph, —S—$CH_2$—($C_{1-3}$ haloalkyl), and —S-Ph, wherein each of the Ph (i.e., phenyl) group is optionally substituted with one or more substituents selected from the group consisting of halogen, C1-C7 alkyl (e.g., C3-C7 alkyl), C1-C7 alkoxy (e.g., —$OC_5H_{11}$ or —$OC_6H_{13}$) and C1-3 haloalkyl (e.g., —$CF_3$).

Suitable substituents for the aryl or the heteroaryl group represented by $R^2$, including A-O, include halogen, $Ak^1$, $Ar^1$, —$NO_2$, —CN, —NCS, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$S(O)R^{12}$, —$S(O)_2R^{12}$, —$SO_3R^{12}$, —$SO_2N(R^{11})_2$, —$SO_2N(R^{11})$—$NR^{11}$, —$OR^{10}$, —$SR^{10}$, —$N(R^{11})_2$, —$NR^{11}C(O)R^{10}$, —$NR^{11}S(O)R^{12}$, —$NR^{11}C(O)OR^{12}$, —$N(R^{11})C(O)N(R^{11})_2$, —$NR^{11}SO_2N(R^{11})_2$, —$NR^{11}SO_2R^{12}$, —O—$[CH_2]_p$—O—, —S—$[CH_2]_p$—S— and —$[CH_2]_q$—. Preferably, substituents for the aryl or the heteroaryl group represented by $R^2$, including rings A-O, include $Ak^1$, —$NO_2$, —CN, —$OR^{10}$, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO_2R^{12}$. More preferably, substituents for the aryl or the heteroaryl group represented by $R^2$, including rings A-O, include halogen, $Ak^1$, —$OR^{10}$ and —$SR^{10}$. Even more preferably, substituents for the aryl or the heteroaryl group represented by $R^2$, including rings A-O, include halogen, $C_{1-15}$ alkyl, $C_{1-15}$ haloalkyl, —$C_{2-6}$ alkynylene-($C_{1-10}$ alkyl), —$C_{2-6}$ alkynylene-$Ar^2$, —$C_{1-6}$ alkylene-$Ar^2$, —$C_{1-6}$ alkylene-N($R^{21})_2$, —$C_{1-6}$ alkylene-O—$Ar^2$, —$C_{1-6}$ alkylene-O-$Ak^2$-$Ar^2$, —$C_{1-6}$ alkylene-S—$Ar^2$, —$C_{1-6}$ alkylene-S-$Ak^2$-$Ar^2$, —$OC_{1-10}$ alkyl, —O—$C_{1-6}$ alkylene-$Ar^0$, —$SC_{1-10}$ alkyl and —S—$C_{1-6}$ alkylene-$Ar^0$. Specific examples of substituents for the aryl or the heteroaryl group represented by $R^2$, including rings A-O, include halogen; C1-C10 alkyl (e.g., methyl, ethyl, propyl, butyl and pentyl; other examples include hexyl, heptyl, octyl, nonyl, or decanyl); C1-C3 haloalkyl; —O(C1-C10 alkyl); —O—$CH_2$—$CF_3$; phenyl; —O-Ph; —O-naphthyl; —O—($CH_2$)-Ph; —($CH_2)_2$-Ph;

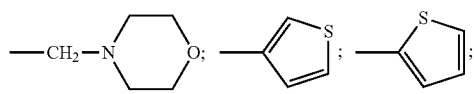

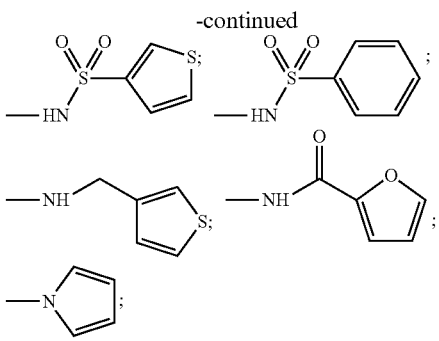

—(C≡C)-Ph; —(C≡C)—C1-C5 alkyl, —$CH_2$—O-Ph; —$CH_2$—S-Ph; —$CH_2$—O—$CH_2$-Ph; —$CH_2$—S—$CH_2$-Ph; and —NH(C=O)—$CH_3$, wherein each of the Ph (i.e., phenyl), naphthyl, thionyl, pyrrolyl and furanyl group is optionally substituted with one or more substituents selected from the group consisting of halogen, C1-C5 alkyl, methoxy, ethoxy and —$CF_3$.

In some preferred embodiments $R^2$ is a substituted aryl, e.g., phenyl. In some embodiments $R^2$ is monosubstituted, e.g., with $C_1$-$C_{10}$ alkyl), —O($C_1$-$C_{10}$ alkyl), or —($C_1$-$C_{10}$)-Ph (e.g., phenethyl). In some embodiments, Q is —C(O)NH—, —$S(O)_2$—, —C(=O)—, or —$S(O)_2$—NH— (e.g., —C(O)NH— or —$S(O)_2$—).

In some preferred embodiments $R^2$ is a substituted furanyl. In some embodiments $R^2$ is monosubstituted, e.g., with $C_1$-$C_{10}$ alkyl), —O($C_1$-$C_{10}$ alkyl), or —($C_1$-$C_{10}$)-Ph (e.g., phenethyl). In some embodiments, Q is —C(O)NH—, —$S(O)_2$—, —C(=O)—, or —$S(O)_2$—NH— (e.g., —C(O)NH— or —$S(O)_2$—).

Each $R^3$ independently is a substituted or unsubstituted aliphatic group, a substituted or unsubstituted aryl group, or a substituted or unsubstituted heteroaryl group. Preferred values of the aryl and heteroaryl groups represented by $R^3$ are as described above for the aryl and heteroaryl groups represented by $R^2$. Preferably, $R^3$ is an optionally substituted aliphatic group. More preferably, $R^3$ is an optionally substituted C1-C20 aliphatic group. More preferably, $R^3$ is an optionally substituted C1-C20 alkyl group. Even more preferably, $R^3$ is an unsubstituted C1-C10 alkyl group, such as methyl, ethyl, propyl, butyl and pentyl.

Suitable substituents for the aliphatic group represented by $R^3$ include halogen, $Ar^3$, —$NO_2$, —CN, —NCS, —$C(O)OR^{30}$, —$C(O)R^{30}$, —$C(S)R^{30}$, —$OC(O)R^{30}$, —$C(O)N(R^{31})_2$, —$C(S)N(R^{31})_2$, —$S(O)R^{32}$, —$S(O)_2R^{32}$, —$SO_3R^{32}$, —$SO_2N(R^{31})_2$, —$SO_2N(R^{31})$—$NR^{31}$, —$OR^{30}$, —$SR^{30}$, —$N(R^{31})_2$, —$NR^{31}C(O)R^{30}$, —$NR^{31}S(O)R^{32}$, —$NR^{31}C(O)OR^{32}$, —$N(R^{31})C(O)N(R^{31})_2$, —$NR^{31}SO_2N(R^{31})_2$, and —$NR^{31}SO_2R^{32}$. Preferably, substituents for the aliphatic group represented by $R^3$ include $Ar^3$, —$NO_2$, —CN, —$OR^{30}$, —$SR^{30}$, —$C(O)OR^{30}$, —$C(O)R^{30}$, —$C(S)R^{30}$, —$OC(O)R^{30}$, —$C(O)N(R^{31})_2$, —$C(S)N(R^{31})_2$, —$N(R^{31})_2$, —$NR^{31}C(O)R^{30}$, —$NR^{31}C(O)OR^{32}$, —$N(R^{31})C(O)N(R^{31})_2$ and —$NR^{31}SO^2R^{32}$. More preferably, substituents for the aliphatic group represented by $R^3$ include halogen, $Ar^1$, —$OR^{10}$ and —$SR^{10}$. Specific examples of substituents for the aliphatic group represented by $R^3$ include halogen, C1-C3 haloalkyl, —O—$CH_2$—($C_{1-3}$ haloalkyl), Ph; —O-Ph, —S—$CH_2$—($C_{1-3}$ haloalkyl), and —S-Ph, wherein each of the Ph (i.e., phenyl) group is optionally substituted with one or more substituents selected from the group consisting of halogen, C1-C7 alkyl (e.g., C3-C7 alkyl), C1-C7 alkoxy (e.g., —$OC_5H_{11}$ or —$OC_6H_{13}$), C1-3 haloalkyl (e.g., —$CF_3$).

Suitable substituents for the aryl or the heteroaryl group represented by $R^3$ include halogen, $Ak^3$, $Ar^3$, $-NO_2$, $-CN$, $-NCS$, $-C(O)OR^{30}$, $-C(O)R^{30}$, $-C(S)R^{30}$, $-OC(O)R^{30}$, $-C(O)N(R^{31})_2$, $-C(S)N(R^{31})_2$, $-S(O)R^{32}$, $-S(O)_2R^{32}$, $-SO_3R^{32}$, $-SO_2N(R^{31})_2$, $-SO_2N(R^{31})-NR^{31}$, $-OR^{30}$, $-SR^{30}$, $-N(R^{31})_2$, $-NR^{31}C(O)R^{30}$, $-NR^{31}S(O)R^{32}$, $-NR^{31}C(O)OR^{32}$, $-N(R^{31})C(O)N(R^{31})_2$, $-NR^{31}SO_2N(R^{31})_2$, $-NR^{31}SO_2R^{32}$, $-O-[CH_2]_p-O-$, $-S-[CH_2]_p-S-$ and $-[CH_2]_q-$. Preferably, substituents for the aryl or the heteroaryl group represented by $R^3$ include $Ak^3$, $-NO_2$, $-CN$, $-OR^{30}$, $-SR^{30}$, $-C(O)OR^{30}$, $-C(S)R^{30}$, $-OC(O)R^{30}$, $-C(O)N(R^{31})_2$, $-C(S)N(R^{31})_2$, $-N(R^{31})_2$, $-NR^{31}C(O)R^{30}$, $-NR^{31}C(O)OR^{32}$, $-N(R^{31})C(O)N(R^{31})_2$ and $-NR^{31}SO_2R^{32}$. More preferably, substituents for the aryl or the heteroaryl group represented by $R^3$ include halogen, $Ak^3$, $-OR^{30}$ and $-SR^{30}$. Even more preferably, substituents for the aryl or the heteroaryl group represented by $R^3$ include halogen, $C_{1-15}$ alkyl, $C_{1-15}$ haloalkyl, $-C_{2-6}$ alkynylene-$(C_{1-10}$ alkyl), $-C_{2-6}$ alkynylene-$Ar^4$, $-C_{1-6}$ alkylene-$Ar^4$, $-C_{1-6}$ alkylene-$N(R^{41})_2$, $-C_{1-6}$ alkylene-O-$Ar^4$, $-C_{1-6}$ alkylene-O-$Ak^4$-$Ar^4$, $-C_{1-6}$ alkylene-S-$Ar^4$, $-C_{1-6}$ alkylene-S-$Ak^4$-$Ar^4$, $-OC_{1-10}$ alkyl, $-O-C_{1-6}$ alkylene-$Ar^{00}$, $-SC_{1-10}$ alkyl and $-S-C_{1-6}$ alkylene-$Ar^{00}$. Specific examples of substituents for the aryl or the heteroaryl group represented by $R^3$, including rings A-O, include halogen; C1-C10 alkyl (e.g., methyl, ethyl, propyl, butyl and pentyl); C1-C3 haloalkyl; $-O$(C1-C10 alkyl); $-O-CH_2-CF_3$; phenyl; $-O$-Ph; $-O$-naphthyl; $-O-(CH_2)$-Ph; $-(CH_2)_2$-Ph;

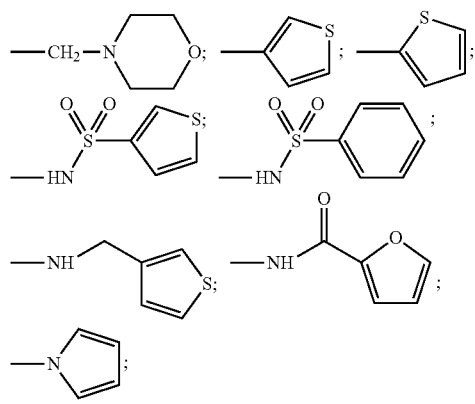

$-(CC)$-Ph; $-(CC)$-C1-C5 alkyl, $-CH_2-O$-Ph; $-CH_2-S$-Ph; $-CH_2-O-CH_2$-Ph; $-CH_2-S-CH_2$-Ph; and $-NH(C=O)-CH_3$, wherein each of the Ph (i.e., phenyl), naphthyl, thionyl, pyrrolyl and furanyl group is optionally substituted with one or more substituents selected from the group consisting of halogen, C1-C5 alkyl, methoxy, ethoxy and $-CF_3$.

Alternatively, $R^2$ and $R^3$ taken together with the nitrogen atom of $N(R^2R^3)$ form a substituted or unsubstituted non-aromatic heterocyclic ring. Preferably, the non-aromatic heterocyclic ring is 5-14 membered. More preferably, the non-aromatic heterocyclic ring is an unsubstituted five- or six-membered ring.

Suitable substituents for the non-aromatic heterocyclic ring represented by $N(R^2R^3)$ include halogen, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, nitro, cyano, hydroxy, $C_{1-10}$ alkoxycarbonyl, $C_{1-10}$ alkylcarbonyl, $C_{1-10}$ haloalkoxy, $(C_{1-10}$ haloakoxy)$C_{1-10}$ alkyl, $C_{1-10}$ haloalkyl, $C_{6-14}$ aryl and 5-14 membered heteroaryl. Preferably, substituents for the non-aromatic heterocyclic ring represented by $N(R^4R^5)$ include halogen, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, nitro, cyano, hydroxy, $C_{1-6}$ alkoxycarbonyl, $C_{1-6}$ alkylcarbonyl, $C_{1-6}$ haloalkoxy, $(C_{1-6}$ haloakoxy)$C_{1-6}$ alkyl, $C_{1-6}$ haloalkyl, $C_{6-14}$ aryl and 5-14 membered heteroaryl.

Each of $R^4$ and $R^5$ independently is $-H$ or $C_{1-6}$ alkyl. Preferably, each of $R^4$ and $R^5$ independently is $C_{1-6}$ alkyl. More preferably, each of $R^4$ and $R^5$ independently is methyl or ethyl. Even more preferably, each of $R^4$ and $R^5$ independently is methyl. In some embodiments, one of $R^4$ or $R^5$ is $C_{1-6}$ alkyl (e.g., methyl), and the other of $R^4$ or $R^5$ is $-H$. In some embodiments, each m and n is independently 1 or 2. In some embodiments, the sum of m and n is 3 or 4.

In some embodiments, Z is $N^+(R^4R^5)$ and each $R^4$ and $R^5$ are independently H or methyl. In some embodiments, each m and n is independently 1 or 2. In some embodiments, the sum of m and n is 3 or 4.

Each $R^{10}$ independently is i) hydrogen; ii) a $C_{1-20}$ aliphatic group optionally substituted with one or more substituents selected from the group consisting of halogen, $-NO_2$, $-CN$, $-Ar^0$, $-OR^{25}$, $-O-Ak^0-Ar^0$, $-SR^{25}$, $-S-Ak^0-Ar^0$, $-N(R^{26})_2$, $-NR^{26}C(O)R^{25}$, $NR^{26}C(O)R^{25}$, $-NR^{26}C(O)-Ak^0-Ar^0$, $-N(R^{26})C(O)N(R^{26})_2$, $-C(O)R^{25}$, $-C(O)-Ak^0-Ar^0$, $-C(S)R^{25}$, $-C(S)-Ak^0-Ar^0$, $-CO_2R^{25}$, $-CO_2-Ak^0-Ar^0$, $-OC(O)-R^{25}$, $-OC(O)-Ak^0-Ar^0$, $-C(O)N(R^{26})_2$, $-C(S)N(R^{26})_2$, $-S(O)_2R^{27}$, $-S(O)_2-Ak^0-Ar^0$, $-SO_2N(R^{26})_2$, $-NR^{26}SO_2N(R^{26})_2$, $-NR^{26}SO_2R^{27}$ and $-NR^{26}SO_2-Ak^0-Ar^0$; or iii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

Each $R^{11}$ independently is $R^{10}$, $-CO_2R^{10}$, $-SO_2R^{10}$ or $-C(O)R^{10}$, or $-N(R^{11})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by $-N(R^{11})_2$ are as described above for the non-aromatic heterocyclic group represented by $-N(R^2R^3)$.

Each $R^{12}$ independently is i) a $C_{1-20}$ aliphatic group optionally and independently substituted with one or more substituents selected from the group consisting of halogen, $-NO_2$, $-CN$, $-Ar^0$, $-OR^{25}$, $-O-Ak^0-Ar^0$, $-SR^{25}$, $-S-Ak^0-Ar^0$, $-N(R^{26})_2$, $-NR^{26}C(O)R^{25}$, $-NR^{26}C(O)-Ak^0-Ar^0$, $-N(R^{26})C(O)N(R^{26})_2$, $-C(O)R^{25}$, $-C(O)-Ak^0-Ar^0$, $-C(S)R^{25}$, $-C(S)-Ak^0-Ar^0$, $-CO_2R^{25}$, $-CO_2-Ak^0-Ar^0$, $-OC(O)-R^{25}$, $-OC(O)-Ak^0-Ar^0$, $-C(O)N(R^{26})_2$, $-C(S)N(R^{26})_2$, $-S(O)_2R^{27}$, $-S(O)_2-Ak^0-Ar^0$, $-SO_2N(R^{26})_2$, $-NR^{26}SO_2N(R^{26})_2$, $-NR^{26}SO_2R^{27}$ and $-NR^{26}SO_2-Ak^0-Ar^0$; or ii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

Preferably, each of $R^{10}$ and $R^{12}$ independently is i) a $C_{1-10}$ aliphatic group optionally substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$, —$N(R^{26})_2$, —$NR^{26}C(O)R^{25}$, —$NR^{26}C(O)$-$Ak^0$-$Ar^0$, —$C(O)R^{25}$, —$C(O)$-$Ak^0$-$Ar^0$, —$CO_2R^{25}$, —$CO_2$-$Ak^0$-$Ar^0$ and —$C(O)N(R^{26})_2$—; or a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl. More preferably, each of $R^{10}$ and $R^{12}$ independently is i) a $C_{1-10}$ aliphatic group optionally substituted with one or more substituents selected from the group consisting of halogen, —$Ar^0$, —$OR^{25}$, —O-$Ak^0$-$Ar^0$, —$SR^{25}$, —S-$Ak^0$-$Ar^0$ and —$N(R^{26})_2$; or ii) an $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, ($C_{1-6}$ haloalkoxy)$C_{1-6}$ alkyl and $C_{1-6}$ haloalkyl.

Each of $R^{20}$ and $R^{25}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, ($C_{1-10}$ alkoxy)$C_{1-15}$ alkyl, $C_{1-15}$ haloalkoxy, $C_{1-15}$ haloalkyl and ($C_{1-10}$ haloalkoxy)$C_{1-15}$ alkyl; or iii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy. Preferably, each of $R^{20}$ and $R^{25}$ independently is i) hydrogen, ii) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or iii) a $C_{1-10}$ alkyl group optionally and independently substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each of $R^{20}$ and $R^{25}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy) $C_{1-6}$ alkyl, $C_{1-6}$ haloalkoxy, $C_{1-6}$ haloalkyl and ($C_{1-6}$ haloalkoxy)$C_{1-6}$ alkyl; or iii) a $C_{1-10}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each $R^{21}$ independently is $R^{20}$, —$CO_2R^{20}$, or —$C(O)R^{20}$, or —$N(R^{21})_2$ taken together is an optionally substituted non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{21})_2$ are as described above for the non-aromatic heterocyclic group represented by —$N(R^2R^3)$.

Each $R^{26}$ independently is $R^{25}$, —$CO_2R^{25}$, —$SO_2R^{25}$ or —$C(O)R^{25}$, or —$N(R^{26})_2$ taken together is an optionally substituted non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{26})_2$ are as described above for the non-aromatic heterocyclic group represented by —$N(R^2R^3)$.

Each of $R^{22}$ and $R^{27}$ independently is i) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, ($C_{1-10}$ alkoxy)$C_{1-15}$ alkyl, $C_{1-15}$ haloalkoxy, $C_{1-15}$ haloalkyl and ($C_{1-10}$ haloalkoxy)$C_{1-15}$ alkyl; or ii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl, ($C_{1-10}$ haloalkoxy) $C_{1-15}$ alkyl and $C_{1-15}$ haloalkoxy. Preferably, each $R^{22}$ and $R^{27}$ independently is i) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or ii) a $C_{1-10}$ alkyl group optionally substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each $R^{22}$ and $R^{27}$ independently is i) a $C_{6-14}$ aryl or a 5-14 membered heteroaryl group optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, $C_{1-6}$ haloalkyl and ($C_{1-6}$ haloalkoxy)$C_{1-6}$ alkyl; or ii) a $C_{1-6}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each $R^{30}$ independently is i) hydrogen; ii) a $C_{1-20}$ aliphatic group optionally substituted with one or more substituents selected from the group consisting of halogen, —$NO_2$, —CN, —$Ar^{00}$, —$OR^{45}$, —O-$Ak^{00}$-$Ar^{00}$, —$SR^{45}$, —S-$Ak^{00}$-$Ar^{00}$, —$N(R^{46})_2$, —$NR^{46}C(O)R^{45}$, —$NR^{46}C(O)$-$Ak^{00}$-$Ar^{00}$, —$N(R^{46})C(O)N(R^{46})_2$, —$C(O)R^{45}$, —$C(O)$-$Ak^{00}$-$Ar^{00}$, —$C(S)R^{45}$, —$C(S)$-$Ak^{00}$-$Ar^{00}$, —$CO_2R^{45}$, —$CO_2$-$Ak^{00}$-$Ar^{00}$, —OC(O)—$R^{45}$, —OC(O)-$Ak^{00}$-$Ar^{00}$, —$C(O)N(R^{46})_2$—, —$C(S)N(R^{46})_2$, —$S(O)_2R^{47}$, —$S(O)_2$-$Ak^{00}$-$Ar^{00}$, —$SO_2N(R^{46})_2$, —$NR^{46}SO_2N(R^{46})_2$, —$NR^{46}SO_2R^{47}$ and —$NR^{46}SO_2$-$Ak^{00}$-$Ar^{00}$; or iii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

Each $R^{31}$ independently is $R^{30}$, —$CO_2R^{30}$, —$SO_2R^{30}$ or —$C(O)R^{30}$, or —$N(R^{31})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{31})_2$ are as described above for the non-aromatic heterocyclic group represented by —$N(R^2R^3)$.

Each $R^{32}$ independently is i) a $C_{1-20}$ aliphatic group optionally substituted with one or more substituents selected from the group consisting of halogen, —$NO_2$, —$CN$, —$Ar^{00}$, —$OR^{45}$, —O-$Ak^{00}$-$Ar^{00}$, —$SR^{45}$, —S-$Ak^{00}$-$Ar^{00}$, —$N(R^{46})_2$, —$NR^{46}C(O)R^{45}$, —$NR^{46}C(O)$-$Ak^{00}$-$Ar^{00}$, —$N(R^{46})C(O)N(R^{46})_2$, —$C(O)R^{45}$, —$C(O)$-$Ak^{00}$-$Ar^{00}$, —$C(S)R^{45}$, —$C(S)$-$Ak^{00}$-$Ar^{00}$, —$CO_2R^{45}$, —$CO_2$-$Ak^{00}$-$Ar^{00}$, —$OC(O)$—$R^{45}$, —$OC(O)$-$Ak^{00}$-$Ar^{00}$, $C(O)N(R^{46})_2$—, —$C(S)N(R^{46})_2$, —$S(O)_2R^{47}$, —$S(O)_2$-$Ak^{00}$-$Ar^{00}$, —$SO_2N(R^{46})_2$, —$NR^{46}SO_2N(R^{46})_2$, —$NR^{46}SO_2R^{47}$ and —$NR^{46}SO_2$-$Ak^{00}$-$Ar^{00}$; or ii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

Preferably, each of $R^{30}$ and $R^{32}$ independently is i) a $C_{1-10}$ aliphatic group optionally substituted with one or more substituents selected from the group consisting of halogen, —$NO_2$, —$CN$, —$Ar^{00}$, —$OR^{45}$, —O-$Ak^{00}$-$Ar^{00}$, —$SR^{45}$, —S-$Ak^{00}$-$Ar^{00}$, —$N(R^{46})_2$, —$NR^{46}C(O)R^{45}$, —$NR^{46}C(O)$-$Ak^{00}$-$Ar^{00}$, —$C(O)R^{45}$, —$C(O)$-$Ak^{00}$-$Ar^{00}$, —$CO_2R^{45}$, —$CO_2$-$Ak^{00}$-$Ar^{00}$ and —$C(O)N(R^{46})_2$—; or ii) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy)$C_{1-10}$ alkyl, $C_{1-10}$ haloalkoxy, $(C_{1-6}$ haloalkoxy)$C_{1-10}$ alkyl and $C_{1-10}$ haloalkyl. More preferably, each of $R^{30}$ and $R^{32}$ independently is i) a $C_{1-10}$ aliphatic group optionally substituted with one or more substituents selected from the group consisting of halogen, —$Ar^{00}$, —$OR^{45}$, —O-$Ak^{00}$-$Ar^{00}$, —$SR^{45}$, —S-$Ak^{00}$-$Ar^{00}$ and —$N(R^{46})_2$; or ii) an $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, $(C_{1-6}$ alkoxy)$C_{1-6}$ alkyl, $C_{1-6}$ haloalkoxy, $(C_{1-6}$ haloalkoxy)$C_{1-6}$ alkyl and $C_{1-6}$ haloalkyl.

Each of $R^{40}$ and $R^{45}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, $(C_{1-10}$ alkoxy)$C_{1-15}$ alkyl, $C_{1-15}$ haloalkoxy, $C_{1-15}$ haloalkyl and $(C_{1-10}$ haloalkoxy)$C_{1-15}$ alkyl; or iii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy. Preferably, each of $R^{40}$ and $R^{45}$ independently is i) hydrogen, ii) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy)$C_{1-10}$ alkyl, $C_{1-10}$ haloalkoxy, $C_{1-10}$ haloalkyl and $(C_{1-6}$ haloalkoxy)$C_{1-10}$ alkyl; or iii) a $C_{1-10}$ alkyl group optionally and independently substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each of $R^{40}$ and $R^{45}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, $(C_{1-6}$ alkoxy)$C_{1-6}$ alkyl, $C_{1-6}$ haloalkoxy, $C_{1-6}$ haloalkyl and $(C_{1-6}$ haloalkoxy)$C_{1-6}$ alkyl; or iii) a $C_{1-10}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each $R^{41}$ independently is $R^{40}$, —$CO_2R^{40}$, —$SO_2R^{40}$ or —$C(O)R^{40}$, or —$N(R^{41})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{41})_2$ are as described above for the non-aromatic heterocyclic group represented by —$N(R^2R^3)$.

Each $R^{46}$ independently is $R^{45}$, —$CO_2R^{45}$, —$SO_2R^{45}$ or —$C(O)R^{45}$, or —$N(R^{46})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{46})_2$ are as described above for the non-aromatic heterocyclic group represented by —$N(R^2R^3)$.

Each of $R^{42}$ and $R^{47}$ independently is i) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, $(C_{1-10}$ alkoxy)$C_{1-15}$ alkyl, $C_{1-15}$ haloalkoxy, $C_{1-15}$ haloalkyl and $(C_{1-10}$ haloalkoxy)$C_{1-15}$ alkyl; or ii) a $C_{1-15}$ alkyl group optionally substituted with one or more substituents selected from the group consisting halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy. Preferably, each $R^{42}$ and $R^{47}$ independently is i) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy)$C_{1-10}$ alkyl, $C_{1-10}$ haloalkoxy, $C_{1-10}$ haloalkyl and ($C_{1-6}$ haloalkoxy) $C_{1-10}$ alkyl; or ii) a $C_{1-10}$ alkyl group optionally substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each $R^{42}$ and $R^{47}$ independently is i) a $C_{6-14}$ aryl or a 5-14 membered heteroaryl group optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, $C_{1-6}$ haloalkyl and ($C_{1-6}$ haloalkoxy)$C_{1-6}$ alkyl; or ii) a $C_{1-6}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each of $Ak^0$ and $Ak^2$ independently is a $C_{1-20}$ alkylene, $C_{2-20}$ alkenylene or $C_{2-20}$ alkynylene group. Preferably, each of $Ak^0$ and $Ak^2$ independently is a $C_{1-10}$ alkylene, $C_{2-10}$ alkenylene or $C_{2-10}$ alkynylene group. More preferably, each of $Ak^0$ and $Ak^2$ independently is a $C_{1-10}$ alkylene group. Even more preferably, each of $Ak^0$ and $Ak^2$ independently is a $C_{1-6}$ alkylene group, such as —$CH_2$— or —$(CH_2)_2$—.

Each $Ak^1$ independently is an optionally substituted C1-C20 aliphatic group, preferably an optionally substituted C1-C15 aliphatic group. Suitable substituents for $Ak^1$ include halogen, —$NO_2$, —CN, —$Ar^2$, —$OR^{20}$, —O-$Ak^2$-$Ar^2$, —$SR^{20}$, —S-$Ak^2$-$Ar^2$, —$N(R^{21})_2$, —$NR^{21}C(O)R^{20}$, —$NR^{21}C(O)$-$Ak^2$-$Ar^2$, —$N(R^{21})C(O)N(R^{21})_2$, —$C(O)R^{20}$, —C(O)-$Ak^2$-$Ar^2$, —$C(S)R^{20}$, —C(S)-$Ak^2$-$Ar^2$, —$CO_2R^{20}$, —$CO_2$-$Ak^2$-$Ar^2$, —OC(O)—$R^{20}$—OC(O)-$Ak^2$-$Ar^2$, —$C(O)N(R^{21})_2$—, —$C(S)N(R^{21})_2$, —$S(O)_2R^{22}$, —$S(O)_2$-$Ak^2$-$Ar^2$, —$SO_2N(R^{21})_2$, —$SO_2N(R^{21})$—$NR^{21}$, —$S(O)R^{22}$, —S(O)-$Ak^2$-$Ar^2$, —$SO_3R^{22}$, —$SO_3$-$Ak^2$-$Ar^2$, —$NR^{21}SO_2N(R^{21})_2$, —$NR^{21}SO_2R^{22}$ and —$NR^{21}SO_2$-$Ak^2$-$Ar^2$. Preferred substituents for $Ak^1$ include —$Ar^2$, —$OR^{20}$, —O-$Ak^2$-$Ar^2$, —$SR^{20}$, —S-$Ak^2$-$Ar^2$, —$N(R^{21})_2$, —$NR^{21}C(O)R^{20}$, —$NR^{21}C(O)$-$Ak^2$-$Ar^2$, —$C(O)R^{20}$, —C(O)-$Ak^2$-$Ar^2$, —$C(S)R^{20}$, —C(S)-$Ak^2$-$Ar^2$, —$CO_2R^{20}$, —$CO_2$-$Ak^2$-$Ar^2$, —OC(O)—$R^{20}$—OC(O)-$Ak^2$-$Ar^2$, —$C(O)N(R^{21})_2$—, —$S(O)_2$—$R^{22}$, —$S(O)_2$-$Ak^2$-$Ar^2$, —$SO_2N(R^{21})_2$, —$SO_2N(R^{21})$—$NR^{21}$, —$S(O)R^{22}$, —S(O)-$Ak^2$-$Ar^2$, —$NR^{21}SO_2R^{22}$ and —$NR^{21}SO_2$-$Ak^2$-$Ar^2$. More preferred substituents for $Ak^1$ include —$Ar^2$, —$OR^{20}$, —O-$Ak^2$-$Ar^2$, —$SR^{20}$, —S-$Ak^2$-$Ar^2$, —$N(R^{21})_2$ and —$S(O)_2$-$Ak^2$-$Ar^2$.

Each $Ak^3$ independently is an optionally substituted C1-C20 aliphatic group, preferably an optionally substituted C1-C15 aliphatic group, more preferably an optionally substituted C1-C10 aliphatic group. Suitable substituents for $Ak^3$ include halogen, —$NO_2$, —CN, —$Ar^4$, —$OR^{40}$, —O-$Ak^4$-$Ar^4$, —$SR^{40}$, —S-$Ak^4$-$Ar^4$, —$N(R^{41})_2$, —$NR^{41}C(O)R^{40}$, —$NR^{41}C(O)$-$Ak^4$-$Ar^4$, —$N(R^{41})C(O)N(R^{41})_2$, —$C(O)R^{40}$, —C(O)-$Ak^4$-$Ar^4$, —$C(S)R^{40}$, —C(S)-$Ak^4$-$Ar^4$, —$CO_2R^{40}$, —$CO_2$-$Ak^4$-$Ar^4$, —OC(O)—$R^{40}$, —OC(O)-$Ak^4$-$Ar^4$, —$C(O)N(R^4)_2$—, —$C(S)N(R^{41})_2$, —$S(O)_2R^{42}$, —$S(O)_2$-$Ak^4$-$Ar^4$, —$SO_2N(R^{41})_2$, —$SO_2N(R^{41})$—$NR^{41}$, —$S(O)R^{42}$, —S(O)-$Ak^4$-$Ar^4$, —$SO_3R^{42}$, $SO_3$-$Ak^4$-$Ar^4$, —$NR^{41}SO_2N(R^{41})_2$, —$NR^{41}SO_2R^{42}$ and —$NR^{41}SO_2$-$Ak^4$-$Ar^4$. Preferred substituents for $Ak^3$ include —$Ar^4$, —$OR^{40}$, —O-$Ak^4$-$Ar^4$, —$SR^{40}$, —S-$Ak^4$-$Ar^4$, —$N(R^{41})_2$, —$NR^{41}C(O)R^{40}$, —$NR^{41}C(O)$-$Ak^4$-$Ar^4$, —$C(O)R^{40}$, —C(O)-$Ak^4$-$Ar^4$, —$C(S)R^{40}$, —C(S)-$Ak^4$-$Ar^4$, —$CO_2R^{40}$, —$CO_2$-$Ak^4$-$Ar^4$, —OC(O)—$R^{40}$—OC(O)-$Ak^4$-$Ar^4$, —$C(O)N(R^{41})_2$—, —$S(O)_2$—$R^{42}$, —$S(O)_2$-$Ak^4$-$Ar^4$, —$SO_2N(R^{41})_2$, —$SO_2N(R^{41})$—$NR^{41}$, —$S(O)R^{42}$, —S(O)-$Ak^4$-$Ar^4$, —$NR^{41}SO_2R^{42}$ and —$NR^{41}SO_2$-$Ak^4$-$Ar^4$. More preferred substituents for $Ak^3$ include —$Ar^4$, —$OR^{40}$, —O-$Ak^4$-$Ar^4$, —$SR^{40}$, —S-$Ak^4$-$Ar^4$, —$N(R^{41})_2$ and —$S(O)_2$-$Ak^4$-$Ar^4$.

Each of $Ak^{00}$ and $Ak^4$ independently is a $C_{1-20}$ alkylene, $C_{2-20}$ alkenylene or $C_{2-20}$ alkynylene group. Preferably, each of $Ak^{00}$ and $Ak^4$ independently is a $C_{1-10}$ alkylene, $C_{2-10}$ alkenylene or $C_{2-10}$ alkynylene group. More preferably, each of $Ak^{00}$ and $Ak^4$ independently is a $C_{1-10}$ alkylene group. Even more preferably, each of $Ak^{00}$ and $Ak^4$ independently is a $C_{1-6}$ alkylene group, such as —$CH_2$— or —$(CH_2)_2$—.

Each of $Ar^0$, $Ar^{00}$, $Ar^1$, $Ar^2$, $Ar^a$ and $Ar^4$ independently is an optionally substituted $C_{6-14}$ aryl or an optionally substituted 5-14 membered heteroaryl group. Preferably, each of $Ar^0$, $Ar^{00}$, $Ar^1$, $Ar^2$, $Ar^3$ and $Ar^4$ independently is an optionally substituted monocyclic aryl group or an optionally substituted monocyclic heteroaryl group, such as an optionally substituted phenyl group, or an optionally substituted 5- or 6-membered heteroaryl group.

Suitable substituents for each of the aryl and heteroaryl groups represented by $Ar^0$, $Ar^{00}$, $Ar^1$, $Ar^2$, $Ar^3$ and $Ar^4$ include halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, ($C_{1-10}$ alkoxy)$C_{1-20}$ alkyl, $C_{1-20}$ haloalkoxy, ($C_{1-10}$ haloalkoxy)$C_{1-20}$ alkyl and $C_{1-20}$ haloalkyl. Preferred substituents for each of the aryl and heteroaryl groups represented by $Ar^0$, $Ar^{00}$, $Ar^1$, $Ar^2$, $Ar^3$ and $Ar^4$ include halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl. More preferred substituents for each of the aryl and heteroaryl groups represented by $Ar^0$, $Ar^{00}$, $Ar^1$, $Ar^2$, $Ar^3$ and $Ar^4$ include, halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl.

Each p independently is 1, 2, 3 or 4. Preferably, each p independently is 1 or 2.

Each q independently is 3, 4, 5 or 6. Preferably, each q independently is 1 or 2.

A second set of values for the variables in Structural Formula (I) is provided in the following paragraphs:

$X^-$ is a pharmaceutically acceptable counter ion.

Z is —$N(R^4)$— or —$N^+(R^4R^5)X^-$—. Preferably, Z is —$N^+(R^4R^5)X^-$—.

$R^1$ is —OH or —$OC_{1-6}$ alkyl. Preferably, $R^1$ is —OH, —$OCH_3$ or —$OC_2H_5$.

$R^2$ is i) an aryl or a heteroaryl group optionally substituted with one or more substituents selected from the group consisting of halogen, $Ak^1$, $Ar^1$, —$NO_2$, —CN, —NCS, —C(O)$OR^{10}$, —$C(O)R^{10}$, —$C(S)R^{10}$, —$OC(O)R^{10}$, —$C(O)N(R^{11})_2$, —$C(S)N(R^{11})_2$, —$S(O)R^{12}$, —$S(O)_2R^{12}$, $SO_3R^{12}$, —$SO_2N(R^{11})_2$, —$SO_2N(R^{11})$—$NR^{11}$, —$OR^{10}$, —$SR^{10}$, —$N(R^{11})_2$, —$NR^{11}C(O)R^{10}$, —$NR^{11}S(O)R^{12}$, —$NR^{11}C(O)OR^{12}$, —$N(R^{11})C(O)N(R^{11})_2$, —$NR^{11}SO_2N(R^{11})_2$, —$NR^{11}SO_2R^{12}$, —O—$[CH_2]_p$—O—, —S—$[CH_2]_p$—S— and —$[CH_2]_q$—; or ii) an aliphatic group optionally substituted with one or more substituents selected from the group consisting of halogen, $Ar^1$, —$NO_2$, —CN, —NCS, —C(O)$OR^{10}$, —$C(O)R^{10}$, —$C(S)R^{10}$, —$OC(O)R^{10}$, —$C(O)N(R^{11})_2$, —$C(S)N(R^{11})_2$, —$S(O)R^{12}$, —$S(O)_2R^{12}$, —$SO_3R^{12}$, —$SO_2N(R^{11})_2$, —$SO_2N(R^{11})$—$NR^{11}$, —$OR^{10}$, —$SR^{10}$, —$N(R^{11})_2$, —$NR^{11}C(O)R^{10}$, —$NR^{11}S(O)R^{12}$, —$NR^{11}C(O)OR^{12}$, —$N(R^{11})C(O)N(R^{11})_2$, —$NR^{11}SO_2N(R^{11})_2$, and —$NR^{11}SO_2R^{12}$.

Each $R^3$ independently is a) an aliphatic group optionally substituted with one or more substituents selected from the group consisting of halogen, $Ar^3$, —$NO_2$, —CN, —NCS, —C(O)$OR^{30}$, —C(O)$R^{30}$, —C(S)$R^{30}$, —OC(O)$R^{30}$, —C(O)N$(R^{31})_2$, —C(S)N$(R^{31})_2$, —S(O)$R^{32}$, —S(O)$_2R^{32}$, —$SO_3R^{32}$, —$SO_2$N$(R^{31})_2$, —$SO_2$N$(R^{31})$—$NR^{31}$, —$OR^{30}$, —$SR^{30}$, —N$(R^{31})_2$, —$NR^{31}$C(O)$R^{30}$, —$NR^{31}$S(O)$R^{32}$, —$NR^{31}$C(O)$OR^{32}$, —N$(R^{31})$C(O)N$(R^{31})_2$, —$NR^{31}SO_2$N$(R^{31})_2$ and —$NR^{31}SO_2R^{32}$; or b) an aryl or a heteroaryl group optionally substituted with one or more substituents selected from the group consisting of halogen, $Ak^3$, $Ar^3$, —$NO_2$, —CN, —NCS, —C(O)$OR^{30}$, —C(O)$R^{30}$, —C(S)$R^{30}$, —OC(O)$R^{30}$, —C(O)N$(R^{31})_2$, —C(S)N$(R^{31})_2$, —S(O)$R^{32}$, —S(O)$_2R^{32}$, —$SO_3R^{32}$, —$SO_2$N$(R^{31})_2$, —$SO_2$N$(R^{31})$—$NR^{31}$, —$OR^{30}$, —$SR^{30}$, —N$(R^{31})_2$, —$NR^{31}$C(O)$R^{30}$, —$NR^{31}$S(O)$R^{32}$, —$NR^{31}$C(O)$OR^{32}$, —N$(R^{31})$C(O)N$(R^{31})_2$, —$NR^{31}SO_2$N, —$NR^{31}SO_2R^{32}$, —O—$[CH_2]_p$—O—, —S—$[CH_2]_p$—S— and —$[CH_2]_q$—.

Alternatively, $R^2$ and $R^3$ taken together with the nitrogen atom of N($R^2R^3$) form a substituted or unsubstituted non-aromatic heterocyclic ring.

Values and preferred values for the remainder of the variables of Structural Formula (I) are as described above for the first set of values.

A third set of values for the variables in Structural Formula (I) is provided in the following paragraphs:

Each Z, X, $R^1$, $R^2$, $R^3$, $R^4$ and $R^5$ independently is as described above in the second set of values for the variables in Structural Formula (I).

Q is —(C=O), —C(=S), —C(O)NH—, —C(S)NH—, —C(O)$NR^3$— or —C(S)$NR^3$—.

Each of $R^4$ and $R^5$ independently is $C_{1-6}$ alkyl, and preferably —$CH_3$.

In a second embodiment, the compound of the invention is represented by Structural Formula (II), or a pharmaceutically acceptable salt thereof:

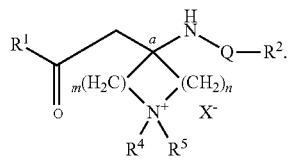

(II)

Values and preferred values for the variables of Structural Formula (II) are as described above for the first set, the second set or the third set of values for the variables of Structural Formula (I).

In a third embodiment, the compound of the invention is represented by Structural Formula (III), (IV), (V), (VI), (VII), (VIII), (IX) or (X), or a pharmaceutically acceptable salt thereof:

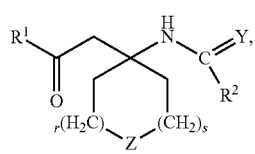

(III)

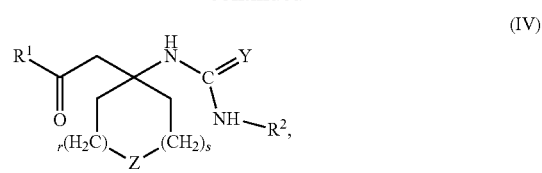

(IV)

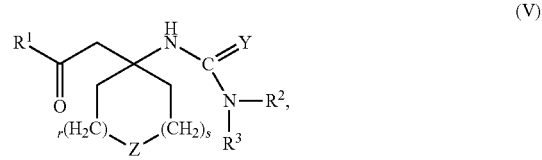

(V)

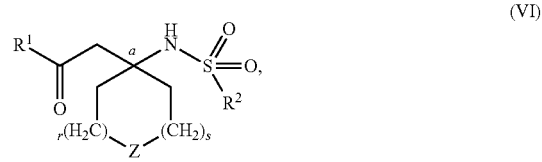

(VI)

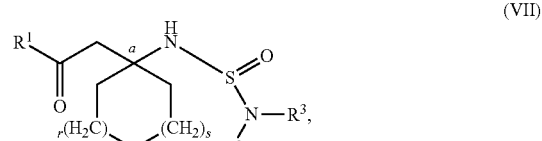

(VII)

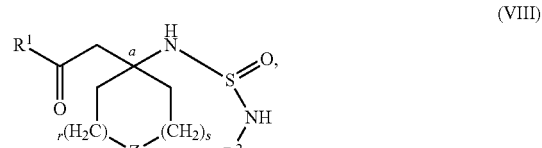

(VIII)

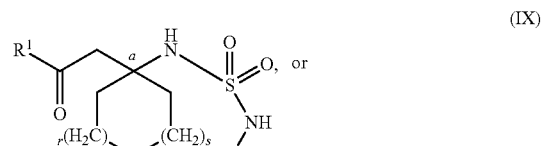

(IX)

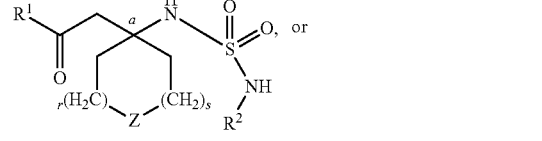

(X)

A first set of values for the variables of Structural Formulas (III)-(X) is provided in the following paragraphs:

$X^-$ is a pharmaceutically acceptable counter ion.

Each Y for Structural Formulas (III), (IV) and (V) independently is S or O.

Z is —N($R^4$)— or —$N^+$($R^4R^5$)$X^-$—. Preferably, Z is —$N^+$($R^4R^5$)$X^-$—.

Each of r and s independently is 0, 1 or 2, provided that the sum of r and s is 1 or 2.

$R^1$ is —OH or —$OC_{1-6}$ alkyl. Preferably, $R^1$ is —OH, —$OCH_3$ or —$OC_2H_5$.

Each $R^2$ independently is an optionally substituted C1-C20 aliphatic group, or an optionally substituted monocyclic aryl, or optionally substituted monocyclic heteroaryl group. In some embodiments, the aryl or the heteroaryl group represented by $R^2$ is selected from:

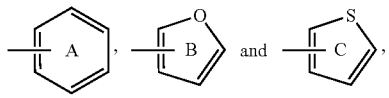

wherein each rings A-C is optionally and independently substituted with one or more substituents. In some embodiments $R^2$ is monosubstituted, e.g., with $C_1$-$C_{10}$ alkyl), —O($C_1$-$C_{10}$ alkyl), or —($C_1$-$C_{10}$)-Ph (e.g., phenethyl).

A common value for $R^2$ is

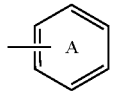

wherein ring A is optionally substituted with one or more substituents. In some preferred embodiments, A is substituted with at least one substitutent, for example, A is substituted on the para position.

In some embodiments $R^2$ is monosubstituted, e.g., with $C_1$-$C_{10}$ alkyl), —O($C_1$-$C_{10}$ alkyl), or —($C_1$-$C_{10}$)-Ph (e.g., phenethyl).

Each $R^3$ for Structural Formulas (V), (VII) and (X) independently is an optionally substituted aliphatic group.

Each of $R^4$ and $R^5$ independently is $C_{1-6}$ alkyl, and preferably —$CH_3$. In some embodiments, one or $R^4$ or $R^5$ is H.

Values and preferred values for the remainder of the variables of Structural Formulas (III)-(X) are as described above for the first set of values for the variables of Structural Formula (I).

A second set of values for the variables of Structural Formulas (III)-(X) is provided in the following paragraphs:

Each $R^2$ independently is i) a C1-C20 aliphatic group optionally substituted with one or more substituents selected from the group consisting of $Ar^1$, —$NO_2$, —CN, —$OR^{10}$, —$SR^{10}$, —C(O)$OR^{10}$, —C(O)$R^{10}$, —C(S)$R^{10}$, —OC(O)$R^{10}$, —C(O)N($R^{11}$)$_2$, —C(S)N($R^{11}$)$_2$, —N($R^{11}$)$_2$, —$NR^{11}$C(O)$R^{10}$, —$NR^{11}$C(O)$OR^{12}$, —N($R^{11}$)C(O)N($R^{11}$)$_2$ and —$NR^{11}$SO$_2R^{12}$; or ii) a monocyclic aryl or monocyclic heteroaryl group optionally substituted with one or more substituents selected from the group consisting of $Ak^1$, —$NO_2$, —CN, —$OR^{10}$, —$SR^{10}$, —C(O)$OR^{10}$, —C(O)$R^{10}$, —C(S)$R^{10}$, —OC(O)$R^{10}$, —C(O)N($R^{11}$)$_2$, —C(S)N($R^{11}$)$_2$, —N($R^{11}$)$_2$, —$NR^{11}$C(O)$R^{10}$, —$NR^{11}$C(O)$OR^{12}$, —N($R^{11}$)C(O)N($R^{11}$)$_2$ and —$NR^{11}$SO$_2R^{12}$.

Each $X^-$, Y, Z, r, s, $R^1$, $R^3$, $R^4$ and $R^5$ independently is as described above in the first set of values for the variables of Structural Formulas (III)-(X).

Values and preferred values for the remainder of the variables of Structural Formulas (III)-(X) are as described above for the first set of values for the variables of Structural Formula (I).

A third set of values for the variables of Structural Formulas (III)-(X) is provided in the following paragraphs:

Each $Ak^1$ independently is optionally substituted with one or more substituents selected from the group consisting of halogen, —$Ar^2$, —$OR^{20}$, —O-$Ak^2$-$Ar^2$, —$SR^{20}$, —S-$Ak^2$-$Ar^2$, —N($R^{21}$)$_2$, —$NR^{21}$C(O)$R^{20}$, —$NR^{21}$C(O)-$Ak^2$-$Ar^2$, —C(O)$R^{20}$, —C(O)-$Ak^2$-Ar, —C(S)$R^{20}$, —C(S)-$Ak^2$-Ar, —$CO_2R^{20}$, —$CO_2$-$Ak^2$-$Ar^2$, —OC(O)—$R^{20}$, —OC(O)-$Ak^2$-$Ar^2$, —C(O)N($R^{21}$)$_2$—, —S(O)$_2R^{22}$, —S(O)$_2$-$Ak^2$-$Ar^2$, —SO$_2$N($R^{21}$)$_2$, —SO$_2$N($R^{21}$)—$NR^{21}$, —S(O)$R^{22}$, —S(O)-$Ak^2$-$Ar^2$, —$NR^{21}$SO$_2R^{22}$ and —$NR^{21}$SO$_2$-$Ak^2$-$Ar^2$.

Each $R^3$ for Structural Formulas (V), (VII) and (X) independently is a C1-C20 aliphatic group optionally substituted with one or more substituents selected from the group consisting of $Ar^3$, —$NO_2$, —CN, —$OR^{30}$, —$SR^{30}$, —C(O)$OR^{30}$, —C(O)$R^{30}$, —C(S)$R^{30}$, —OC(O)$R^{30}$, —C(O)N($R^{31}$)$_2$, —C(S)N($R^{31}$)$_2$, —N($R^{31}$)$_2$, $NR^{31}$C(O)$R^{30}$, —$NR^{31}$C(O)$OR^{32}$, —N($R^{31}$)C(O)N($R^{31}$)$_2$ and —$NR^{31}$SO$^2R^{32}$.

Each $X^-$, Y, Z, r, s, $R^1$, $R^2$, $R^4$ and $R^5$ independently is as described above in the second set of values for the variables of Structural Formulas (III)-(X).

Values and preferred values for the remainder of the variables of Structural Formulas (III)-(X) are as described above for the first set of values for the variables of Structural Formula (I).

A fourth set of values for the variables of Structural Formulas (III)-(X) is provided in the following paragraphs:

Each of $R^{10}$ and $R^{12}$ independently is i) a $C_{1-10}$ aliphatic group optionally substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$, —N($R^{26}$)$_2$, —$NR^{26}$C(O)$R^{25}$, —$NR^{26}$C(O)-$Ak^0$-$Ar^0$, —C(O)$R^{25}$, —C(O)-$Ak^0$-$Ar^0$, —$CO_2R^{25}$, —$CO_2$-$Ak^0$-$Ar^0$ and —C(O)N($R^{26}$)$_2$—; or ii) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl.

Each of $R^{30}$ and $R^{32}$ for Structural Formulas (V), (VII) and (X) independently is i) a $C_{1-10}$ aliphatic group optionally substituted with one or more substituents selected from the group consisting of halogen, —$NO_2$, —CN, —$Ar^{00}$, —$OR^{45}$, —O-$Ak^{00}$-$Ar^{00}$, —$SR^{45}$, —S-$Ak^{00}$-$Ar^{00}$, —N($R^{46}$)$_2$, —$NR^{46}$C(O)$R^{45}$, —$NR^{46}$C(O)-$Ak^{00}$-$Ar^{00}$, —C(O)$R^{45}$, —C(O)-$Ak^{00}$-$Ar^{00}$, —$CO_2R^{45}$, —$CO_2$-$Ak^{00}$-$Ar^{00}$ and —C(O)N($R^{46}$)$_2$—; or ii) a $C_{6-14}$ aryl or a 5-14 membered D heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl.

Each of $R^{20}$, $R^{25}$ and $R^{45}$ independently is i) hydrogen, ii) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or iii) a $C_{1-10}$ alkyl group optionally substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy.

Each of the non-aromatic heterocyclic group represented by —N($R^{21}$)$_2$, —N($R^{26}$)$_2$, and —N($R^{46}$)$_2$ optionally and independently is substituted with one or more substituents selected from the group consisting of halogen, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, nitro, cyano, hydroxy, $C_{1-10}$ alkoxycarbonyl, $C_{1-10}$ alkylcarbonyl, $C_{1-10}$ haloalkoxy, ($C_{1-6}$ haloalkoxy)$C_{1-10}$ alkyl, $C_{1-10}$ haloalkyl, $C_{6-14}$ aryl and 5-14 membered heteroaryl.

Each $R^{22}$ independently is i) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or ii) a $C_{1-10}$ alkyl group optionally substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy.

Each of $Ak^0$, $Ak^2$ and $Ak^{00}$ independently is a C1-C10 alkylene group.

Each $X^-$, Y, Z, r, s, $R^1$, $R^2$, $R^4$ and $R^5$ independently is as described above in the third set of values for the variables of Structural Formulas (III)-(X).

Values and preferred values for the remainder of the variables of Structural Formulas (III)-(X) are as described above for the first set of values for the variables of Structural Formula (I).

In a fifth set, values and preferred values of each variable of Structural Formulas (III)-(X) are independently as described above for the first set, the second set, or the third set of values for the variables of Structural Formula (I).

In a fourth embodiment, the compound of the invention is represented by Structural Formula (XI), (XII), (XIII), (XIV), (XV), (XVI), (XVII) or (XVIII), or a pharmaceutically acceptable salt thereof:

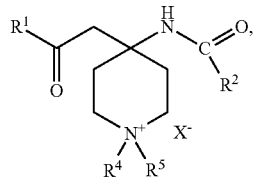
(XI)

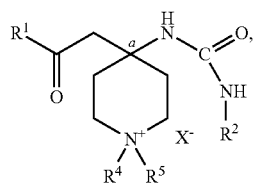
(XII)

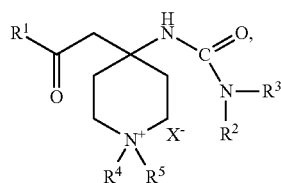
(XIII)

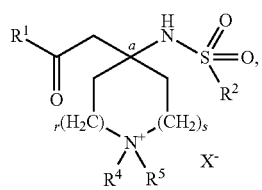
(XIV)

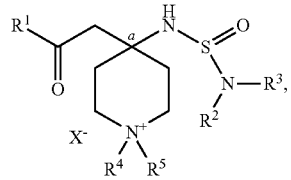
(XV)

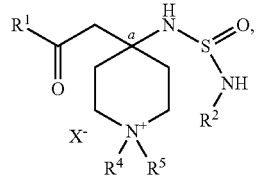
(XVI)

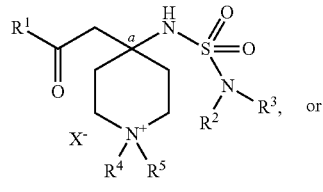
(XVII)

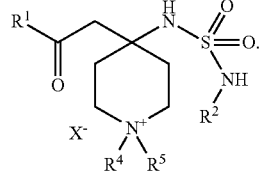
(XVIII)

A first set of values for the variables of Structural Formulas (XI)-(XVIII) is provided in the following paragraphs:

Each $X^-$ independently is a pharmaceutically acceptable counter ion.

$R^1$ is —OH or —$OC_{1-6}$ alkyl. Preferably, $R^1$ is —OH, —$OCH_3$ or —$OC_2H_5$.

Each $R^2$ for Structural Formulas (XI), (XII) and (XIV) independently is i) a C1-C20 alkyl group optionally substituted with one or more substituents selected from the group consisting of $Ar^1$, —$NO_2$, —CN, —OAk, —$SR^{10}$, —C(O)$OR^{10}$, —C(O)$R^{10}$, —C(S)$R^{10}$, —OC(O)$R^{10}$, —C(O)N($R^{11}$)$_2$, —C(S)N($R^{11}$)$_2$, —N($R^{11}$)$_2$, —$NR^{11}$C(O)$R^{10}$, —$NR^{11}$C(O)$OR^{12}$, —N($R^{11}$)C(O)N($R^{11}$)$_2$ and —$NR^{11}SO_2R^{12}$, wherein Ak is C1-C10 aliphatic group optionally substituted with halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy; or ii) a monocyclic aryl or monocyclic heteroaryl group optionally substituted with one or more substituents selected from the group consisting of $Ak^1$, —$NO_2$, —CN, —$OR^{10}$, —$SR^{10}$, —C(O)$OR^{10}$, —C(O)$R^{10}$, —C(S)$R^{10}$, —OC(O)$R^{10}$, —C(O)N($R^{11}$)$_2$, —C(S)N($R^{11}$)$_2$, —N($R^{11}$)$_2$, —$NR^{11}$C(O)$R^{10}$, —$NR^{11}$C(O)$OR^{12}$, —N($R^{11}$)C(O)N($R^{11}$)$_2$ and —$NR^{11}SO_2R^{12}$.

Each $R^2$ for Structural Formulas (XIII), (XV), (XVI), (XVII) and (XVIII) independently is i) a C1-C20 alkyl group optionally substituted with one or more substituents selected from the group consisting of $Ar^1$, —$NO_2$, —CN, —$OR^{10}$, —$SR^{10}$, —C(O)$OR^{10}$, —C(O)$R^{10}$, —C(S)$R^{10}$, —OC(O)$R^{10}$, —C(O)N($R^{11}$)$_2$, —C(S)N($R^{11}$)$_2$, —N($R^{11}$)$_2$, —$NR^{11}$C(O)$R^{10}$, —$NR^{11}$C(O)$OR^{12}$, —N($R^{11}$)C(O)N($R^{11}$)$_2$ and —$NR^{11}SO_2R^{12}$; or ii) a monocyclic aryl or monocyclic heteroaryl group optionally substituted with one or more substituents selected from the group consisting of $Ak^1$, —$NO_2$, —CN, —OR$^{10}$, —SR$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —N(R$^{11}$)$_2$, —NR$^{11}$C(O)R$^{10}$, —NR$^{11}$C(O)OR$^{12}$, —N(R$^{11}$)C(O)N(R$^{11}$)$_2$ and —NR$^{11}$SO$_2$R$^{12}$.

In some embodiments, R$^2$ is selected from:

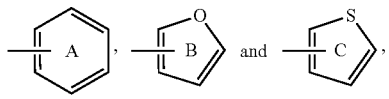

wherein each rings A-C is optionally and independently substituted with one or more substituents. In some embodiments R$^2$ is monosubstituted, e.g., with C$_1$-C$_{10}$ alkyl), —O(C$_1$-C$_{10}$ alkyl), or —(C$_1$-C$_{10}$)-Ph (e.g., phenethyl).

In some embodiments, R$^2$ is

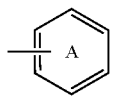

wherein ring A is optionally substituted with one or more substituents. In some preferred embodiments, A is substituted with at least one substitutent, for example, A is substituted on the para position. In some embodiments R$^2$ is monosubstituted, e.g., with C$_1$-C$_{10}$ alkyl), —O(C$_1$-C$_{10}$ alkyl), or —(C$_1$-C$_{10}$)-Ph (e.g., phenethyl).

Each R$^3$ for Structural Formulas (XIII), (XV) and (XVII) independently is an unsubstituted C1-C10 alkyl group.

Each of R$^{10}$ and R$^{12}$ independently is i) a C$_{1-10}$ aliphatic group optionally substituted with one or more substituents selected from the group consisting of halogen, —NO$_2$, —CN, —Ar$^0$, —OR$^{25}$, —O-Ak$^0$-Ar$^0$, —SR$^{25}$, —S-Ak$^0$-Ar$^0$, —N(R$^{26}$)$_2$, —NR$^{26}$C(O)R$^{25}$, —NR$^{26}$C(O)-Ak$^0$-Ar$^0$, —C(O)R$^{25}$, —C(O)-Ak$^0$-Ar$^0$, —CO$_2$R$^{25}$, —CO$_2$-Ak$^0$-Ar$^0$ and —C(O)N(R$^{26}$)$_2$—; or ii) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, (C$_{1-6}$ haloalkoxy)C$_{1-10}$ alkyl and C$_{1-10}$ haloalkyl.

Each of R$^{20}$ and R$^{25}$ independently is i) hydrogen, ii) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, C$_{1-10}$ haloalkyl and (C$_{1-6}$ haloalkoxy)C$_{1-10}$ alkyl; or iii) a C$_{1-10}$ alkyl group optionally substituted with one or more substituents selected from the group consisting of halogen, hydroxyl, amino, C$_{1-10}$ alkylamino, C$_{1-10}$ dialkylamino, C$_{1-10}$ alkoxy, nitro, cyano, C$_{1-10}$ alkoxycarbonyl, C$_{1-10}$ alkylcarbonyl and C$_{1-10}$ haloalkoxy.

The non-aromatic heterocyclic group represented by —N(R$^{21}$)$_2$ is optionally substituted with one or more substituents selected from the group consisting of halogen, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, nitro, cyano, hydroxy, C$_{1-10}$ alkoxycarbonyl, C$_{1-10}$ alkylcarbonyl, C$_{1-10}$ haloalkoxy, (C$_{1-6}$ haloalkoxy)C$_{1-10}$ alkyl, C$_{1-10}$ haloalkyl, C$_{6-14}$ aryl and 5-14 membered heteroaryl.

Each R$^{22}$ independently is i) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, C$_{1-10}$ haloalkyl and (C$_{1-6}$ haloalkoxy)C$_{1-10}$ alkyl; or ii) a C$_{1-10}$ alkyl group optionally substituted with one or more substituents selected from the group consisting of halogen, hydroxyl, amino, C$_{1-10}$ alkylamino, C$_{1-10}$ dialkylamino, C$_{1-10}$ alkoxy, nitro, cyano, C$_{1-10}$ alkoxycarbonyl, C$_{1-10}$ alkylcarbonyl and C$_{1-10}$ haloalkoxy.

Each of Ak$^0$ and Ak$^2$ independently is a C1-C10 alkylene group.

Each Ak$^1$ independently is optionally substituted with one or more substitutents selected from the group consisting of halogen, —Ar$^2$, —OR$^{20}$, —O-Ak$^2$-Ar$^2$, —SR$^{20}$, —S-Ak$^2$-Ar$^2$, —N(R$^{21}$)$_2$, —NR$^{21}$C(O)R$^{20}$, —NR$^{21}$C(O)-Ak$^2$-Ar$^2$, —C(O)R$^{20}$, —C(O)-Ak$^2$-Ar, —C(S)R$^{20}$, —C(S)-Ak$^2$-Ar, —CO$_2$R$^{20}$, —CO$_2$-Ak$^2$-Ar$^2$, —OC(O)—R$^{20}$, —OC(O)-Ak$^2$-Ar$^2$, —C(O)N(R$^{21}$)$_2$—, —S(O)$_2$R$^{22}$, —S(O)$_2$-Ak$^2$-Ar$^2$, —SO$_2$N(R$^{21}$)$_2$, —SO$_2$N(R$^{21}$)—NR$^{21}$, —S(O)R$^{22}$, —S(O)-Ak$^2$-Ar$^2$, —NR$^{21}$SO$_2$R$^{22}$ and —NR$^{21}$SO$_2$-Ak$^2$-Ar$^2$.

Values and preferred values for the remainder of the variables of Structural Formulas (XI)-(XVIII) are as described above for the first set of values for the variables of Structural Formula (I).

A second set of values for the variables of Structural Formulas (XI)-(XVIII) is provided in the following paragraphs:

Each R$^2$ for Structural Formulas (XI), (XII) and (XIII) independently is an optionally substituted C1-C15 alkyl group, or is an aryl or heteroaryl group selected from the group consisting of:

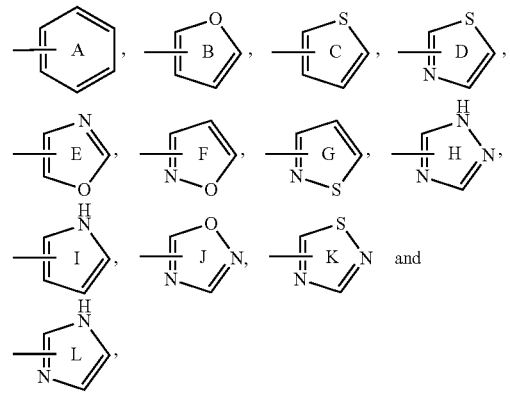

wherein each of rings A-L is optionally substituted.

Each R$^2$ for Structural Formulas (XIV), (XV), (XVI), (XVII) and (XVIII) independently is an optionally substituted C1-C15 alkyl group, or is an aryl or heteroaryl group selected from the group consisting of

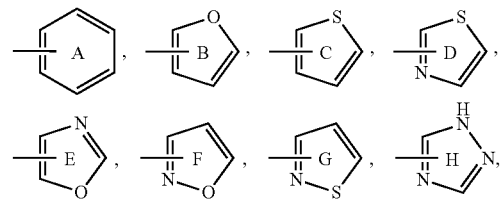

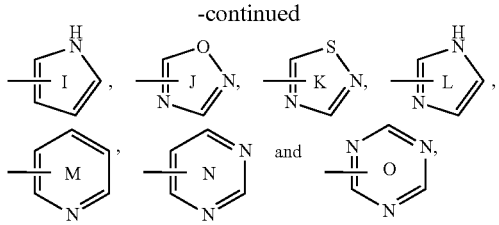

wherein each of rings A-O is optionally substituted. Preferably, each $R^2$ for Structural Formulas (XIV), (XV), (XVI), (XVII) and (XVIII) independently is an optionally substituted C1-C15 alkyl group, or is an aryl or heteroaryl group selected from rings A-L.

Suitable substituents for the C1-C15 alkyl group represented by $R^2$ for Structural Formulas (XI), (XII) and (XIV) include $Ar^1$, —$NO_2$, —CN, —OAk, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO_2R^{12}$. Suitable substituents for the C1-C15 alkyl group represented by $R^2$ for Structural Formulas (XIII), (XV), (XVI), (XVII) and (XVIII) include $Ar^1$, —$NO_2$, —CN, —$OR^{10}$, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO_2R^{12}$.

Preferably, each $R^2$ for Structural Formulas (XI), (XII) and (XIV) independently is i) a C1-C15 alkyl group optionally substituted with halogen, $Ar^1$, —OH, —OAk and —$SR^{10}$, or ii) an aryl or a heteroaryl group selected from rings A-L, each of rings A-L being optionally substituted with one or more substituents. Preferably, each $R^2$ for Structural Formulas (XIV), (XV), (XVI), (XVII) and (XVIII) independently is i) a C1-C15 alkyl group optionally substituted with halogen, $Ar^1$, —$OR^{10}$ and —$SR^{10}$, or ii) an aryl or a heteroaryl group selected from rings A-L, each of rings A-L being optionally substituted with one or more substituents. Preferred substituents for rings A-L include halogen, $Ak^1$, —$OR^{10}$ and —$SR^{10}$.

In some embodiments, $R^2$ is selected from:

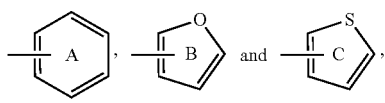

wherein each rings A-C is optionally and independently substituted with one or more substituents. In some embodiments $R^2$ is monosubstituted, e.g., with $C_1$-$C_{10}$ alkyl), —O($C_1$-$C_{10}$ alkyl), or —($C_1$-$C_{10}$)-Ph (e.g., phenethyl).

In some embodiments, $R^2$ is

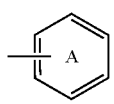

wherein ring A is optionally substituted with one or more substituents. In some preferred embodiments, A is substituted with at least one substitutent, for example, A is substituted on the para position. In some embodiments $R^2$ is monosubstituted, e.g., with $C_1$-$C_{10}$ alkyl), —O($C_1$-$C_{10}$ alkyl), or —($C_1$-$C_{10}$)-Ph (e.g., phenethyl).

Each X, $R^1$, $R^3$, $R^4$, $R^5$, $R^{10}$, $R^{12}$, $R^{20}$, $R^{22}$, $R^{25}$, $Ak^0$, $Ak^1$ and $Ak^2$ independently is as described above in the first set of values for the variables in Structural Formulas (XI)-(XVIII).

Values and preferred values for the remainder of the variables of Structural Formulas (XI)-(XVIII) are as described above for the first set of values for the variables of Structural Formula (I).

A third set of values for the variables of Structural Formulas (XI)-(XVIII) is provided in the following paragraphs:

Each $R^{10}$ independently is i) a $C_{1-10}$ aliphatic group optionally substituted with one or more substituents selected from the group consisting of halogen, —$Ar^0$, —$OR^{25}$, —O-$Ak^0$-$Ar^0$, —$SR^{25}$, —S-$Ak^0$-$Ar^0$ and —$N(R^{26})_2$; or ii) an $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy) $C_{1-6}$ alkyl, $C_{1-6}$ haloalkoxy, ($C_{1-6}$ haloalkoxy)$C_{1-6}$ alkyl and $C_{1-6}$ haloalkyl.

Each of $R^{20}$ and $R^{25}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, $C_{1-6}$ haloalkyl and ($C_{1-6}$ haloalkoxy)$C_{1-6}$ alkyl; or iii) a $C_{1-10}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl, ($C_{1-6}$ haloalkoxy)$C_{1-6}$ alkyl, and $C_{1-6}$ haloalkoxy.

Each $Ak^0$ and $Ak^2$ independently is a $C_1$-$C_6$ alkylene group.

Each $Ak^1$ independently is a C1-C15 aliphatic group optionally substituted with one or more substituents selected from the group consisting of halogen, —$Ar^2$, —$OR^{20}$, —O-$Ak^2$-$Ar^2$, —$SR^{20}$, —S-$Ak^2$-$Ar^2$, —$N(R^{21})_2$ and —$S(O)_2$-$Ak^2$-$Ar^2$.

Each X, $R^1$, $R^2$, $R^3$, $R^4$, $R^5$, $R^{12}$ and $R^{22}$ independently is as described above in the second set of values for the variables of Structural Formulas (XI)-(XVIII).

Values and preferred values for the remainder of the variables of Structural Formulas (XI)-(XVIII) are as described above for the first set of values for the variables of Structural Formula (I).

A fourth set of values for the variables of Structural Formulas (XI)-(XVIII) is provided in the following paragraphs:

Each $R^2$ for Structural Formulas (XI)-(XVIII) independently is selected from the group consisting of:

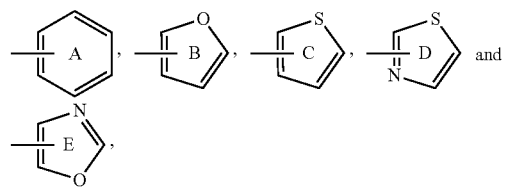

wherein each rings A-E is optionally and independently substituted with one or more substituents. Preferably, each $R^2$ independently is selected from the group consisting of:

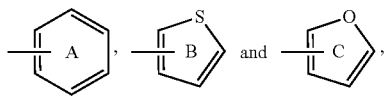

wherein each of rings A-C is optionally and independently substituted with one or more substituents. Preferred substituents for rings A-E include halogen, $Ak^1$, $-OR^{10}$ and $-SR^{10}$. Preferable substituents for rings A-E include $C_{1-15}$ alkyl, $C_{1-15}$ haloalkyl, $-C_{2-6}$ alkynylene-$(C_{1-10}$ alkyl), $-C_{2-6}$ alkynylene-$Ar^2$, $-C_{1-6}$ alkylene-$Ar^2$, $-C_{1-6}$ alkylene-$N(R^{21})_2$, $-C_{1-6}$ alkylene-O—$Ar^2$, $-C_{1-6}$ alkylene-O-$Ak^2$-$Ar^2$, $-C_{1-6}$ alkylene-S—$Ar^2$, $-C_{1-6}$ alkylene-S-$Ak^2$-$Ar^2$, $-OC_{1-10}$ alkyl, $-O-C_{1-6}$ alkylene-$Ar^0$, $-SC_{1-10}$ alkyl and $-S-C_{1-6}$ alkylene-$Ar^0$.

In some embodiments, the aryl or the heteroaryl group represented by $R^2$ is selected from:

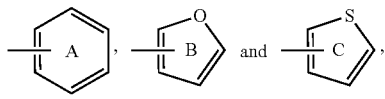

wherein each rings A-C is optionally and independently substituted with one or more substituents. In some embodiments $R^2$ is monosubstituted, e.g., with $C_1$-$C_{10}$ alkyl), $-O(C_1$-$C_{10}$ alkyl), or $-(C_1$-$C_{10})$-Ph (e.g., phenethyl).

In some embodiments, $R^2$ is

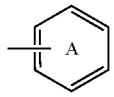

wherein ring A is optionally substituted with one or more substituents. In some preferred embodiments, A is substituted with at least one substitutent, for example, A is substituted on the para position.

In some embodiments $R^2$ is monosubstituted, e.g., with $C_1$-$C_{10}$ alkyl), $-O(C_1$-$C_{10}$ alkyl), or $-(C_1$-$C_{10})$-Ph (e.g., phenethyl).

Each $R^4$ and $R^5$ independently is $-CH_3$. In some embodiments, one of $R^4$ or $R^5$ is H and one of $R^4$ or $R^5$ is $-CH^3$.

Each X, $R^1$, $R^3$, $R^{10}$, $Ak^0$, $Ak^1$ and $Ak^2$ independently is as described above in the third set of values for the variables of Structural Formulas (XI)-(XVIII).

Values and preferred values for the remainder of the variables of Structural Formulas (XI)-(XVIII) are as described above for the first set of values for the variables of Structural Formula (I).

In a fifth set, values and preferred values of each variable of Structural Formulas (XI)-(XVIII) independently are as described above for the first set, the second set, or the third set of values for the variables of Structural Formulas (I).

In a sixth set, values and preferred values of each variable of Structural Formulas (XI)-(XVIII) independently are as described above for the first set, second set, third set, or fourth set of values for the variables of Structural Formulas (III)-(X).

In a fifth embodiment, the compound of the invention is represented by Structural Formula (XIX), (XX), (XXI), (XXII), (XXIII), (XXIV), (XXV), (XXVI), (XXVII), (XXVIII), (XXIX), (XXX), (XXXI), (XXXII), (XXXIII) or (XXXIV), or a pharmaceutically acceptable salt thereof:

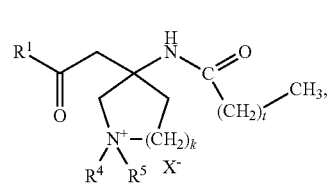
(XIX)

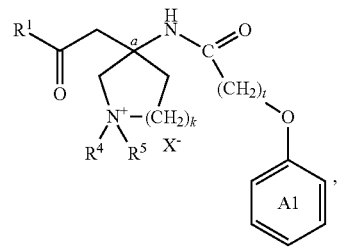
(XX)

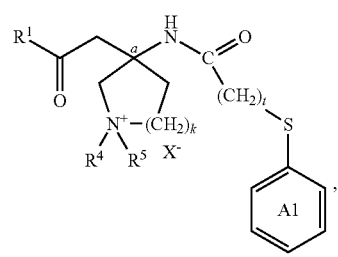
(XXI)

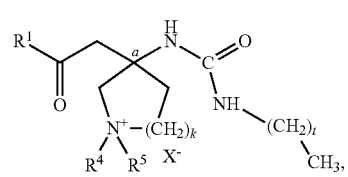
(XXII)

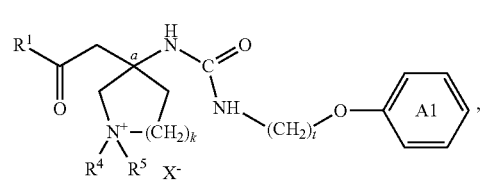
(XXIII)

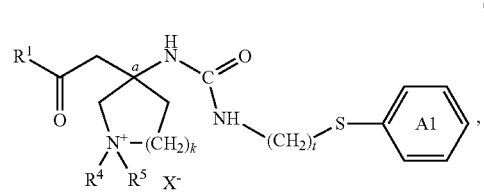
(XXIV)

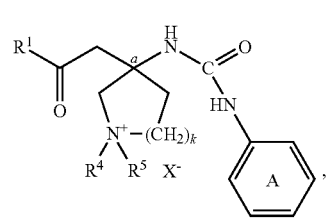
(XXV)

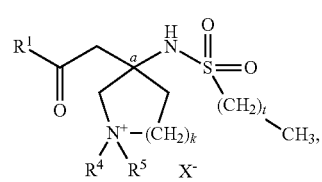
(XXVI)

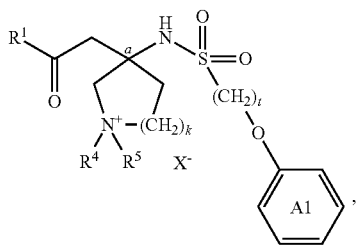
(XXVII)

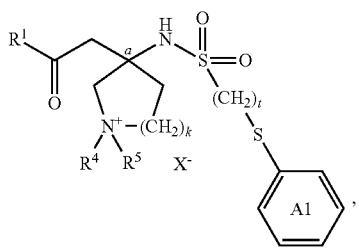
(XXVIII)

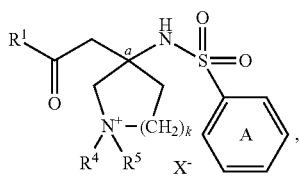
(XXIX)

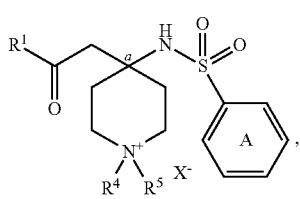
(XXX)

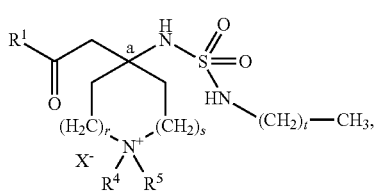
(XXXI)

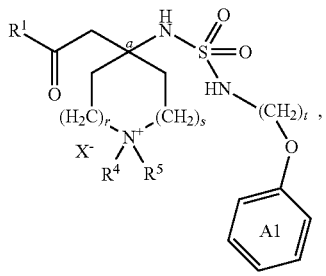
(XXXII)

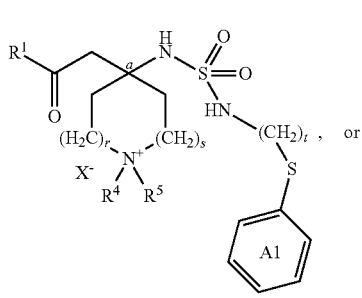
(XXXIII)

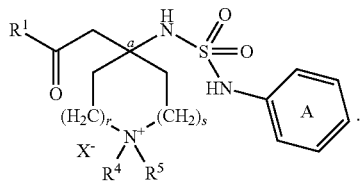
(XXXIV)

A first set of values for the variables of Structural Formulas (XIX)-(XXXIV) is provided in the following paragraphs:

Each $X^-$ independently is a pharmaceutically acceptable counter ion.

Each t for Structural Formulas (XIX), (XX), (XXI), (XXII), (XXIII), (XXIV), (XXVI), (XXVII), (XXVIII), (XXXI), (XXXII) and (XXXIII) independently is 1, 2, 3, 4, 5, 6, 7, 8, 9 or 10. Preferably, each t independently is 6, 7, 8, 9 or 10.

Each k for Structural Formulas (XIX)-(XXIX) independently is 1 or 2.

Each of r and s for Structural Formulas (XXXI)-(XXXIV) independently is 0, 1, or 2, provided that the sum of r and s is 1 or 2.

Each ring A1 for Structural Formulas (XX), (XXI), (XXIII), (XXIV), (XXVII), (XXVIII), (XXXII) and (XXXIII) independently and optionally is substituted with one or more substituents. Suitable substituents include halogen, $C_{1-15}$ alkyl (e.g., $C_{1-10}$ alkyl or $C_{3-10}$ alkyl), $C_{1-6}$ haloalkyl, —O—$C_{1-10}$ alkyl and ($C_{1-6}$ alkoxy)$C_{1-6}$ alkyl. In some preferred embodiments, A1 is monosubstituted (e.g., with $C_{1-10}$ alkyl). In some embodiments, for example, when A1 is phenyl, A1 is substituted at the para position.

Each ring A for Structural Formulas (XXV), (XXIX), (XXX) and (XXXIV) independently and optionally is substituted with one or more substituents. Suitable substituents include halogen, $Ak^1$, —$OR^{10}$ and —$SR^{10}$. Preferred substituents for each ring A include halogen, $C_{1-15}$ alkyl; $C_{1-15}$ haloalkyl; —$C_{2-10}$ alkynylene-($C_{1-10}$ alkyl); —$C_{2-10}$ alkynyl, —$C_{1-10}$ alkylene-$N(R^{21})_2$, —$C_{1-10}$ alkylene-O—$C_{1-5}$ alkyl; —$C_{1-10}$ alkylene-S—$C_{1-5}$ alkyl, —$OC_{1-10}$ alkyl, and —$SC_{1-10}$ alkyl. In some preferred embodiments, A is monosubstituted (e.g., with $C_{1-10}$ alkyl). In some embodiments, for example, when A is phenyl, A is substituted at the para position.

Each $R^1$ independently is —OH or —$OC_{1-6}$ alkyl. Preferably, $R^1$ is —OH, —$OCH_3$ or —$OC_2H_5$.

Each $R^4$ and $R^5$ independently is $C_1$-$C_6$ alkyl. Preferably, each $R^4$ and $R^5$ independently is —$CH_3$. In some embodiments, one or $R^4$ or $R^5$ is H and the other of $R^4$ or $R^5$ is $C_{1-6}$ alkyl (e.g., —$CH_3$).

Each 10 independently is i) a $C_{1-10}$ aliphatic group optionally substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$, —$N(R^{26})_2$, —$NR^{26}C(O)R^{25}$, —$NR^{26}C(O)$-$Ak^0$-$Ar^0$, —$C(O)R^{25}$, —$C(O)$-$Ak^0$-$Ar^0$, —$CO_2R^{25}$, —$CO_2$-$Ak^0$-$Ar^0$ and —$C(O)N(R^{26})_2$—; or ii) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl.

Each $R^{25}$ independently is i) hydrogen, ii) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or iii) a $C_{1-10}$ alkyl group optionally substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy.

Each $R^{26}$ independently is $R^{25}$, —$CO_2R^{25}$, —$SO_2R^{25}$ or —$C(O)R^{25}$, or —$N(R^{26})_2$ taken together is an optionally substituted non-aromatic heterocyclic group. The non-aromatic heterocyclic group represented by —$N(R^{26})_2$ is optionally substituted with one or more substituents selected from the group consisting of halogen, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, nitro, cyano, hydroxy, $C_{1-10}$ alkoxycarbonyl, $C_{1-10}$ alkylcarbonyl, $C_{1-10}$ haloalkoxy, ($C_{1-6}$ haloalkoxy)$C_{1-10}$ alkyl, $C_{1-10}$ haloalkyl, $C_{6-14}$ aryl and 5-14 membered heteroaryl.

Each $Ak^0$ independently is a C1-C10 alkylene group.

Each $Ak^1$ independently is optionally substituted with one or more substituents selected from the group consisting of halogen, —$Ar^2$, —$OR^{20}$, —O-$Ak^2$-$Ar^2$, —$SR^{20}$, —S-$Ak^2$-$Ar^2$, —$N(R^{21})_2$, —$NR^{21}C(O)R^{20}$, —$NR^{21}C(O)$-$Ak^2$-$Ar^2$, —$C(O)R^{20}$, —C(O)-$Ak^2$-Ar, —$C(S)R^{20}$, —C(S)-$Ak^2$-Ar, —$CO_2R^{20}$, —$CO_2$-$Ak^2$-$Ar^2$, —OC(O)—$R^{20}$, —OC(O)-$Ak^2$-$Ar^2$, —$C(O)N(R^{21})_2$—, —$S(O)_2R^{22}$, —$S(O)_2$-$Ak^2$-$Ar^2$, —$SO_2N(R^{21})_2$, —$SO_2N(R^{21})$—$NR^{21}$, —$S(O)R^{22}$, —S(O)-$Ak^2$-$Ar^2$, —$NR^{21}SO_2R^{22}$ and —$NR^{21}SO_2$-$Ak^2$-$Ar^2$.

Values and preferred values for the remainder of the variables of Structural Formulas (XIX)-(XXXIV) are as described above for the first set of values for the variables of Structural Formula (I).

A second set of values for the variables of Structural Formulas (XIX)-(XXXIV) is provided in the following paragraphs:

Each $R^4$ and $R^5$ independently is —$CH_3$. In some embodiments, one of $R^4$ or $R^5$ is H and the other of $R^4$ or $R^5$ is —$CH_3$.

Each of $X^-$, $R^1$, $R^{10}$, $R^{25}$, $Ak^0$, $Ak^1$, t, k, r and s independently is as described above in the first set of values for the variables of Structural Formulas (XIX)-(XXXIV).

Suitable substituents for each of rings A and A1, are independently as described above in the first set of values for the variables of Structural Formulas (XIX)-(XXXIV).

Values and preferred values for the remainder of the variables of Structural Formulas (XIX)-(XXXIV) are as described above for the first set of values for the variables of Structural Formula (I).

A third set of values for the variables of Structural Formulas (XIX)-(XXXIV) is provided in the following paragraphs:

Each t for Structural Formulas (XIX), (XX), (XXI), (XXII), (XXIII), (XXIV), (XXVI), (XXVII), (XXVIII), (XXXI), (XXXII) and (XXXIII) independently is 1, 2, 3, 4, 5, 6, 7, 8, 9 or 10. Preferably, each t independently is 6, 7, 8, 9 or 10.

Each k for Structural Formulas (XIX)-(XXIX) independently is 1 or 2.

Each of r and s for Structural Formulas (XXXI)-(XXXIV) independently is 0, 1, or 2, provided that the sum of r and s is 1 or 2.

Each of $R^1$, $R^4$ and $R^5$ independently is as defined in the first set, the second set, or the third set of values for the variables of Structural Formula (I).

Suitable substituents for each ring A independently are as described above for the aryl group represented by $R^2$ of Structural Formula (I).

Suitable substituents for each ring A1 independently are as described above for the aryl group represented by $R^{20}$ of Structural Formula (I).

Specific examples of the compounds of the invention include compounds shown in Table 1 and those exemplified in the examples below, stereoisomers thereof, and pharmaceutically acceptable salts thereof.

It is to be understood that when any compound is referred to herein by name or structure, solvates, hydrates and polymorphs thereof are included.

The compounds of the invention may contain one or more chiral center and/or double bond and, therefore, exist as stereoisomers, such as double-bond isomers (i.e., geometric isomers), enantiomers, or diastereomers. When compounds of the invention are depicted or named without indicating the stereochemistry, it is to be understood that both stereomerically pure forms (e.g., geometrically pure, enantiomerically pure, or diastereomerically pure) and stereoisomeric mixtures are encompassed. For example, some compounds represented by Structural Formula (I) below have chiral center a. Accordingly, the compounds of the invention depicted by Structural Formula (I), having a chiral center, include the pure R stereo isomer, the pure S stereoisomer, and mixtures thereof.

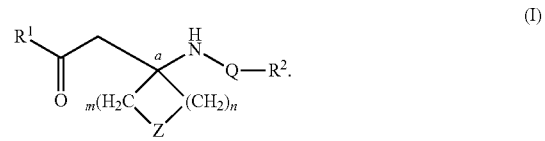

(I)

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures, and diastereomeric mixtures of the compounds of the invention.

In some preferred embodiments, when the compounds of the invention have chiral center a, then the compounds have R stereo chemistry at the chiral center a.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds of the invention that comprise a quaternary ammonium group and a carboxylic acid group may, upon reaction with a pharmaceutically acceptable base, form as zwitterion as shown in the structure below:

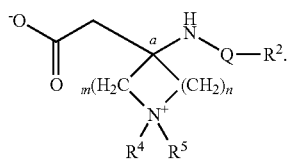

Such zwitterions are encompassed within the term "pharmaceutically acceptable salt", as the term is used herein. One skilled in the art understands that when a compound of the invention is in the zwitterionic form, the carboxylate anion corresponds to $X^-$ in the structural formulas depicted herein.

Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

The term "halo" as used herein means halogen and includes chloro, fluoro, bromo and iodo.

An "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between about one and about twenty carbon atoms, typically between about one and about ten carbon atoms, more typically between about one and about six carbon atoms. When cyclic, an aliphatic group typically contains between about three and about ten carbon atoms, more typically between about three and about seven carbon atoms. A "substituted aliphatic group" is substituted at any one or more "substitutable carbon atom". A "substitutable carbon atom" in an aliphatic group is a carbon in an aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms. Suitable substituents on a substitutable carbon atom of an aliphatic group are the same as those for an alkyl group.

The term "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, includes as used herein means saturated straight-chain, cyclic or branched aliphatic group. As used herein, a $C_1$-$C_6$ alkyl group is referred to "lower alkyl." Similarly, the terms "lower alkoxy", "lower haloalkyl", "lower arylalkyl", "lower alkylamine", "lower cycloalkylalkyl", "lower dialkyamine", "lower alkylamino", "lower dialkyamino" "lower alkylcarbonyl", "lower alkoxycarbonyl" include straight and branched saturated chains containing one to six carbon atoms.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkyamine" means amine substituted with two alkyl groups; "alkylcarbonyl" means —C(O)—R, wherein R is alkyl; "alkoxycarbonyl" means —C(O)—OR, wherein R is alkyl; and where alkyl is as defined above.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "acyl group" mean —C(O)R, wherein R is an optionally substituted alkyl group or aryl group (e.g., optionally substituted phenyl). R is preferably an unsubstituted alkyl group or phenyl.

An "alkylene group" is represented by —[$CH_2$]$_z$—, wherein z is a positive integer, preferably from one to eight, more preferably from one to four.

An "alkenylene group" is an alkylene in which at least a pair of adjacent methylenes are replaced with —CH=CH—.

An "alkynylene group" is an alkylene in which at least a pair of adjacent methylenes are replaced with —C≡C—.

The term "aryl group" used alone or as part of a larger moiety as in "aralkyl", "aralkoxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has six-fourteen ring atoms. A "substituted aryl group" is substituted at any one or more substitutable ring atom. The term "$C_{6-14}$ aryl" as used herein means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to aromatic ring groups having five to fourteen ring atoms selected from carbon and at least one (typically 1-4, more typically 1 or 2) heteroatom (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N. NH, N($C_{1-6}$ alkyl), O and S and includes thienyl, furyl, pyrrolyl, pyrididyl, indolyl, quinolyl, isoquinolyl, tetrahydroquinolyl, benzofuryl, benzothienyl and the like.

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl(e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteraryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

Other examples for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

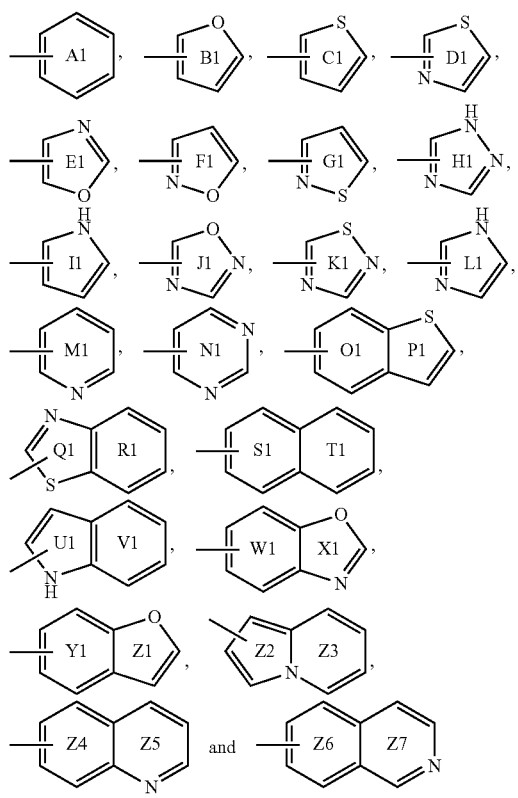

wherein each of rings A1-Z7 is optionally substituted. It is noted that, as shown above, rings O1-Z7 can be attached to their designated atom through any ring carbon of the rings which is not at a position bridging two aryl groups. For example,

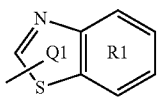

means that the group is attached to its designated atom through either ring Q1 or ring R1. Yet other examples for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

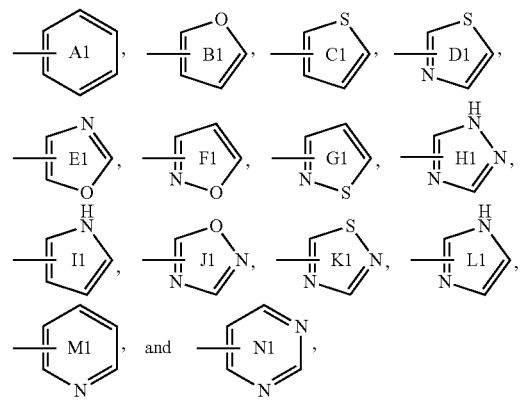

wherein each of rings A1-N1 is optionally substituted. More specific values for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

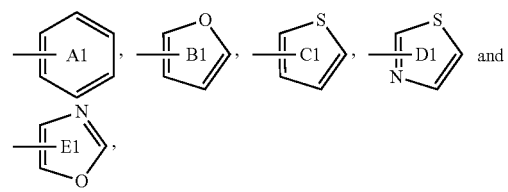

wherein each of rings A1-E1 is optionally substituted. Even more specific values for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

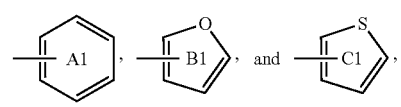

wherein each of rings A1-C1 is optionally substituted. An optionally substituted ring A is the most common specific value for each of the aryl group, including the $C_{6-14}$ aryl group represented by $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$.

The aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, can be optionally substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkyl amino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl. Specific substituents for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy$)C_{1-10}$ alkyl, $C_{1-10}$ haloalkoxy, $(C_{1-6}$ haloalkoxy$)C_{1-10}$ alkyl and $C_{1-10}$ haloalkyl. More specific substituents include $C_{1-10}$ alkyl, —OH, $C_{1-10}$ alkoxy, haloalkyl, halogen, $C_{1-10}$ haloalkoxy, amino, nitro and cyano.

In accordance with another aspect of the present invention, the compounds of the invention can be prepared by processes analogous to those established in the art.

By way of illustration, compounds of Formula (I), wherein Q-$R^2$ is C(O)—$R^2$, and m, n, $R^2$, $R^4$ and $R^5$ are as defined in Formula (I), may be prepared by the methods outlined in Scheme 1. A suitable cyclic ketone, as defined by Formula 2, wherein m and n are as defined in Formula (I), R' is a $C_{1-6}$alkyl group or a nitrogen protecting group, is reacted with a 3-alkoxy-3-oxopropanoic acid in the presence of an ammonia source such as ammonium acetate to yield compounds of Formula 3. At this stage compounds of Formula 3, wherein $R^1$ is $C_{1-6}$alkyl, may be optionally converted to compounds of Formula 3 wherein $R^1$ is O$^-$ or OH.

Reaction of compounds of Formula 3, wherein m, n and $R^1$ are as defined in Formula (I) and R' is a $C_{1-6}$alkyl group (R'=$R^4$) or a nitrogen protecting group (R'=P), with a suitable acylating reagent of Formula 6 ($R^2$ is as defined in Formula (I) and LG is a suitable leaving group), such as an activated ester, an acyl chloride, an acyl imidazole or a mixed anhydride, is carried out in an organic solvent in the presence of an organic base such as a tertiary amine. In another aspect of the invention the acylating reagent 6, may be generated in situ for example from a carbodiimide prior to reaction with compounds of Formula 3.

may be removed by hydrogenolysis or a t-butyloxycarbonyl protecting group may be removed by acid hydrolysis. In the case where R' of the reacting substrate 3 is an $C_{1-6}$ alkyl group the product of the acylation reaction will yield compounds of Formula (I) wherein the ring nitrogen is a tertiary amine. An alternate method for the preparation of compounds of Formula (I) wherein the ring nitrogen is a tertiary amine involves the reductive amination of compounds of Formula (I) wherein the ring nitrogen is a secondary amine, by treatment with an aldehyde 8 and a reducing agent such as sodium borohydride.

Compounds of Formula (I) wherein the ring nitrogen is a secondary amine may be converted to compounds of Formula (I) wherein the ring nitrogen is quaternized with two identical substituents (i.e. $R^4$=$R^5$) by treatment with excess alkylating agent 7 such as an alkyl halide or an alkyl sulfonate. Alternatively compounds of Formula (I) wherein the ring nitrogen is a tertiary amine may be converted to compounds of Formula (I) wherein the ring nitrogen is quaternized with two identical or two different substituents by treatment with alkylating agent 7 such as an alkyl halide or an alkyl sulfonate.

In the case where the reacting substrate is an acid, then acid compounds of Formula (I), wherein $R^1$ is O$^-$ or OH, are obtained directly, whereas if the substrate is an ester then compounds of Formula (I), wherein $R^1$ is $C_{1-6}$ alkyl are obtained directly and a subsequent hydrolysis step generates the acid, wherein $R^1$ is O$^-$ or OH.

Scheme 1

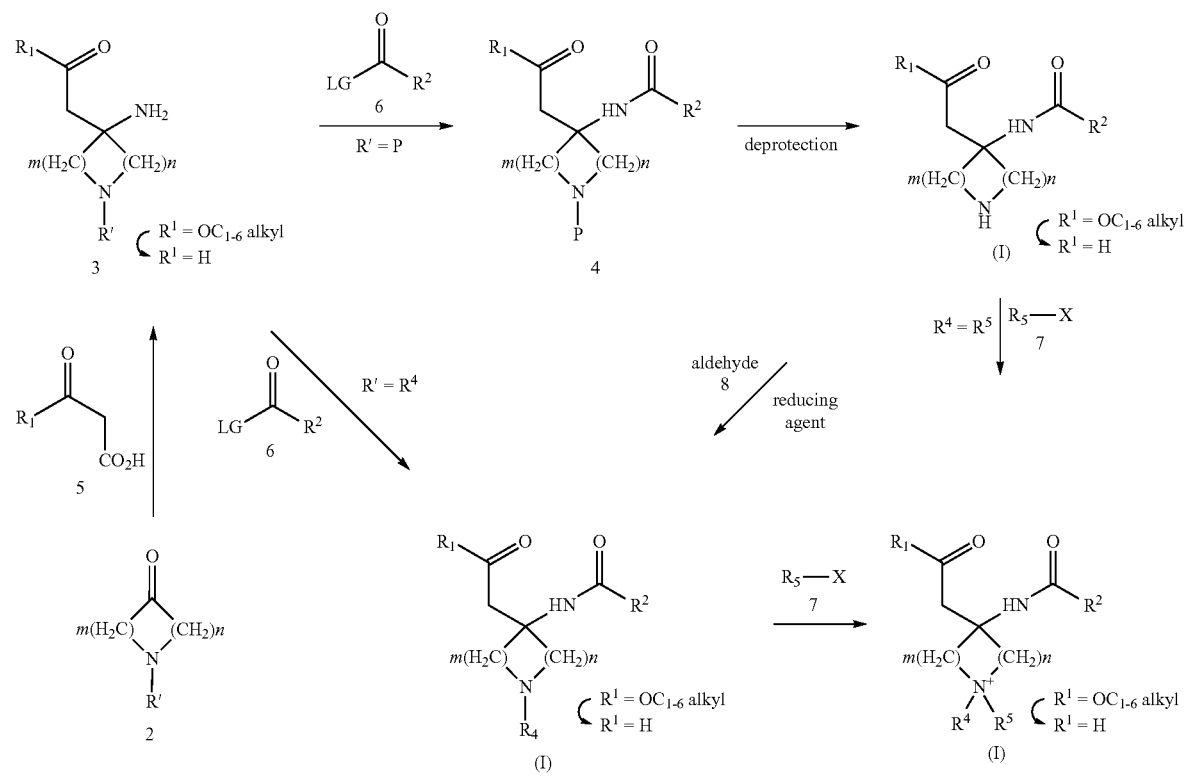

In the case where R' of the reacting substrate 3 is a nitrogen protecting group the product of the acylation reaction 4 may be converted to the compounds of Formula (I) wherein the ring nitrogen is a secondary amine by a subsequent deprotection step. For example a benzyloxycarbonyl protecting group Compounds of Formula (I), wherein Q-$R^2$ is $SO_2$—$R^2$ and m, n, $R^2$, $R^4$ and $R^5$ are as defined in Formula (I), may be prepared, for example, by the methods outlined in Scheme 2. Reaction of compounds of Formula 3, (wherein $R^1$ is a protecting group, $R^2$ is as defined in Formula (I)), with a suitable sulfonylating agent 9 such as sulfonyl halide (LG=Br, Cl, F) or an activated sulfonate ester (LG=$OC_6F_5$, $OC_6H_4$-$pNO_2$), affords the compounds of Formula 10 wherein P is a protecting group. Deprotection of compounds of Formula 10 yields compounds of Formula (I) wherein the ring nitrogen is a secondary amine. Subsequent alkylation with two or more equivalents of alkylating reagent 7 such as an alkyl halide or sulfonate yields compounds of Formula (I), wherein the ring nitrogen is a quaternary ammonium salt.

Compounds of Formula (I) wherein the ring nitrogen is a secondary amine may be converted to compounds of Formula (I) wherein the ring nitrogen is a tertiary amine by a reductive amination procedure employing an aldehyde 8 and a reducing agent such as sodium borohydride. Alternatively, compounds of Formula (I) wherein the ring nitrogen is a tertiary amine (R'=$C_{1-6}$alkyl) may also be prepared directly from compounds of Formula 3 wherein the ring nitrogen is a tertiary amine (R'=$C_{1-6}$ alkyl) by reaction with a suitable sulfonylating agent 9 such as sulfonyl halide (LG=Br, Cl, F) or an activated sulfonate ester (LG=$OC_6F_5$, $OC_6H_4$-$pNO_2$).

Compounds of Formula (I) wherein the ring nitrogen is a tertiary amine may be converted to compounds of Formula (I) wherein the ring nitrogen is a quaternary amminium salt by treatment with an alkylating agent 7 such as an alkyl halide or an alkyl sulfonate.

In the case where the reacting substrate is an acid, then acid compounds of Formula (I), wherein $R^1$ is $O^-$ or OH, are obtained directly, whereas if the substrate is an ester then compounds of Formula (I), wherein $R^1$ is $C_{1-6}$alkyl are obtained directly and a subsequent hydrolysis step generates the acid, wherein $R^1$ is $O^-$ or OH.

or derivatives thereof (wherein R' is as defined in Formula (I) and R' is small alkyl $R^4$ or a protecting group P) with an isocyanate (11, Y=O) or thioisocyanate (11, Y=S) yields the urea or thiourea. In the case where the reacting substrate is a compound wherein the ring nitrogen is bonded to a protecting group (R'=P), then subsequent deprotection of compounds of Formula 12 yields compounds of Formula (I) wherein the ring nitrogen is a secondary amine. Subsequent alkylation with two or more equivalents of alkylating reagent 7 such as an alkyl halide or sulfonate yields compounds of Formula (I), wherein the ring nitrogen is a quaternary ammonium salt.

Compounds of Formula (I) wherein the ring nitrogen is a secondary amine ($R^4$=H, Y=S or O) may be converted to compounds of Formula (I) wherein the ring nitrogen is a tertiary amine by a reductive amination procedure employing an aldehyde 8 and a reducing agent such as sodium borohydride. Alternatively, compounds of Formula (I) wherein the ring nitrogen is a tertiary amine (R'=$C_{1-6}$alkyl) may also be prepared directly from compounds of Formula 3 wherein the ring nitrogen is a tertiary amine (R'=$C_{1-6}$ alkyl) by treatment with an isocyanate (11, Y=O) or thioisocyanate (11, Y=S) to yields the urea or thiourea.

Compounds of Formula (I) wherein the ring nitrogen is a tertiary amine may be converted to compounds of Formula (I) wherein the ring nitrogen is a quaternary amminium salt by treatment with an alkylating agent 7 such as an alkyl halide or sulfonate.

Conversion of compounds of Formula (I) wherein said compound is a thiourea to the corresponding urea may be accomplished through an additional oxidation step with a reagent such as manganese dioxide or 35% hydrogen perox- Scheme 2

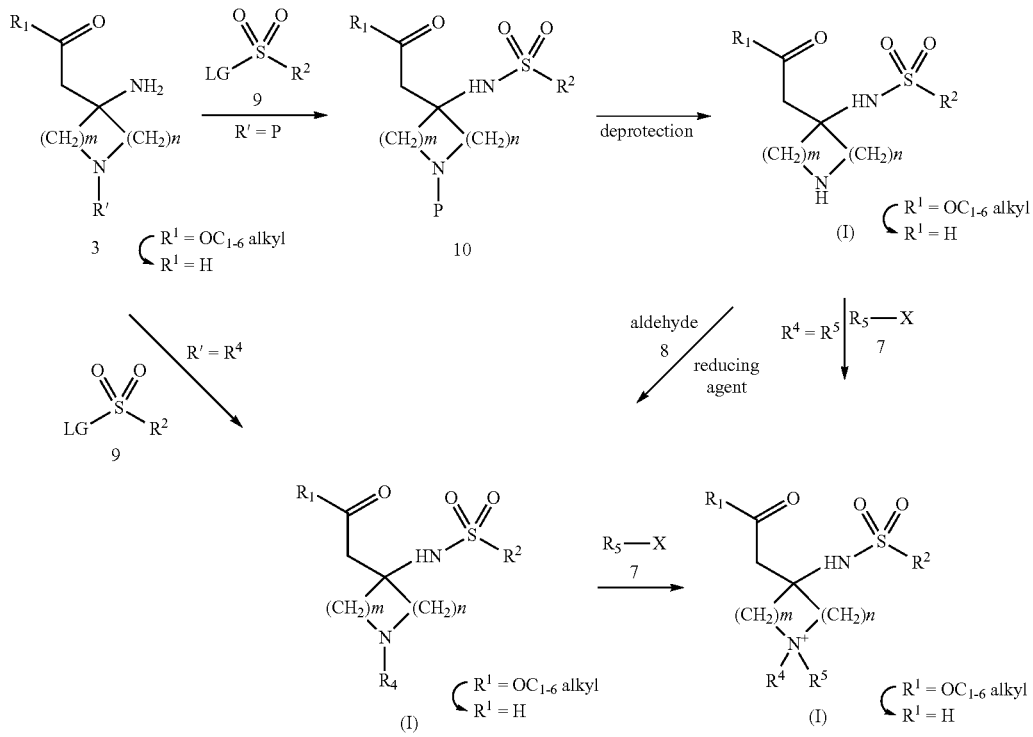

Compounds of Formula (I), wherein Q-$R^4$ is C(O)—NH—$R^4$ or C(S)—NH—$R^4$ and m, n, $R^2$, $R^4$ and $R^5$ are as defined in Formula (I), may be prepared, for example, by the methods outlined in Scheme 3. Reaction of compounds of Formula 3 ide. In the case where the reacting substrate for a given transformation is an acid, then acid compounds of Formula (I), wherein $R^1$ is $O^-$ or OH, are obtained directly, whereas if the substrate is an ester then compounds of Formula (I), wherein $R^1$ is $C_{1-6}$alkyl are obtained directly and a subsequent hydrolysis step generates the acid, wherein $R^1$ is $O^-$ or OH.

then the product of the sulfamating reaction is a compound of Formula (I) wherein the ring nitrogen is a tertiary amine

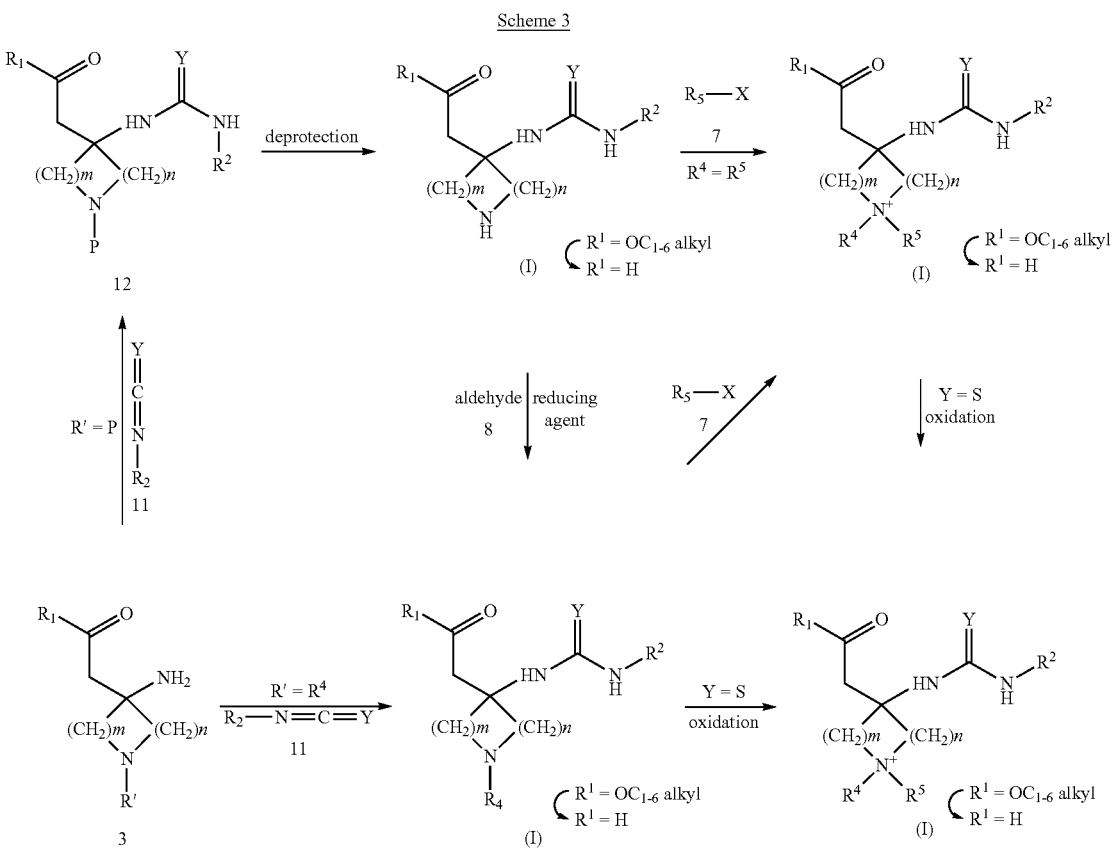

Scheme 3

Compounds of Formula (I), wherein Q-$R^4$ is $SO_2NR^4R^5$ and m, n, $R^2$, $R^4$ and $R^5$ are as defined in Formula (I) may be prepared, for example, by the methods outlined in Scheme 4. Compounds of Formula 3, (wherein R' is as defined in Formula (I) and R' is small alkyl i.e. $R^4$ or a protecting group P) may be reacted with a sulfamylating reagent such as 13 wherein $R^2$ and is as defined above and LG is a suitable leaving group, for example 2-oxooxazolidine-3-yl, 2-chloroethylcarbamoyl, Cl or imidazolium. In the case wherein the reacting substrate is a compound wherein the ring nitrogen is bonded to a protecting group (R'=P), then subsequent deprotection of compounds of Formula 14 yields compounds of Formula (I) wherein the ring nitrogen is a secondary amine. Subsequent alkylation with two or more equivalents of alkylating reagent 7 such as an alkyl halide or alkyl sulfonate yields compounds of Formula (I), wherein the ring nitrogen is a quaternary ammonium salt.

When the reacting substrate is a compound of Formula 3 wherein the ring nitrogen is a tertiary amine ($R^4=C_{1-6}$alkyl) ($R^4=C_{1-6}$alkyl). Alternatively, Compounds of Formula (I) wherein the ring nitrogen is a tertiary amine can be obtained from compounds of Formula (I) wherein the ring nitrogen is a secondary amine by a reductive amination procedure employing an aldehyde 8 and a reducing agent such as sodium borohydride.

Compounds of Formula (I) wherein the ring nitrogen is a tertiary amine may be converted to compounds of Formula (I) wherein the ring nitrogen is a quaternary amminium salt by treatment with an alkylating agent 7 such as an alkyl halide or sulfonate.

In the case where the reacting substrate for a given transformation is an acid, then acid compounds of Formula (I), wherein $R^1$ is $O^-$ or OH, are obtained directly, whereas if the substrate is an ester then compounds of Formula (I), wherein $R^1$ is $C_{1-6}$alkyl are obtained directly and a subsequent hydrolysis step generates the acid, wherein $R^1$ is $O^-$ or OH.

Scheme 4

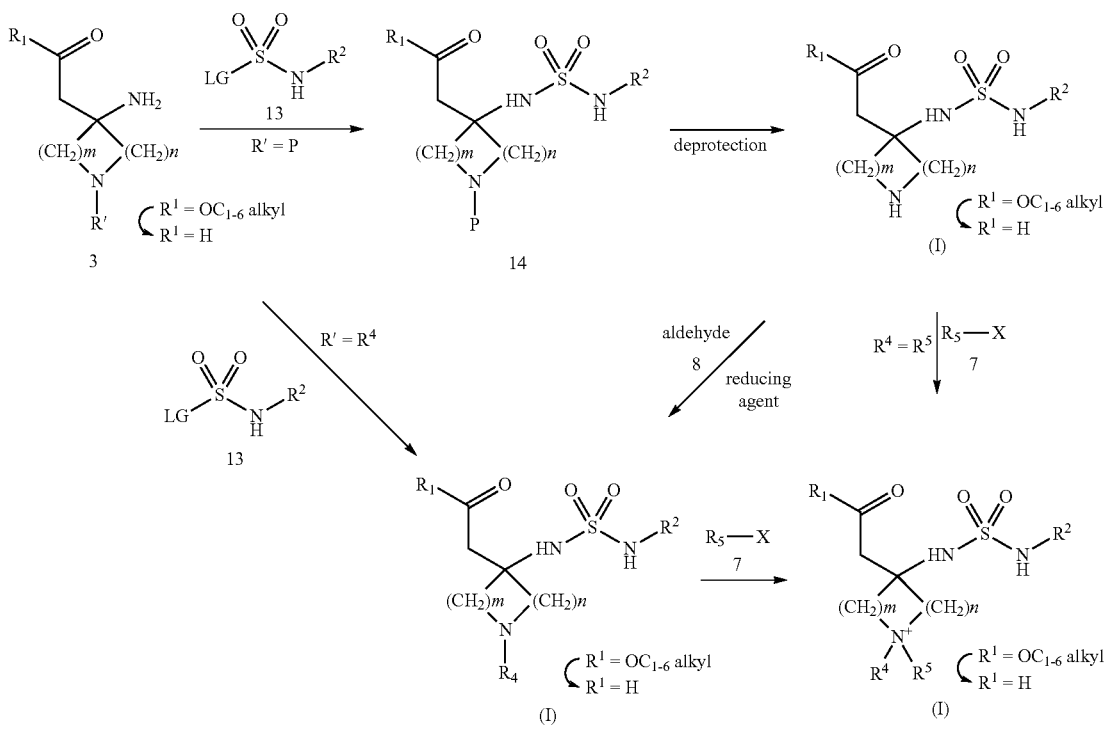

Compounds or substrates of Formula 3 include acids and alkyl esters thereof and derivatives, which include various salts thereof. Such compounds may be prepared using methods known in the art or described herein.

The methods described above can result in the formation of the corresponding free acid and/or free amine or one or both of the corresponding salts thereof. This will depend on the reaction conditions and final isolation procedures as would be known to a person skilled in the art. The formation of, or transformation to, a desired compound salt is achieved using standard techniques. For example, the neutral compound is treated with an acid or base in a suitable solvent and the formed salt is isolated by filtration, extraction or any other suitable method The methods described above can result in the formation of the corresponding free acid and/or free amine or one or both of the corresponding salts thereof. This will depend on the reaction conditions and final isolation procedures as would be known to a person skilled in the art. The formation of, or transformation to, a desired compound salt is achieved using standard techniques. For example, the neutral compound is treated with an acid or base in a suitable solvent and the formed salt is isolated by filtration, extraction or any other suitable method. In a particular example, quaternization of the compounds of Formula (I), wherein Z is $NR^4$, wherein $R^4$ is $C_{1-6}$alkyl, may be performed by reacting a compound of Formula (I) with a $C_{1-6}$alkyl halide, to yield compounds of Formula (I), wherein Z is a trialkylamminium. If $R^1$ is a ester, subsequent ester hydrolysis yields the acid compounds of Formula (I), where $R^1$ is $O^-$ or OH.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

The present invention includes radiolabeled forms of the compounds of the invention, for example, compounds of the invention labeled by incorporation within the structure of $^3$H, $^{11}$C or $^{14}$C or a radioactive halogen such as $^{125}$I and $^{18}$F. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo-, suitably iodo-, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the invention containing a radioactive fluorine may be prepared, for example, by reaction of K[$^{18}$F]/K222 with a suitable precursor compound, such as a compound of Formula I comprising a suitable leaving group, for example a tosyl group, that may be displaced with the $^{18}$F anion.

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T.

W. and Wuts, P. G. M., "Protective Groups in Organic Synthesis", John Wiley & Sons, 3$^{rd}$ Edition, 1999.

In some embodiments, i) when Q is —C(=O)—, —C(=S)—, —C(O)NH—, —C(S)NH— or —S(O)$_2$—, and each of n and m is 2, then $R^2$ is not a C3-C7 alkyl group substituted with a substituted phenoxy group, and/or ii) when Q is —C(=O)— and $R^2$ is a substituted or unsubstituted phenyl, and when one of n and m is 1 and the other of n and m is 2, or each of n and m is 2, then Z is —N$^+$($R^4R^5$)X$^-$—. In these embodiments, particularly when Q is —C(=O)—, —C(=S)—, —C(O)NH—, —C(S)NH— or —S(O)$_2$—, and each of n and m is 2, then i) $R^2$ is not a C$_3$-C$_7$ alkyl group substituted with an optionally substituted phenoxy group, ii) $R^2$ is not a substituted C3-C7 alkyl group; iii) $R^2$ is not an alkyl group substituted with an optionally substituted aryloxy group, or iv) $R^2$ is not a substituted alkyl group.

In other embodiments, the compound of the invention is represented by Structural Formula (I), or a pharmaceutically acceptable salt thereof, wherein when Q is —C(=O)—, —C(O)NH— or —C(=O)—N($R^3$)—, then each of $R^2$ and $R^3$ independently is not a substituted or unsubstituted, six-membered N-containing heteroaryl group.

In yet other embodiments, the compound of the invention is represented by Structural Formula (I), or a pharmaceutically acceptable salt thereof, wherein: i) when Q is —C(=O)— or —C(O)NH—, and when each of n and m is 2, then $R^2$ is not an unsubstituted C1-C3 alkyl group; ii) when Q os —C(=O)—N($R^3$)—, and when each of n and m is 2, then each of $R^2$ and $R^3$ is not —CH$_3$; and iii) when Q is —S(O)$_2$—, or —S(O)$_2$—NH—, and when each of n and m is 2, then $R^2$ is not —CH$_3$.

In yet some other embodiments, the compound of the invention is represented by Structural Formula (I), or a pharmaceutically acceptable salt thereof, wherein: i) when Q is —C(=O)—, —C(O)NH— or —C(=O)—N($R^3$)—, then each of $R^2$ and $R^3$ independently is not a substituted or unsubstituted, six-membered N-containing heteroaryl group; ii) when Q is —C(=O)— or —C(O)NH—, and when each of n and m is 2, then $R^2$ is not an unsubstituted C1-C3 alkyl group; iii) when Q os —C(=O)—N($R^3$)—, and when each of n and m is 2, then each of $R^2$ and $R^3$ is not —CH$_3$; and iv) when Q is —S(O)$_2$—, or —S(O)$_2$—NH—, and when each of n and m is 2, then $R^2$ is not —CH$_3$.

In yet some other embodiments, the compound of the invention is represented by a formula selected from Structural Formulas (I) and (XVIII), or a pharmaceutically acceptable salt thereof, wherein: i) each of $R^2$ and $R^3$ independently is not a substituted or unsubstituted, six-membered N-containing heteroaryl group; ii) when each of n and m for Structural Formula (I) independently is 2, or when each of r and s for Structural Formulas (III)-(X) is independently 1, then each $R^2$ is not a substituted C3-C7 alkyl group; and/or iii) when each of n and m for Structural Formula (I) independently is 2, or when each of r and s for Structural Formulas (III)-(X) is independently 1, then each $R^2$ is not an unsubstituted C1-C3 alkyl group. In yet some other embodiments, the compound of the invention is represented by a formula selected from Structural Formulas (I) and (XVIII), or a pharmaceutically acceptable salt thereof, wherein: i) each of $R^2$ and $R^3$ independently is not a substituted or unsubstituted, six-membered N-containing heteroaryl group; and ii) when each of n and m for Structural Formula (I) independently is 2, or when each of r and s for Structural Formulas (III)-(X) is independently 1, then each $R^2$ is not a substituted C3-C7 alkyl group. In yet some other embodiments, the compound of the invention is represented by a formula selected from Structural Formulas (I) and (XVIII), or a pharmaceutically acceptable salt thereof, wherein: i) each of $R^2$ and $R^3$ independently is not a substituted or unsubstituted, six-membered N-containing heteroaryl group; and ii) when each of n and m for Structural Formula (I) independently is 2, or when each of r and s for Structural Formulas (III)-(X) is independently 1, then each $R^2$ is not an unsubstituted C1-C3 alkyl group. In yet some other embodiments, the compound of the invention is represented by a formula selected from Structural Formulas (I) and (XVIII), or a pharmaceutically acceptable salt thereof, wherein: i) when each of n and m for Structural Formula (I) independently is 2, or when each of r and s for Structural Formulas (III)-(X) is independently 1, then each $R^2$ is not a substituted C3-C7 alkyl group; and ii) when each of n and m for Structural Formula (I) independently is 2, or when each of r and s for Structural Formulas (III)-(X) is independently 1, then each $R^2$ is not an unsubstituted C1-C3 alkyl group.

Carnitine palmitoyl transferase 1 (CPT1A and CPT1C) has been implicated in growth and survival of cancer cells. Thus, small molecule inhibitors of these enzymes are potential anti-tumor agents. Several compounds disclosed herein have been synthesized that have IC$_{so}$ values against CPT1 in the low µM range in a biochemical assay.

The compounds of Formula (I) are CPT1 inhibitors and are useful in inhibiting CPT1 activity for the treatment of various conditions such as cancers. Accordingly, the present invention includes a method of treating a disease which benefits from an inhibition of CPT1 activity comprising administering an effective amount of a compound of the invention to a subject in need thereof. The present invention also includes the use of a compound of the invention to treat a disease which benefits from an inhibition of CPT1 activity and a use of a compound of the invention to prepare a medicament to treat a disease which benefits from an inhibition of CPT1 activity. In an embodiment, CPT1 is CPT1A and/or CPT1C. In yet another embodiment of the invention the disease which benefits from an inhibition of CPT1, suitably CPT1A and/or CPT1C, activity is cancer.

The present invention therefore includes a method of treating cancer comprising administering an effective amount of a compound represented by Structural Formula (I), or pharmaceutically acceptable salt thereof, to a subject in need thereof. In an embodiment, the cancer is one that depends on CPT1A and/or CPT1C for tumor cell survival. In a further embodiment, the cancer is one that depends on CPT1A and/or CPT1C for tumor cell survival under hypoxic conditions. In another embodiment, the cancer is selected from the group consisting of lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In a preferred embodiment, the cancer is selected from the group consisting of lung cancer, colon cancer, brain cancer, neuroblastoma, prostate cancer, melanoma, glioblastoma mutiform and ovarian cancer. In another preferred embodiment, the cancer is selected from one or more of lung cancer, breast cancer, colon cancer, brain cancer, neuroblastoma, prostate cancer, melanoma, glioblastoma multiform and ovarian cancer.

The invention further relates to a method of treating tumor cells in a subject in need thereof, comprising administering to the subject, an amount of a compound disclosed herein that is effective to reduce the effective amount of CPT1A and/or CPT1C in the subject.

The invention further includes a method for treating tumor cells in a subject suffering from a cancer that expresses CPT1A and/or CPT1C in amounts higher that in normal tissue of the same type, comprising administering to the subject a compound disclosed herein in an amount that is effective to inhibit expression of CPT1A and/or CPT1C in the tumor cells and/or to increase apoptosis in the tumor cells.

The invention still further includes a method for treating tumor cells in a subject suffering from a cancer that depends on CPT1A and/or CPT1C for survival under hypoxic conditions, comprising administering to the subject an amount of a compound disclosed herein that is effect to inhibit expression of CPT1A and/or CPT1C by the tumor cells, increase apoptosis and/or reduce proliferation in the tumor cells.

The present invention also includes a method of treating diabetes of a subject in need thereof, by administering to the subject a therapeutically effective amount of a compound of the invention disclosed herein.

The compounds of the invention can also be used for treating a condition or disease of a subject in need thereof, wherein the condition or disease is a condition or disease mediated by metalloproteases, tumor necrosis factor, aggrecanase or a combination thereof. (see U.S. Pat. No. 6,495,565, and U.S. 2004/0072802, the teachings all of which are incorporated herein by reference) The condition or disease mediated by metalloproteases, tumor necrosis factor, aggrecanase is selected from the group consisting of inflammatory diseases, fever, acute infection and acute shock, and wherein the condition or disease mediated by Cholecystokinins is selected from the group consisting of: appetite disorders, pancreatic inflammation, pancreatic cancer, biliary tract diseases and Zollinger-Ellison syndrome. Specific examples include: septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteoarthritis, rheumatoid arthritis, multiple sclerosis, radiation damage, hyperoxic alveolar injury, periodontal disease, HIV and non-insulin dependent diabetes melitus The compounds of the invention can also be used for treating a condition or disease of a subject in need thereof, wherein the condition or disease is a condition or disease mediated by Cholecystokinins (See U.S. Pat. No. 5,847,125, the teachings of which are incorporated herein by reference). Specific examples of such diseases or conditions include appetite disorders, such as anorexia nervosa, pancreatic inflammation, pancreatic cancer, biliary tract diseases, Zollinger-Ellison syndrome, analgesia, opiate and various psychiatric disorders.

The compounds of the invention are suitably formulated into pharmaceutical compositions for administration to human subjects in a biologically compatible form suitable for administration in vivo. The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)).

The carriers, diluents and/or excipients are "acceptable" in the sense of being compatible with the other ingredients of the pharmaceutical composition and not deleterious to the recipient thereof.

In accordance with the methods of the invention, the described compounds of the invention, may be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of the invention, may be administered to an animal, suitably a human patient, alone or in combination with pharmaceutically acceptable carriers, as noted above, the proportion of which is determined by the solubility and chemical nature of the compound, chosen route of administration and standard pharmaceutical practice.

The compounds of the invention, can be formulated alone or for contemporaneous administration with other agents that inhibit CPT1 activity, or inhibit CPT1 activity and other targets, or in combination with other types of treatment (which may or may not modulate CPT1) for treating cancer. Therefore, according to yet another aspect of the present invention, there is included a pharmaceutical composition comprising one or more compounds selected from a compound of Formula I, and pharmaceutically acceptable salts thereof, and a pharmaceutically acceptable carrier, for the preparation of a medicament for the treatment of cancer to be used contemporaneously with another anti-cancer agent, for example, but not limited to a glucose metabolism inhibitor.

Typically, the pharmaceutical compositions of the invention can be administered before or after a meal, or with a meal. As used herein, "before" or "after" a meal is typically within two hours, preferably within one hour, more preferably within thirty minutes, most preferably within ten minutes of commencing or finishing a meal, respectively.

In one embodiment, the method of the present invention is a mono-therapy where the pharmaceutical compositions of the invention are administered alone. Accordingly, in this embodiment, the compound of the invention is the only pharmaceutically active ingredient in the pharmaceutical compositions.

In another embodiment, the method of the invention is a co-therapy with other therapeutically active drugs known in the art for treating the desired diseases or indications. In a specific embodiment, the compounds disclosed herein can be co-administered with one or more of other anticancer drugs known in the art. In another specific embodiment, the compounds disclosed herein can be co-administered with one or more of other agents that inhibit CPT1A and/or CPT1C activity. For example, but not limited to, the compounds of the invention are administered contemporaneously with glucose metabolism inhibitors (such as glycolysis inhibitors).

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. For example, in the context of inhibiting CPT1C and/or CPT1A, for example, it is an amount of the compound sufficient to achieve such an inhibition in CPT1C and/or CPT1A activity as compared to the response obtained without administration of the compound. In the context of disease, therapeutically effective amounts of the compounds of the present invention are used to treat, modulate, attenuate, reverse, or affect cancer in a subject. An "effective amount" is intended to mean that amount of a compound that is sufficient to treat, prevent or inhibit cancer disease associated with cancer. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces cancer (e.g., as determined by clinical symptoms or the amount of cancer cells) in a subject as compared to a control. As defined herein, a therapeutically effective amount of a compound of the present invention may be readily determined by one of ordinary skill by routine methods known in the art.

In an embodiment, a therapeutically effective amount of a compound of the present invention ranges from about 0.1 to about 15 mg/kg body weight, suitably about 1 to about 5 mg/kg body weight, and more suitably, from about 2 to about 3 mg/kg body weight. The skilled artisan will appreciate that certain factors may influence the dosage required to effectively treat a subject, or prevent a subject, suffering from cancer and these factors include, but are not limited to, the severity of the disease or disorder, previous treatments, the general health and/or age of the subject and other diseases present.

Moreover, a "treatment" or "prevention" regime of a subject with a therapeutically effective amount of the compound of the present invention may consist of a single administration, or alternatively comprise a series of applications. For example, the compound of the present invention may be administered at least once a week. However, in another embodiment, the compound may be administered to the subject from about one time per week to about once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with cancer or manifesting a symptom associated with cancer.

To "inhibit" or "suppress" or "reduce" a function or activity, such as ODCase activity, is to reduce the function or activity when compared to otherwise same conditions except for a condition or parameter of interest, or alternatively, as compared to another conditions.

The term "subject" or "patient" or synonym thereto, as used herein includes all members of the animal kingdom, especially mammals, including human. The subject or patient is suitably a human.

The term "CPT1" as used herein refers to CPT1A and/or CPT1C (see U.S. Provisional Application No. 60/893,649, filed Mar. 8, 2007, and U.S. Provisional Application No. 60/893,999, filed on Mar. 9, 2007).

The term "a cell" as used herein includes a plurality of cells. Administering a compound to a cell includes in vivo, ex vivo and in vitro treatment.

The invention is illustrated by the following examples which are not intended to be limiting in any way.

EXEMPLIFICATION

1: Synthesis of Compounds of the Invention

Preparation of Reactants and Reagents

Preparation 1. Ethyl 2-(4-amino-1-methylpiperidin-4-yl)acetate

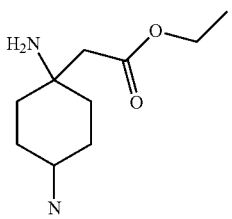

1-Methylpiperidin-4-one (4.8 mL, 41.6 mmol) was added drop-wise, under a nitrogen atmosphere, to a stirring, refluxing solution of 3-ethoxy-3-oxopropanoic acid (4.5 mL, 37.8 mmol) and NH$_4$OAc (4.1 g, 52.9 mmol) in EtOH (25 mL). The solution was stirred under reflux for 4 h and then cooled to room temperature. The EtOH was removed in vacuo and the residue transferred to a separatory funnel with EtOAc. The organic layer was washed 3× with 1M NaOH, 3× with Brine, and then dried (MgSO$_4$). The solvent was removed to give a yellow-orange oil which was purified by column chromatography (silica gel, 93:5:2 CH$_2$Cl$_2$/MeOH/7M NH$_3$ in MeOH) to give 3.3 g, 43% of a yellow oil.

$^1$H NMR (400 MHz, CDCl$_3$) δ 4.12 (q, 2H, J=6.8 Hz), 2.49-2.45 (m, 2H), 2.38 (s, 2H), 2.37-2.32 (m, 2H), 2.28 (s, 3H), 1.71-1.65 (m, 2H), 1.59-1.54 (m, 2H), 1.25 (t, 3H, J=6.8).); MS ESI 201.1 [M+H]$^+$, calcd for [C$_{10}$H$_{20}$N$_2$O$_2$+H]$^+$ 201.29.

Preparation 2. Methyl 2-(3-amino-1-methylpiperidin-3-yl)acetate

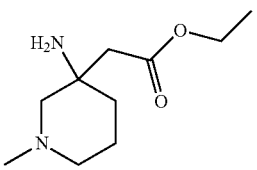

According to the method described in example 1, 1-Methylpiperidin-3-one is reacted with 3-methoxy-3-oxopropanoic acid and NH$_4$OAc in EtOH to yield the title compound.

Preparation 3. Benzyl 3-amino-3-(2-ethoxy-2-oxoethyl)pyrrolidine-1-carboxylate

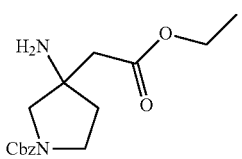 [SMILES: CCOC(=O)CC1(N)CCN(C(=O)OCc2ccccc2)C1]

A solution of benzyl 3-oxopyrrolidine-1-carboxylate (2.03 g, 10 mmol) and ammonium acetate (977 mg, 12.7 mmol) in EtOH (10 mL) was treated with ethyl malonate (1.07 mL, 9.09 mmol). The resulting solution was heated to reflux for 4 h and cooled to room temperature. Ethyl acetate (200 mL) was added and the solution was washed with saturated NaHCO$_3$ (25 mL), brine (25 mL), dried over MgSO$_4$ and concentrated to dryness. The mixture was filtered through a silica gel plug with ethyl acetate followed by methanol to elute the title compound as a yellow oil (600 mg, 19%). $^1$H NMR (400 MHz, CD$_3$OD) δ 7.40-7.32 (m, 5H), 4.23 (q, 2H, J=7.4 Hz), 3.81-3.76 (m, 1H), 3.66-3.56 (m, 3H), 2.94 (s, 2H), 2.29-2.24 (m, 2H), 1.29 (t, 3H, J=7.4 Hz). MS ESI 307.1 [M+H]$^+$, calcd for [C$_{16}$H$_{22}$N$_2$O$_4$+H]$^+$ 307.16.

Preparation 4. tert-Butyl 3-amino-3-(2-ethoxy-2-oxoethyl)azetidine-1-carboxylate

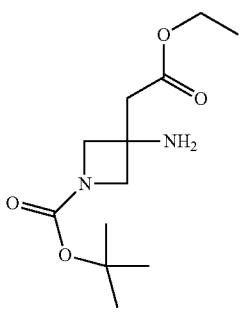 [SMILES: CCOC(=O)CC1(N)CN(C(=O)OC(C)(C)C)C1]

t-Butyl 3-oxoazetidine-1-carboxylate (1.0 g, 5.84 mmol) was added portion-wise, under a nitrogen atmosphere, to a refluxing solution of 3-ethoxy-3-oxopropanoic acid (0.69 mL, 5.84 mmol) and NH$_4$OAc (0.631 g, 8.18 mmol) in EtOH (4 mL). The solution was refluxed for 3 h and then cooled to room temperature. The EtOH was removed in vacuo and the residue transferred to a separatory funnel with EtOAc. The organic layer was washed 3× with sat. NaHCO$_3$, 3× with water, and 3× with Brine, and then dried (MgSO$_4$). The solvent was removed to give a yellow oil which was purified by column chromatography (silica gel, 98:2 to 96:4 CH$_2$Cl$_2$/MeOH) to give the title compound 0.872 g, 58% as a light-yellow oil. $^1$H NMR (400 MHz, CD$_3$OD) δ 4.17 (q, 2H, J=7.2 Hz), 3.90 (d, 2H, J=8.8 Hz), 3.74 (d, 2H, J=8.4 Hz), 2.76 (s, 2H), 1.45 (s, 9H), 1.27 (t, 3H, J=7.2).); MS ESI 259.0 [M+H]+, calcd for [C$_{12}$H$_{22}$N$_2$O$_4$+H]+ 259.32.

Preparation 5. General Method for N-hydroxysuccinimide esters

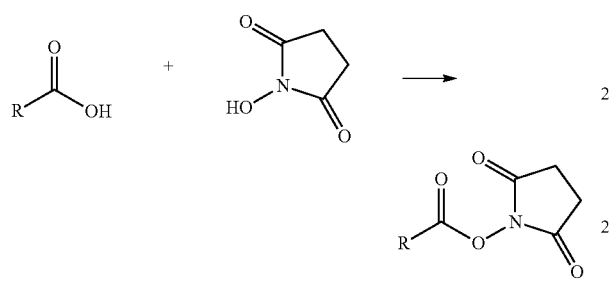

To a solution of carboxylic acid (1 mmol) in CH$_2$Cl$_2$ (5 mL) was added N-hydroxysuccinimide (138 mg, 1.2 mmol), EDC (230 mg, 1.2 mmol) and diisopropylethyl amine (0.7 mL, 4 mmol). The solution was stirred for 16 h at room temperature. Methylene chloride (75 mL) was added and the solution was washed with saturated sodium bicarbonate (2×10 mL), water (20 mL), dried over MgSO$_4$ and concentrated to give the desired ester which was used without further purification. Proton NMRs and MS were consistent with the desired products.

Preparation 6. 2-chloroethyl N-(4-octylphenyl)sulfamoylcarbamate

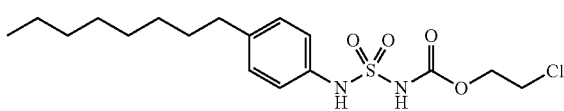 [SMILES: CCCCCCCCc1ccc(NS(=O)(=O)NC(=O)OCCCl)cc1]

A solution of chlorosulfonyl isocyanate (1.41 g, 10 mmol) in dichloromethane (5 mL) was treated with 2-chloroethanol (810 mg, 10 mmol) and stirred for 10 min at rt. The resulting solution was stored at ~5° C.; aliquots were used as required. For example a solution of 4-n-octylaniline (2.05 g, 10 mmol) and triethylamine (1.54 mL, 11 mmol) in dichloromethane (20 mL) at 0° C. was treated dropwise with the solution of sulfamoyl chloride prepared as described above. After the addition was complete, the resulting mixture was stirred for 60 min at 0° C. and diluted with dichloromethane (40 mL). The dichloromethane solution was washed with 0.1 N HCl (20 mL), dried (Na$_2$SO$_4$) and concentrated to reduce the volume. The resultant white precipitate was collected by suction filtration to give the title compound (1.60 g) as white solid. Further concentration of the filtrate yielded an additional batch (1.02 g) as white solid. Total yield was 2.62 g (67%). $^1$H NMR (400 MHz, CDCl$_3$) δ 7.21 (s, 1H), 7.20-7.10 (m, 4H), 7.11 (s, 1H), 4.46 (s, 2H), 3.71 (s, 2H), 2.60 (t, 2H, J=6.8 Hz), 1.58 (s, 2H), 1.37-1.20 (m, 10H), 0.88 (t, 3H, J=6.4 Hz).

Example S1

4-(carboxymethyl)-1-methyl-4-(3-(4-octylphenyl) ureido)piperidinium 2,2,2-trifluoroacetate

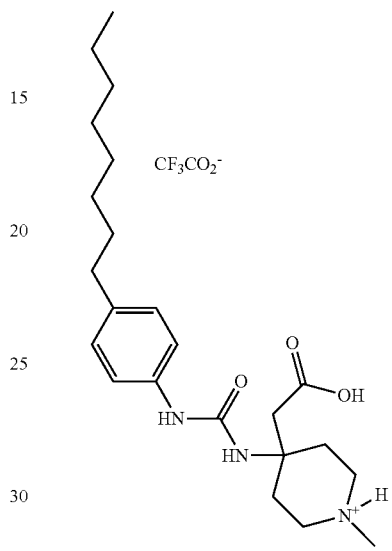

a) Ethyl 2-(1-methyl-4-(3-(4-octylphenyl)ureido) piperidin-4-yl)acetate

A stirred solution of ethyl 2-(4-amino-1-methylpiperidin-4-yl)acetate (62 mg, 0.308 mmol) in CH$_2$Cl$_2$ (2 mL) was treated with NEt$_3$ (0.13 mL, 0.924 mmol.), and 1-isocyanato-4-octylbenzene (0.071 mL, 0.308 mmol). The reaction was stirred overnight, at room temperature, then the solvent removed in vacuo and the product purified by column chromatography to obtain the title compound (94 mg, 71%). $^1$H NMR (400 MHz, CDCl$_3$) δ 7.19 (d, 2H, J=8.4 Hz), 7.12 (d, 2H, J=8.4 Hz), 6.45 (bs, 1H), 4.78 (bs, 1H), 4.09 (q, 2H, J=7.2 Hz), 2.90 (s, 2H), 2.58-2.48 (m, 4H), 2.39-2.19 (m, 4H), 2.25 (s, 3H), 1.75-1.70 (m, 2H), 1.60-1.54 (m, 2H), 1.30-1.23 (m, 13H), 0.80 (t, 3H, 6.4 Hz); MS ESI 432.4 [M+H]$^+$, calcd for [C$_{25}$H$_{41}$N$_3$O$_3$+H]$^+$ 432.62.

b) 4-(carboxymethyl)-1-methyl-4-(3-(4-octylphenyl) ureido)piperidinium 2,2,2-trifluoroacetate A solution of ethyl 2-(1-methyl-4-(3-(4-octylphenyl)ureido)piperidin-4-yl)acetate (20 mg, 0.046 mmol) in MeOH/water (4:1) (1 mL) was treated with LiOH (12 mg, 0.460 mmol) at room temperature and the reaction stirred overnight. The MeOH was removed in vacuo and the product was diluted with water and purified by reverse-phase preparatory-HPLC to yield the title compound (19 mg, 79%). $^1$H NMR (400 MHz, CD$_3$OD) δ 7.22 (d, 2H, J=8.4 Hz), 7.08 (d, 2H, J=8.4 Hz), 3.49-3.43 (m, 2H), 3.27-3.18 (m, 2H), 2.90 (s, 3H), 2.86 (s, 2H), 2.78-2.71 (m, 2H), 2.56 (t, 2H, J=7.2 Hz), 1.94-1.86 (m, 2H), 1.61-1.56 (m, 2H), 1.37-1.23 (m, 10H), 0.90 (t, 3H, 6.4 Hz); MS ESI 404.3 [M+H]% calcd for [C$_{23}$H$_{37}$N$_3$O$_3$+H]$^+$ 404.57.

Example S2

4-(Carboxymethyl)-1,1-dimethyl-4-(3-(4-octylphenyl)ureido)piperidinium 2,2,2-trifluoroacetate

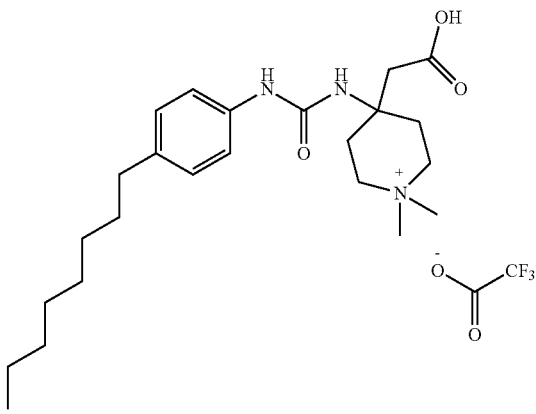

a) 4-(2-Ethoxy-2-oxoethyl)-1,1-dimethyl-4-(3-(4-octylphenyl)ureido)piperidinium iodide A solution of ethyl 2-(1-methyl-4-(3-(4-octylphenyl)ureido)piperidin-4-yl)acetate (73 mg, 0.169 mmol) in $CH_2Cl_2$ (5 mL) was treated with MeI (0.11 mL, 1.69 mmol) and the reaction stirred overnight at room temperature. The solvent was removed in vacuo to yield crude title compound (95 mg, 98%) which was used without further purification. $^1$H NMR (400 MHz, $CDCl_3$) δ 8.35 (bs, 1H), 7.42 (d, 2H, J=8.4 Hz), 7.05 (d, 2H, J=8.4 Hz), 6.49 (bs, 1H), 4.39-4.32 (m, 2H), 4.14 (q, 2H, J=7.2 Hz), 3.41-3.34 (m, 5H), 3.21 (s, 2H), 3.20 (s, 3H), 2.64-2.41 (m, 6H), 1.29-1.20 (m, 13H), 0.89 (t, 3H, 6.4 Hz); MS ESI 446.4 [M]$^+$, calcd for $[C_{26}H_{44}N_3O_3]^+$ 446.65.

b) 4-(Carboxymethyl)-1,1-dimethyl-4-(3-(4-octylphenyl)ureido)piperidinium 2,2,2-trifluoroacetate A solution of 4-(2-ethoxy-2-oxoethyl)-1,1-dimethyl-4-(3-(4-octylphenyl)ureido)-piperidinium iodide (90 mg, 0.156 mmol) in MeOH/water (4:1) (5 mL) was treated with LiOH (37 mg, 1.56 mmol.) at room temperature and the reaction stirred overnight. The MeOH was removed in vacuo and the crude product was diluted with water and purified by reverse-phase preparatory-HPLC to yield the title compound (42 mg, 51%). $^1$H NMR (400 MHz, $CD_3OD$) δ 7.21 (d, 2H, J=8.3 Hz), 7.06 (d, 2H, J=8.3 Hz), 3.58-3.46 (m, 2H), 3.45-3.36 (m, 2H), 3.20 (s, 3H), 3.16 (s, 3H), 2.92 (s, 2H), 2.69-2.60 (m, 2H), 2.53 (t, 2H, J=7.5 Hz), 2.25-2.14 (m, 2H), 1.62-1.51 (m, 2H), 1.36-1.22 (m, 10H), 0.88 (t, 3H, J=6.7 Hz); MS ESI 418.3 [M+H]$^+$, calcd for $[C_{24}H_{39}N_3O_3+H]^+$ 418.59.

Example S3

4-(carboxymethyl)-1-methyl-4-(4-pentylphenylsulfonamido)piperidinium 2,2,2-trifluoroacetate

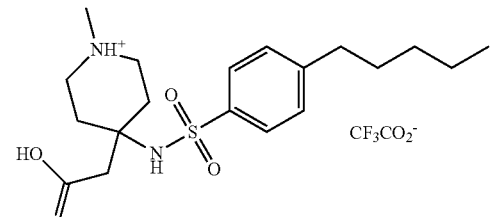

a) Ethyl 2-(1-methyl-4-(4-pentylphenylsulfonamido)piperidin-4-yl)acetate

A stirred solution of ethyl 2-(4-amino-1-methylpiperidin-4-yl)acetate (76 mg, 0.378 mmol) in $CH_2Cl_2$ (2 mL) was treated with $NEt_3$ (0.24 mL, 1.70 mmol), and 4-pentylbenzene-1-sulfonyl chloride (140 mg, 0.567 mmol). The reaction was stirred overnight, at room temperature, then the solvent removed in vacuo and the product purified by column chromatography to obtain the title compound (148 mg, 95%). $^1$H NMR (400 MHz, $CD_3OD$) δ 7.77 (d, 2H, J=7.6 Hz), 7.35 (d, 2H, J=7.3 Hz), 4.00 (q, 2H, J=6.7), 2.69 (t, 2H, J=7.0 Hz), 2.57 (s, 2H), 2.46-2.36 (m, 2H), 2.20-2.02 (m, 7H), 1.68-1.60 (m, 4H), 1.41-1.25 (m, 4H), 1.20 (t, 3H, J=6.4 Hz), 0.89 (t, 3H, J=6.7 Hz); MS ESI 411.3 [M+H]$^+$, calcd for $[C_{21}H_{34}N_2O_4S+H]^+$ 411.58.

b) 4-(carboxymethyl)-1-methyl-4-(4-pentylphenylsulfonamido)piperidinium 2,2,2-trifluoroacetate Ethyl 2-(1-methyl-4-(4-pentylphenylsulfonamido)piperidin-4-yl)acetate (50 mg, 0.122 mmol) was saponified and the product purified, as described in Example 1b, to obtain the title compound (30 mg, 49%). $^1$H NMR (400 MHz, $CD_3OD$) δ 7.79 (d, 2H, J=8.1 Hz), 7.39 (d, 2H, J=8.1 Hz), 3.37-3.27 (m, 2H), 3.26-3.15 (m, 2H), 2.83 (s, 3H), 2.73-2.66 (t, 2H, J=8.0 Hz), 2.55-2.46 (m, 2H), 2.32 (s, 2H), 1.92-1.79 (m, 2H), 1.70-1.58 (m, 2H), 1.41-1.25 (m, 4H), 0.89 (t, 3H, J=6.8 Hz); MS ESI 383.2 [M+11]$^+$, calcd for $[C_{19}H_{30}N_2O_4S+H]^+$ 383.52.

Example S4

4-(Carboxymethyl)-1,1-dimethyl-4-(4-pentylphenylsulfonamido)piperidinium 2,2,2-trifluoroacetate

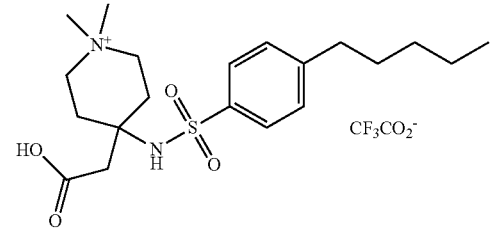

a) 4-(2-Ethoxy-2-oxoethyl)-1,1-dimethyl-4-(4-pentylphenylsulfonamido)piperidinium iodide Ethyl 2-(1-methyl-4-(4-pentylphenylsulfonamido)piperidin-4-yl)acetate (100 mg, 0.244 mmol) was treated with MeI as described in Example 2a to yield crude title compound (133 mg, 98%) which was used without further purification. $^1$H NMR (400 MHz, CDCl$_3$) δ 7.77 (d, 2H, J=8.0 Hz), 7.33 (d, 2H, J=8.0 Hz), 6.05 (s, 1H), 3.98 (q, 2H, J=6.7), 3.79-3.70 (m, 2H), 3.65-3.60 (m, 5H), 3.40 (s, 3H), 2.69 (t, 2H, J=7.0 Hz), 2.54 (s, 2H), 2.49-2.43 (m, 4H), 1.67-1.61 (m, 2H), 1.38-1.32 (m, 4H), 1.17 (t, 3H, J=6.4 Hz), 0.91 (t, 3H, J=6.7 Hz); MS ESI 425.3 [M+H]$^+$, calcd for [C$_{22}$H$_{36}$N$_2$O$_4$S+H]$^+$ 425.60.

b) 4-(Carboxymethyl)-1,1-dimethyl-4-(4-pentylphenylsulfonamido)piperidinium 2,2,2-trifluoroacetate 4-(2-Ethoxy-2-oxoethyl)-1,1-dimethyl-4-(4-pentylphenylsulfonamido)piperidinium iodide (133 mg, 0.240 mmol) was saponified and the product purified, as described in Example 1b, to obtain the title compound (40 mg, 33%). $^1$H NMR (400 MHz, CD$_3$OD) δ 7.81 (d, 2H, J=8.0 Hz), 7.41 (d, 2H, J=8.0 Hz), 3.58-3.50 (m, 2H), 3.38-3.32 (m, 2H), 3.18 (s, 3H), 3.13 (s, 3H), 2.73 (t, 2H, J=7.6 Hz), 2.48-2.42 (m, 4H), 2.19-2.10 (m, 2H), 1.71-1.63 (m, 2H), 1.41-1.32 (m, 4H), 0.92 (t, 3H, J=6.7 Hz); MS ESI 397.2 [M+H]$^+$, calcd for [C$_{20}$H$_{32}$N$_2$O$_4$S+H]$^+$ 397.55.

Example S5

4-(Carboxymethyl)-1,1-dimethyl-4-(5-phenethylfuran-2-carboxamido)-piperidinium 2,2,2-trifluoroacetate

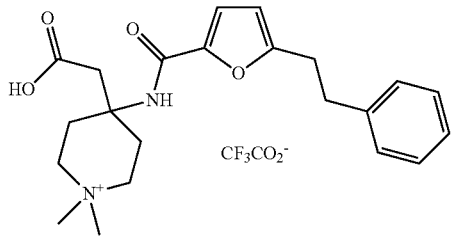

a) Ethyl 2-(1-methyl-4-(5-phenethylfuran-2-carboxamido)piperidin-4-yl)acetate A stirred solution of ethyl 2-(4-amino-1-methylpiperidin-4-yl)acetate (16 mg, 0.077 mmol) in CH$_2$Cl$_2$ (1 mL) was treated with NEt$_3$ (31 uL, 0.219 mmol), and 2,5-dioxopyrrolidin-1-yl 5-phenethylfuran-2-carboxylate, prepared as described in Preparation 5 (23 mg, 0.073 mmol). The reaction was stirred overnight, at room temperature, then the solvent removed in vacuo and the crude product purified by column chromatography to obtain the title compound (25 mg, 86%). $^1$H NMR (400 MHz, CD$_3$OD) δ 7.29-7.16 (m, 5H), 7.00 (s, 1H), 6.17 (s, 1H), 4.06 (q, 2H, J=7.2 Hz), 3.05 (s, 4H), 2.88 (s, 2H), 2.75-2.69 (m, 2H), 2.54-2.48 (m, 2H), 2.41-2.31 (m, 5H), 1.87-1.81 (m, 2H), 1.15 (t, 3H, J=7.2 Hz); MS ESI 399.2 [M+H]$^+$, calcd for [C$_{23}$H$_{30}$N$_2$O$_4$+H]$^+$ 399.50.

b) 4-(2-Ethoxy-2-oxoethyl)-1,1-dimethyl-4-(5-phenethylfuran-2-carboxamido)-piperidinium iodide Ethyl 2-(1-methyl-4-(5-phenethylfuran-2-carboxamido)piperidin-4-yl)acetate (25 mg, 0.063 mmol) was treated with MeI (38 uL, 0.630 mmol) as described in Example 2a to yield crude title compound (32 mg, 94%) which was used without further purification. NMR (400 MHz, CD$_3$OD) δ 7.29-7.16 (m, 5H), 7.07 (s, 1H), 6.20 (s, 1H), 4.10 (q, 2H, J=7.2 Hz), 3.56-3.46 (m, 4H), 3.23 (s, 3H), 3.21 (s, 3H), 3.03 (s, 4H), 3.01 (s, 2H), 2.91-2.83 (m, 2H), 2.29-2.19 (m, 2H), 1.17 (t, 3H, J=7.2 Hz); MS ESI 414.1 [M+H]$^+$, calcd for [C$_{24}$H$_{32}$N$_2$O$_4$+H]$^+$ 413.53.

c) 4-(Carboxymethyl)-1,1-dimethyl-4-(5-phenethylfuran-2-carboxamido)piperidinium 2,2,2-trifluoroacetate 4-(2-Ethoxy-2-oxoethyl)-1,1-dimethyl-4-(5-phenethylfuran-2-carboxamido)-piperidinium iodide (32 mg, 0.059 mmol) was saponified and the product purified, as described in Example 1b, to obtain the title compound (7 mg, 24%). NMR (400 MHz, CD$_3$OD) δ 7.29-7.15 (m, 5H), 7.06 (s, 1H), 6.19 (s, 1H), 3.56-3.43 (m, 4H), 3.22 (s, 3H), 3.21 (s, 3H), 3.02 (s, 4H), 3.01 (s, 2H), 2.91-2.84 (m, 2H), 2.31-2.20 (m, 2H); MS ESI 385.2 [M]$^+$, calcd for [C$_{22}$H$_{29}$N$_2$O$_4$]$^+$ 385.48.

Example S6

4-(Carboxymethyl)-1,1-dimethyl-4-(5-(phenylethynyl)furan-2-carboxamido)-piperidinium 2,2,2-trifluoroacetate

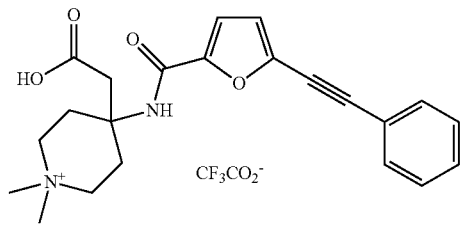

a) Ethyl 2-(1-methyl-4-(5-(phenylethynyl)furan-2-carboxamido)-piperidin-4-yl)acetate A stirred solution of ethyl 2-(4-amino-1-methylpiperidin-4-yl)acetate (53 mg, 0.263 mmol) in CH$_2$Cl$_2$ (2 mL) was treated with NEt$_3$ (0.11 mL, 0.789 mmol), and 2,5-dioxopyrrolidin-1-yl 5-(phenylethynyl)furan-2-carboxylate, prepared as described in Preparation 5 (89 mg, 0.289 mmol). The reaction was stirred overnight, at room temperature, then the solvent removed in vacuo and the product purified by column chromatography to obtain the title compound (51 mg, 49%). $^1$H NMR (400 MHz, CD$_3$OD) δ 7.57-7.53 (m, 2H), 7.44-7.40 (m, 3H), 7.16 (s, 1H), 6.84 (s, 1H), 4.08 (q, 2H, J=7.2 Hz), 2.89 (s, 2H), 2.70-2.65 (m, 2H), 2.54-2.47 (m, 2H), 2.39-2.25 (m, 5H), 1.85-1.80 (m, 2H), 1.17 (t, 3H, J=7.2 Hz); MS ESI 395.2 [M+H]$^+$, calcd for [C$_{23}$H$_{26}$N$_2$O$_4$+H]$^+$ 395.47.

b) 4-(2-ethoxy-2-oxoethyl)-1,1-dimethyl-4-(5-(phenylethynyl)furan-2-carboxamido)-piperidinium iodide Ethyl 2-(1-methyl-4-(5-(phenylethynyl)furan-2-carboxamido)piperidin-4-yl)acetate (51 mg, 0.129 mmol) was treated with MeI (80 uL, 1.29 mmol) as described in Example 2a to yield crude title compound (68 mg, 97%) which was used without further purification. $^1$H NMR (400 MHz, CD$_3$OD) δ

7.57-7.53 (m, 2H), 7.47-7.42 (m, 3H), 7.21 (s, 1H), 6.87 (s, 1H), 4.11 (q, 2H, J=7.2 Hz), 3.58-3.42 (m, 4H), 3.22 (s, 3H), 3.21 (s, 3H), 3.02 (s, 2H), 2.90-2.83 (m, 2H), 2.29-2.19 (m, 2H), 1.18 (t, 3H, J=7.2 Hz); MS ESI 409.3 [M+H]$^+$, calcd for [$C_{24}H_{28}N_2O_4$+H]$^+$ 409.50.

c) 4-(Carboxymethyl)-1,1-dimethyl-4-(5-(phenylethynyl)furan-2-carboxamido)-piperidinium trifluoroacetate 4-(2-Ethoxy-2-oxoethyl)-1,1-dimethyl-4-(5-(phenylethynyl)furan-2-carboxamido)-piperidinium iodide was (68 mg, 0.126 mmol) saponified and the product purified, as described in Example 1b, to obtain the title compound (43 mg, 69%). $^1$H NMR (400 MHz, CD$_3$OD) δ 7.56-7.52 (m, 2H), 7.45-7.41 (m, 3H), 7.21 (s, 1H), 6.86 (s, 1H), 3.58-3.42 (m, 4H), 3.22 (s, 3H), 3.21 (s, 3H), 3.02 (s, 2H), 2.91-2.85 (m, 2H), 2.32-2.22 (m, 2H); MS ESI 381.2 [M+H]$^+$, calcd for [$C_{22}H_{24}N_2O_4$+H]$^+$ 381.44.

Example S7

4-(carboxymethyl)-1-methyl-4-(N-(4-octylphenyl)sulfamoylamino)-piperidinium 2,2,2-trifluoroacetate

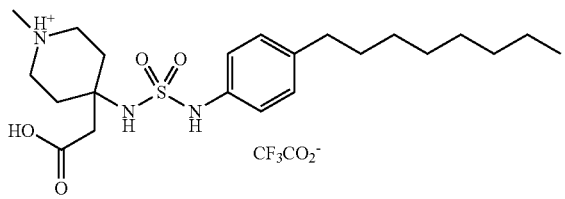

a) Ethyl 2-(1-methyl-4-(N-(4-octylphenyl)sulfamoylamino)piperidin-4-yl)acetate According to the method described in example 15a, ethyl 2-(4-amino-1-methylpiperidin-4-yl)acetate (70 mg, 0.35 mmol) and 2-chloroethyl N-(4-octylphenyl)sulfamoylcarbamate (195 mg, 0.5 mmol) were reacted to yield the title compound (56 mg, 34%). MS ESI 468.4 [M+H]$^+$, calcd for [$C_{24}H_{41}N_3O_4S$+H]$^+$ 468.29.

b) 4-(carboxymethyl)-1-methyl-4-(N-(4-octylphenyl)sulfamoylamino)-piperidinium 2,2,2-trifluoroacetate Ethyl 2-(1-methyl-4-(N-(4-octylphenyl)sulfamoylamino)piperidin-4-yl)acetate (17 mg, 0.036 mmol) was saponified as described in example 2a; preparative HPLC gave the title compound (1.0 mg, 5%) as white solid. $^1$H NMR (400 MHz, CD$_3$OD) δ 7.20 (d, 2H, J=8.0 Hz), 7.15 (d, 2H, J=8.0 Hz), 3.00-2.80 (m, 4H), 2.59 (brs, 5H), 2.48 (d, 2H, J=13.6 Hz), 2.05-1.95 (m, 2H), 1.65-1.55 (m, 2H), 1.45-1.30 (m, 10H), 0.91 (t, 3H, J=6.8 Hz); MS ESI 440.3 [M+H]$^+$, calcd for [$C_{22}H_{37}N_3O_4S$+H]$^+$ 440.26.

Example S8

4-(carboxymethyl)-1,1-dimethyl-4-(N-(4-octylphenyl)sulfamoylamino)piperidinium 2,2,2-trifluoroacetate

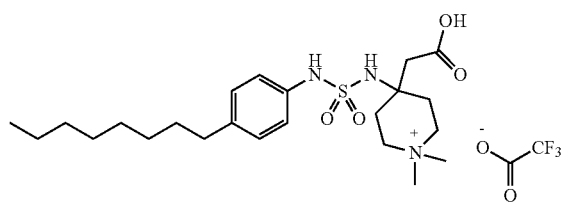

Ethyl 2-(1-methyl-4-(N-(4-octylphenyl)sulfamoylamino)piperidin-4-yl)acetate (39 mg, 0.084 mmol), was treated with MeI (0.2 mL, 3.2 mmol) as described in example 2a to yield crude 4-(2-ethoxy-2-oxoethyl)-1,1-dimethyl-4-(N-(4-octylphenyl)sulfamoyl-amino)piperidinium iodide which was used without further purification. Subsequent saponification and preparative HPLC purification gave the title compound (8 mg, 17%) as white solid. $^1$H NMR (400 MHz, CD$_3$OD) δ 7.20 (d, 2H, J=8.4 Hz), 7.15 (d, 2H, J=8.8 Hz), 3.27-3.15 (m, 4H), 3.08 (s, 3H), 2.88 (s, 2H), 2.81 (s, 3H), 2.59 (t, 2H, J=15.6 Hz), 2.39 (d, 2H, J=15.6 Hz), 2.26-2.18 (m, 2H), 1.65-1.55 (m, 2H), 1.48-1.25 (m, 10H), 0.91 (t, 3H, J=6.8 Hz); MS ESI 454.3 [M+H]$^+$, calcd for [$C_{23}H_{39}N_3O_4S$+H]$^+$ 454.27.

Example S9

3-(Carboxymethyl)-1-methyl-3-(3-(4-octylphenyl)ureido)piperidinium 2,2,2-trifluoroacetate

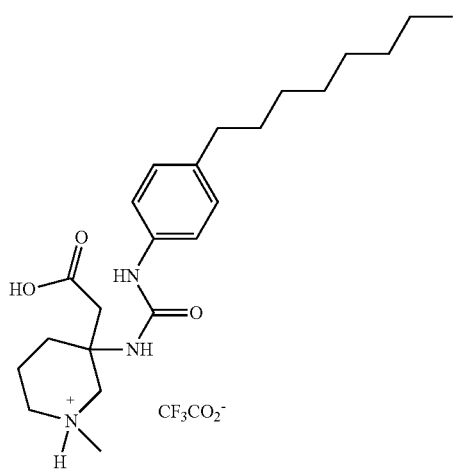

a) Methyl 2-(1-methyl-3-(3(4-octylphenyl)ureido)piperidin-3-yl)acetate

A solution of methyl 2-(3-amino-1-methylpiperidin-3-yl)acetate (235 mg, 1.3 mmol) in and THF (10 mL), at 0° C., under N$_2$, was treated with DIPEA (0.22 mL, 1.3 mmol) and triphosgene (133 mg, 0.45 mmol), in one portion. The reaction was stirred at 0° C. for a few min and then at rt for 110 min. The reaction was cooled to 0° C., treated with the N-octylaniline (0.29 mL, 1.3 mmol) followed by DIPEA (0.22 mL, 1.3 mmol). After 5 min the cooling bath was removed and the reaction was diluted with and THF (10 mL). Stirring was continued at rt overnight. The reaction was then concentrated under reduced pressure and purified by flash chromatography on silica gel using 0-12% MeOH/DCM as the eluent to isolate the title product as a white solid (0.296 g, 56%). $^1$H NMR (400 MHz, CD$_3$OD) δ ppm 7.20 (d, J=8.59 Hz, 2 H), 7.05 (d, J=8.34 Hz, 2 H), 3.64 (s, 3 H), 2.89 (m, 2 H), 2.76 (br. s., 1 H), 2.54 (t, J=7.58 Hz, 2 H), 2.27 (s, 3 H), 1.97-2.23 (m, 3 H), 1.67-1.85 (m, 1 H), 1.50-1.66 (m, 3 H), 1.30 (d, J=7.33 Hz, 12 H), 0.89 (t, J=6.82 Hz, 3 H). MS ESI [M+H]$^+$, calcd for [C$_{24}$H$_{39}$N$_3$O$_3$+H] 418.59 found m/z 418.3 (100).

b) 3-(Carboxymethyl)-1-methyl-3-(3-(4-octylphenyl)ureido)piperidinium 2,2,2-trifluoroacetate Methyl 2-(1-methyl-3-(3-(4-octylphenyl)ureido)piperidin-3-yl)acetate (53 mg, 0.13 mmol) and LiOH (43 mg, 1.8 mmol) were dissolved in MeOH (10 mL) and H$_2$O (3.5 mL). The reaction was stirred at rt overnight. MeOH was removed under reduced pressure and the aq residue was loaded on C18 column (5 g, Biotage, 25 mL cartridge). The column was washed with xs H$_2$O (~220 mL) and the material was eluted using H$_2$O:MeCN(2% AcOH) gradient 0-90% with respect to MeCN—AcOH. Thus obtained solid was purified by prep HPLC to afford the title compound as a white solid (32.6 mg, 51%) $^1$H NMR (400 MHz, CD$_3$OD) δ ppm 7.26 (d, J=8.34 Hz, 2 H), 7.08 (d, J=8.59 Hz, 2 H), 4.44 (d, J=12.38 Hz, 1 H), 3.45 (d, J=11.87 Hz, 1 H), 2.91-3.12 (m, 3 H), 2.86 (s, 3 H), 2.50-2.63 (m, 3 H), 2.20 (d, J=13.89 Hz, 1H), 1.99-2.14 (m, 1 H), 1.86-1.98 (m, 1H), 1.73 (td, J=13.71, 4.17 Hz, 1 H), 1.51-1.63 (m, 2 H), 1.21-1.37 (m, 10 H), 0.89 (t, J=6.82 Hz, 3 H). MS ESI [M+H]$^+$, calcd for [C$_{23}$H$_{37}$N$_3$O$_3$+H]$^+$ 404.57 found m/z 404.3 (100).

Example S10

3-(carboxymethyl)-1,1-dimethyl-3-(3-(4-octylphenyl)ureido)-piperidinium 2,2,2-trifluoroacetate

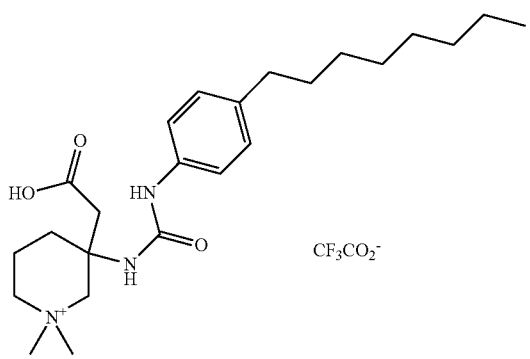

Methyl 2-(1-methyl-3-(3-(4-octylphenyl)ureido)piperidin-3-yl)acetate (77 mg, 0.18 mmol) in Et$_2$O (10 mL) was treated with MeI (0.04 mL, 0.6 mmol) and stirred at rt overnight; DIPEA (0.05 mL, 0.3 mmol) and MeI (0.06 mL, 0.1 mmol) were added and stirring was continued for 3 d. The reaction was evaporated to dryness. LiOH (115 mg, 4.8 mmol), MeOH (8 mL) and H$_2$O (2.5 mL) were added and the reaction mixture was stirred at rt overnight. The crude mixture was concentrated to dryness, taken into 10% MeOH/DCM and filtered through Celite. The filtrate was concentrated to dryness and the residue was purified by preparative TLC (silica gel, 70% MeOH/DCM) followed by preparative HPLC to afford the title compound as a white solid (14.2 mg, 15%). $^1$H NMR (400 MHz, CD$_3$OD) δ ppm 7.25 (d, J=8.34 Hz, 2 H), 7.08 (d, J=8.59 Hz, 2 H), 4.60 (d, J=13.39 Hz, 1 H), 3.56 (d, J=13.14 Hz, 1 H), 3.19 (s, 3 H), 3.11 (d, J=14.91 Hz, 1 H), 2.47-2.58 (m, 3 H), 2.12-2.38 (m, 2 H), 1.87-2.02 (m, 1 H), 1.77 (td, J=13.89, 3.79 Hz, 1 H), 1.49-1.64 (m, 2 H), 1.21-1.38 (m, 10 H), 0.89 (t, J=6.82 Hz, 3 H). MS ESI [M+H]$^+$, calcd for [C$_{24}$H$_{39}$N$_3$O$_3$+H]$^+$: 418.59 found m/z 418.3 (100).

Example S11

3-(carboxymethyl)-1-methyl-3-(4-pentylphenylsulfonamido)piperidinium 2,2,2-trifluoroacetate

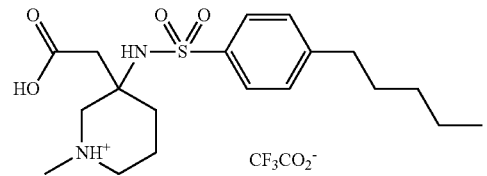

a) Methyl 2-(1-methyl-3-(4-pentylphenylsulfonamido)piperidin-3-yl)acetate

A solution of ethyl 2-(3-amino-1-methylpiperidin-3-yl)acetate (52 mg, 0.28 mmol) and triethylamine (0.2 mL, 1.44 mmol) in dichlormethane (15 mL) was treated with 4-n-pentylbenzenesulfonly chloride (120 mg, 0.487 mmol). The resulting mixture was stirred overnight. After removal of the volatiles, the residue was redissolved in dichloromethane, washed with sat. NaHCO$_3$, dried (Na$_2$SO$_4$), evaporated and purified by flash chromatography (eluent: EtOAc/hex 1:1 to EtOAc) to give the title compound. (95 mg, 86%) as colorless oil. $^1$H NMR (400 MHz, CDCl$_3$) δ 7.80 (d, 2H, J=8.0 Hz), 7.27 (d, 2H, J=8.0 Hz), 5.67 (brs, 1H), 3.55 (s, 3H), 2.84 (d, 1H, J=11.6 Hz), 2.73-2.60 (m, 4H), 2.47 (brs, 1H), 2.20-1.92 (m, 6H; NCH$_3$ and 3H), 1.70-1.57 (m, 3H), 1.48-1.27 (m, 6H), 0.88 (t, 3H, J=7.2 Hz); MS 397.2 ESI [M+H]$^+$, calcd for [C$_{20}$H$_{32}$N$_2$O$_4$S+H]$^+$ 397.22 b) 3-(carboxymethyl)-1-methyl-3-(4-pentylphenylsulfonamido)piperidinium 2,2,2-trifluoroacetate Saponification of methyl 2-(1-methyl-3-(4-pentylphenylsulfonamido)piperidin-3-yl)-acetate (13.5 mg, 0.034 mmol), as described in example 1b using LiOH (48 mg, 2 mmol) in MeOH (5 mL) and H$_2$O (1 mL) followed by preparative HPLC purification of the product gave the title compound (13 mg, 77%) as white solid. $^1$H NMR (400 MHz, CD$_3$OD) δ 7.84 (d, 2H, J=8.4 Hz), 7.41 (d, 2H, J=8.4 Hz), 4.49 (d, 1H, J=12.8 Hz), 4.46 (d, 1H, J=11.2 Hz), 3.12 (d, 1H, J=12.4 Hz), 2.96 (dt, 1H, J=12.8 Hz, 2.4 Hz), 2.89 (s, 3H), 2.73 (t, 2H, J=7.6 Hz), 2.32 (d, 1H, J=7.2 Hz), 2.25-2.10 (m, 3H), 1.82 (d, 1H, J=14.4 Hz), 1.71-1.55 (m, 3H), 1.43-1.27 (m, 4H), 0.91 (t, J=6.8 Hz); MS ESI 383.2 [M+H]$^+$, calcd for [C$_{19}$H$_{30}$N$_2$O$_4$S+H]+ 383.20

Example S12

3-(carboxymethyl)-1,1-dimethyl-3-(4-pentylphenyl-sulfonamido)-piperidinium 2,2,2-trifluoroacetate

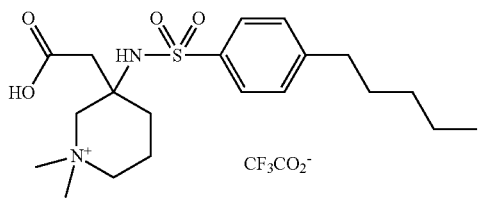

Methyl 2-(1-methyl-3-(4-pentylphenylsulfonamido)piperidin-3-yl)acetate (35 mg, 0.073 mmol), was methylated with MeI as described in example 2a to yield crude methyl 2-(1,1-dimethyl-3-(4-pentylphenylsulfonamido)piperidin-3-yl)acetate which was used without further purification. This material was saponified as described in example 1b and the product was purified by preparative HPLC to give the title compound (8 mg, 17%) as white solid. $^1$H NMR (400 MHz, CD$_3$OD) δ 7.82 (d, 2H, J=7.6 Hz), 7.40 (d, 2H, J=8.0 Hz), 4.17 (d, 1H, J=14.0 Hz), 3.53 (d, 1H, J=12.8 Hz), 3.43 (s, 3H), 3.35-3.20 (m, 2H, overlapping with MeOH), 3.19 (s, 3H), 2.60 (t, 2H, J=7.6 Hz), 2.58 (d, 1H, J=14.4 Hz), 2.48 (d, 1H, J=18.0 Hz), 2.43 (d, 1H, J=18.0 Hz), 2.09 (q, 1H, J=12.8 Hz), 1.81 (d, 1H, J=15.6 Hz), 1.70-1.54 (m, 3H), 1.42-1.30 (m, 4H), 0.92 (t, 3H, J=13.0 Hz); MS ESI 397.2 [M+H]$^+$, calcd for [C$_{20}$H$_{32}$N$_2$O$_4$S+H]$^+$ 397.22

Example S13

3-(carboxymethyl)-1-methyl-3-(5-phenethylfuran-2-carboxamido)-piperidinium 2,2,2-trifluoroacetate

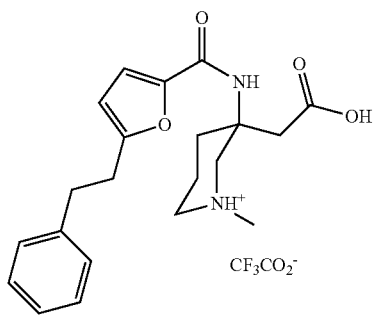

a. Methyl 2-(1-methyl-3-(5-phenethylfuran-2-carboxamido)piperidin-3-yl)acetate A solution of methyl 2-(3-amino-1-methylpiperidin-3-yl)acetate (37 mg, 0.2 mmol) and 2,5-dioxopyrrolidin-1-yl 5-phenethylfuran-2-carboxylate (75 mg, 0.24 mmol) in DMF (1 mL) was treated with triethylamine (0.11 μL, 0.8 mmol) and stirred at room temperature for 18 h. Diethyl ether (20 mL) was added and the resulting white precipitate was collected and purified by silica gel chromatography (elution 5% MeOH/CH$_2$Cl$_2$ to 10% MeOH/CH$_2$Cl$_2$) to give the title compound as a white powder (69 mg, 87%). MS ESI 385.2 [M+H]$^+$, calcd for [C$_{22}$H$_{28}$N$_2$O$_4$+H] 385.20.

b) 3-(carboxymethyl)-1-methyl-3-(5-phenethylfuran-2-carboxamido)-piperidinium 2,2,2-trifluoroacetate To a solution of ethyl 2-(1-methyl-3-(5-phenethylfuran-2-carboxamido)piperidin-3-yl)acetate (7 mg, 0.018 mmol) in MeOH (1 mL) was added 1N sodium hydroxide (1 mL). The solution was stirred for 1 h at room temperature, acidified to pH 1 and purified by HPLC to give the title compound as a white solid (3 mg, 32%). $^1$H NMR (400 MHz, D$_2$O) δ 7.22 (t, 2H, J=7.7 Hz), 7.16-7.11 (m, 3H), 6.96 (d, 1H, J=3.6 Hz) 6.10 (d, 1H, J=3.6 Hz), 4.41 (d, 1H, J=7.3 Hz), 3.68-3.36 (m, 1H), 3.03-3.00 (m, 1H), 2.96-2.88 (m, 7H), 2.76 (s, 3H), 2.60-2.57 (m, 1H), 2.30-2.27 (m, 1H), 1.90-1.84 (m, 2H), 1.65-1.59 (m, 1H); MS ESI 371.2 [M+H]$^+$, calcd for [C$_{21}$H$_{26}$N$_2$O$_4$+H] 371.19.

Example S14

3-(carboxymethyl)-1,1-dimethyl-3-(5-phenethylfuran-2-carboxamido)piperidinium 2,2,2-trifluoroacetate

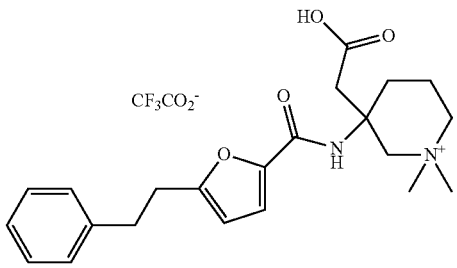 [SMILES: C[N+]1(C)CCCC(CC(=O)O)(NC(=O)c2ccc(CCc3ccccc3)o2)C1 ; "CF3CO2-"]

a) 3-(2-methoxy-2-oxoethyl)-1,1-dimethyl-3-(5-phenethylfuran-2-carboxamido)-piperidinium iodide According to the method described in example 2a, methyl 2-(1-methyl-3-(5-phenethyl-furan-2-carboxamido)piperidin-3-yl)acetate was reacted with methyl iodide to give the title compound as a white solid (quantitative). MS ESI 399.2 [M]$^+$, calcd for [C$_{23}$H$_{31}$N$_2$O$_4$]$^+$ 399.21.

b) 3-(carboxymethyl)-1,1-dimethyl-3-(5-phenethyl-furan-2-carboxamido) piperidinium 2,2,2-trifluoroacetate According to the method described in example 13b, 3-(2-ethoxy-2-oxoethyl)-1,1-dimethyl-3-(5-phenethylfuran-2-carboxamido)piperidinium iodide was hydrolyzed with sodium hydroxide and purified by HPLC to give the title compound as a white solid (38 mg, 50%). $^1$H NMR (400 MHz, D$_2$O) δ 7.17 (t, 2H, J=7.1 Hz), 7.11 (d, 1H, J=7.4 Hz) 7.06 (d, 2H, J=7.1 Hz) 6.96 (d, 1H, J=3.6 Hz) 6.07 (d, 1H, J=3.6 Hz), 4.49-4.46 (m, 1H), 3.42-3.39 (m, 1H), 3.22-3.10 (m, 3H), 3.03 (s, 3H), 2.96 (s, 3H), 2.90-2.81 (m, 4H), 2.39-2.35 (m, 1H), 2.03-1.99 (m, 1H), 1.90-1.84 (m, 1H), 1.66-1.58 (m, 1H); MS ESI 385.2 [M+H]$^+$, calcd for [C$_{22}$H$_{29}$N$_2$O$_4$+H]+ 385.21.

Example S15

3-(carboxymethyl)-1-methyl-3-(N-(4-octylphenyl)sulfamoylamino)-piperidinium 2,2,2-trifluoroacetate

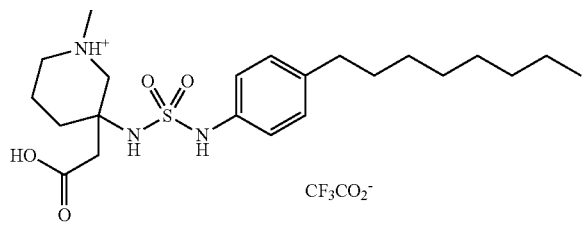

a) Methyl 2-(1-methyl-3-(N-(4-octylphenyl)sulfamoylamino)piperidin-3-yl)acetate A solution of 2-chloroethyl N-(4-octylphenyl)sulfamoylcarbamate (156 mg, 0.4 mmol) in $CH_3CN$ (10 mL) was treated with $Et_3N$ (0.14 mL, 1 mmol) and refluxed for 25 min. and cooled. A solution of 2-(3-amino-1-methylpiperidin-3-yl)acetate (62 mg, 0.33 mmol) was added and the resulting mixture was refluxed for 4 h. After removal of the solvent in vacuo, the residue was dissolved in dichloromethane (40 mL) and washed with sat. $NaHCO_3$ (10 mL), $H_2O$ (10 mL), brine (10 mL) and dried ($Na_2SO4$). After evaporation, the residue was purified by flash chromatography (EtOAc/hex 1:4 to EtOAc) to give the title compound (41 mg, 27%) as colorless oil. MS ESI 454.3$[M+H]^+$, calcd for $[C_{23}H_{39}N_3O_4S+H]^+$ 454.27.

b) 3-(carboxymethyl)-1-methyl-3-(N-(4-octylphenyl)sulfamoylamino)-piperidinium 2,2,2-trifluoroacetate Saponification of methyl 2-(1-methyl-3-(N-(4-octylphenyl)sulfamoylamino)piperidin-3-yl)acetate (8 mg, 0.018 mmol) as described in example 1b using LiOH (12 mg, 0.5 mmol) and MeOH (1.5 mL) and $H_2O$ (1.5 mL), followed by preparative HPLC purification of the product gave the title compound (5 mg, 51%) as white solid. $^1H$ NMR (400 MHz, $CD_3OD$) δ 7.15 (d, 2H, J=8.4 Hz), 7.14 (d, 2H, J=8.8 Hz), 4.00 (d, 1H, J=12.8 Hz), 3.44 (d, 1H, J=12.0 Hz), 2.97 (t, 1H, J=13.0 Hz), 2.87 (s, 3H), 2.76 (d, 1H, J=16.4 Hz), 2.60-2.50 (m, 3H), 2.30-2.15 (m, 2H), 1.84 (d, 1H, J=14.0 Hz), 1.73 (t, 1H, J=13.2 Hz), 1.65-1.55 (m, 2H), 1.37-1.25 (m, 10H), 0.90 (t, 3H, J=5.8 Hz); MS ESI 440.3 $[M+H]^+$, calcd for $[C_{22}H_{37}N_3O_4S_4+H]^+$ 440.26.

Example S16

3-(carboxymethyl)-1,1-dimethyl-3-(N-(4-octylphenyl)sulfamoylamino)-piperidinium 2,2,2-trifluoroacetate

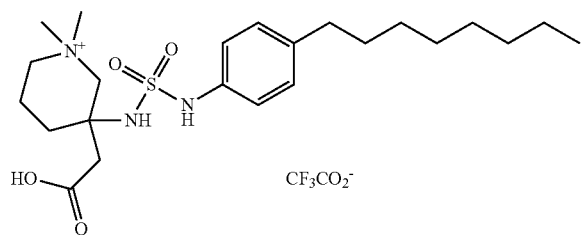

Methylation of Methyl 2-(1-methyl-3-(N-(4-octylphenyl)sulfamoylamino)piperidin-3-yl)acetate (33 mg, 0.073 mmol), as described in example 2a gave crude methyl 2-(1,1-dimethyl-3-(N-(4-octylphenyl)sulfamoylamino)piperidin-3-yl)acetate which was used without further purification. This material was saponified, as described in example 1b, using LiOH (48 mg, 2 mmol) in MeOH (5 mL) and $H_2O$ (1 mL) and the product was purified by preparative HPLC to give the title compound (23 mg, 57%) as white solid. $^1H$ NMR (400 MHz, $CD_3OD$) δ 7.18-7.12 (m, 4H), 3.99 (d, 1H, J=14.0 Hz), 3.43-3.35 (m, 2H), 3.21 (t, J=10.8 Hz), 3.11 (s, 3H), 3.06 (s, 3H), 3.03 (d, 1H, J=18.0 Hz, partly overlapping with s at 3.06), 2.64 (d, 2H, J=18.8 Hz), 2.56 (t, 2H, J=7.6 Hz), 2.08-1.95 (m, 1H), 1.77 (d, 1H, J=15.2 Hz), 1.70-1.55 (m, 3H), 1.36-1.25 (m, 10H), 0.91 (t, 3H, J=6.8 Hz); MS ESI 454.3 $[M+H]^+$, calcd for $[C_{23}H_{39}N_3O_4S+H]^+$ 454.27.

Example S17

3-(carboxymethyl)-1-methyl-3-(3-(4-octylphenyl)ureido)pyrrolidinium 2,2,2-trifluoroacetate

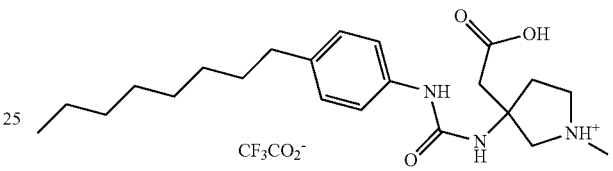

a) Benzyl 3-(2-ethoxy-2-oxoethyl)-3-(3-(4-octylphenyl)ureido)pyrrolidine-1-carboxylate To a solution of benzyl 3-amino-3-(2-ethoxy-2-oxoethyl)pyrrolidine-1-carboxylate (260 mg, 0.85 mmol) and p-octylphenylisocyanate (215 mg, 0.93 mmol) in $CH_2Cl_2$ (3 mL) was added triethylamine (0.35 mL, 2.55 mmol) to give the title compound as a brown solid (140 mg, 31%). MS ESI 538.2 $[M+H]^+$, calcd for $[C_{31}H_{43}N_3O_5+H]$ 538.32.

b) Ethyl 2-(3-(3-(4-octylphenyl)ureido)pyrrolidin-3-yl)acetate

A solution of benzyl 3-(2-ethoxy-2-oxoethyl)-3-(3-(4-octylphenyl)ureido)pyrrolidine-1-carboxylate (140 mg, 0.26 mmol) in EtOH (5 mL) was purged with nitrogen and Pd/C (25 mg) was added and the flask was purged with hydrogen and stirred for 24 h. The mixture was filtered through celite and concentrated. The residue was dissolved into $H_2O$ and lyophilized to give the title compound as a white solid (84 mg, 80%). $^1H$ NMR (400 MHz, $CD_3OD$) δ 7.25 (d, 2H, J=7.9 Hz), 7.08 (d, 2H, J=8.1 Hz), 4.16 (q, 2H, J=7.1 Hz), 4.05-4.02 (m, 1H), 3.51-3.47 (m, 2H), 3.23-3.19 (m, 1H), 2.91-2.87 (m, 1H), 2.57-2.50 (m, 3H), 2.26-2.20 (m, 1H), 1.60-1.57 (m, 2H), 1.31-1.23 (m, 15H), 0.90 (t, 3H, J=6.6 Hz).

c) ethyl 2-(1-methyl-3-(3-(4-octylphenyl)ureido)pyrrolidin-3-yl)acetate

To a solution of ethyl 2-(3-(3-(4-octylphenyl)ureido)pyrrolidin-3-yl)acetate (84 mg, 0.2 mmol) in formic acid (2 mL) was added formalin (15 μL, 0.16 mL). The solution was heated to 110° C. for 2 h. The mixture was concentrated and dissolved into $CH_2Cl_2$ (25 mL) and washed with sat. bicarbonate (2×5 mL), $H_2O$ (5 mL), dried over $MgSO_4$ and concentrated to dryness to give the title compound as a brown oil (29 mg, 35%) MS ESI 418.4 $[M+H]^+$, calcd for $[C_{24}H_{39}N_3O_3+H]$ 418.30.

d) 3-(carboxymethyl)-1-methyl-3-(3-(4-octylphenyl) ureido)pyrrolidinium 2,2,2-trifluoroacetate According to the method described in example 13b, benzyl 2-(1-methyl-3-(3-(4-octylphenyl)ureido)pyrrolidin-3-yl)acetate was hydrolyzed with sodium hydroxide to give the title compound as a white solid (2.7 mg, 8%). $^1$H NMR (400 MHz, CD$_3$OD) δ 7.26 (d, 2H, J=7.9 Hz), 7.08 (d, 2H, J=8.1 Hz), 4.22-3.84 (m, 2H), 3.22-2.87 (m, 6H), 2.57-2.40 (m, 4H), 1.60-1.57 (m, 2H), 1.31-1.23 (m, 12H), 0.90 (t, 3H, J=6.6 Hz); MS ESI 390.3 [M+H]$^+$, calcd for [C$_{22}$H$_{35}$N$_3$O$_3$+H] 390.27.

Example S18

3-(carboxymethyl)-1,1-dimethyl-3-(3-(4-octylphenyl)ureido)-pyrrolidinium 2,2,2-trifluoroacetate

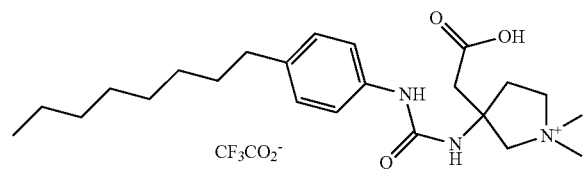

a) 3-(2-Ethoxy-2-oxoethyl)-1,1-dimethyl-3-(3-(4-octylphenyl)ureido)pyrrolidinium iodide According to the method described in example 2a, ethyl 2-(1-methyl-3-(3-(4-octylphenyl)ureido)pyrrolidin-3-yl)acetate was reacted with methyl iodide to give the title compound as a white solid (31 mg, quantitive). MS ESI 432.4 [M]$^+$, calcd for [C$_{25}$H$_{42}$N$_3$O$_3$$^+$] 432.32 b) 3-(Carboxymethyl)-1,1-dimethyl-3-(3-(4-octylphenyl)ureido)pyrrolidinium 2,2,2-trifluoroacetate According to the method described in example 13b, 3-(2-ethoxy-2-oxoethyl)-1,1-dimethyl-3-(3-(4-octylphenyl)ureido)pyrrolidinium iodide was hydrolyzed with sodium hydroxide to give the title compound as a white solid (2 mg, 7%). $^1$H NMR (400 MHz, CD$_3$OD) δ 7.24 (d, 2H, J=7.9 Hz), 7.09 (d, 2H, J=8.1 Hz), 4.32-4.31 (m, 1H), 3.84-2.76 (m, 3H), 3.35 (s, 6H) 3.15-3.10 (m, 2H), 2.79-2.72 (m, 1H), 2.57-2.50 (m, 3H), 1.60-1.57 (m, 2H), 1.31-1.23 (m, 12H), 0.90 (t, 3H, J=6.6 Hz); MS ESI 404.3 [M]$^+$, calcd for [C$_{23}$H$_{38}$N$_3$O$_3$$^+$] 404.29.

Example S19

3-(carboxymethyl)-1-methyl-3-(4-pentylphenylsulfonamido)-pyrrolidinium 2,2,2-trifluoroacetate

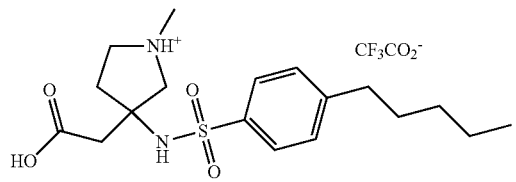 [SMILES: CCCCCc1ccc(S(=O)(=O)NC2(CC(=O)O)CC[NH+](C)C2)cc1 ; "CF3CO2-"]

a) Benzyl 3-(2-ethoxy-2-oxoethyl)-3-(4-pentylphenylsulfonamido)pyrrolidine-1-carboxylate To a solution of 3-amino-3-(2-ethoxy-2-oxoethyl)pyrrolidine-1-carboxylate (200 mg, 0.65 mmol) and 4-pentylbenzene-1-sulfonyl chloride (480 mg, 1.95 mmol) in CH$_2$Cl$_2$ (5 mL) was added triethylamine (0.23 mL, 1.95 mL) and DMAP (1 mg). The solution was stirred overnight at room temperature. Methylene chloride (100 mL) was added and the solution was washed with sat. sodium bicarbonate (10 mL), H$_2$O (10 mL) dried over MgSO4 and concentrated. The residue was purified by silica gel chromatography (EtOAc) to give the title compound as a yellow solid (120 mg, 36%).

b) ethyl 2-(3-(4-pentylphenylsulfonamido)pyrrolidin-3-yl)acetate

A solution of benzyl 3-(2-ethoxy-2-oxoethyl)-3-(4-pentylphenylsulfonamido)-pyrrolidine-1-carboxylate (120 mg, 0.23 mmol) in EtOH (5 mL) was purged with nitrogen and Pd/C (25 mg) was added and the flask was purged with hydrogen and stirred for 24 h. The mixture was filtered through celite and concentrated. The residue was dissolved into H$_2$O and lyophilized to give the title compound as a white solid (55 mg, 62%). MS ESI 383.2 [M+H]$^+$, calcd for [C$_{19}$H$_{30}$N$_2$O$_4$S+H]$^+$ 383.19.

c) ethyl 2-(1-methyl-3-(4-pentylphenylsulfonamido) pyrrolidin-3-yl)acetate

To a solution of ethyl 2-(3-(4-pentylphenylsulfonamido)pyrrolidin-3-yl)acetate (55 mg, 0.14 mmol) in formic acid (2 mL) was added formalin (15 μL, 0.16 mL). The solution was heated to 110° C. for 2 h. The mixture was concentrated and dissolved into CH$_2$Cl$_2$ (25 mL) and washed with sat. bicarbonate (2×5 mL), H$_2$O (5 mL), dried over MgSO$_4$ and concentrated to dryness to give the title compound as a brown oil (40 mg, 71%). MS ESI 397.2 [M+H]$^+$, calcd for [C$_{20}$H$_{32}$N$_2$O$_4$S+H]$^+$ 397.21.

d) 3-(carboxymethyl)-1-methyl-3-(4-pentylphenylsulfonamido)-pyrrolidinium 2,2,2-trifluoroacetate To a solution of ethyl 2-(1-methyl-3-(4-pentylphenylsulfonamido)pyrrolidin-3-yl)acetate (15 mg, 0.04 mmol) in MeOH (1 mL) was added 1 N NaOH (1 mL). The reaction was stirred for 1 h and acidified to pH 1. The mixture was purified by preparatory HPLC to give the title compound as a white solid (15 mg, 79%). $^1$H NMR (400 MHz, CD$_3$OD) δ 7.81 (d, 2H, J=8.3 Hz), 7.40 (d, 2H, J=8.3 Hz), 4.28-3.75 (m, 2H), 3.31-3.10 (m, 2H), 2.96 (s, 3H), 2.72 (t, 2H, J=7.6 Hz), 2.81-2.62 (m, 3H), 2.26-2.05 (m, 2H), 1.71-1.63 (m, 2H), 1.40-1.31 (m, 4H), 0.92 (t, 3H, J=7.1 Hz); MS ESI 369.2 [M+11]$^+$, calcd for [C$_{18}$H$_{28}$N$_2$O$_4$S+H]$^+$ 369.18.

Example S20

3-(carboxymethyl)-1,1-dimethyl-3-(4-pentylphenylsulfonamido)-pyrrolidinium 2,2,2-trifluoroacetate

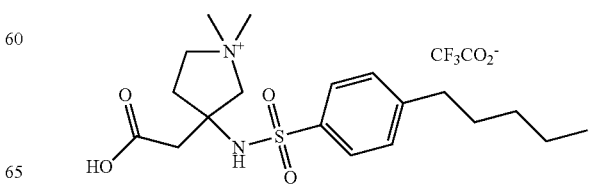

a) 3-(2-ethoxy-2-oxoethyl)-1,1-dimethyl-3-(4-pentylphenylsulfonamido)pyrrolidinium iodide To a solution of ethyl 2-(1-methyl-3-(4-pentylphenylsulfonamido)pyrrolidin-3-yl)acetate (25 mg, 0.063 mmol) in methylene chloride (1 mL) was added methyl iodide (100 μL). The solution was stirred overnight and concentrated to give the title compound as a white solid (33 mg, quantitative). ESI 411.3 [M]$^+$, calcd for [$C_{21}H_{35}N_2O_4S$]$^+$ 411.23.

b) 3-(carboxymethyl)-1,1-dimethyl-3-(4-pentylphenylsulfonamido) pyrrolidinium 2,2,2-trifluoroacetate According to the method described in example 13b, 3-(2-ethoxy-2-oxoethyl)-1,1-dimethyl-3-(4-pentylphenylsulfonamido)pyrrolidinium iodide was hydrolyzed with sodium hydroxide and purified by HPLC to give the title compound as a white solid (20 mg, 64%). $^1$H NMR (400 MHz, CD$_3$OD) δ 7.81 (d, 2H, J=8.3 Hz), 7.40 (d, 2H, J=8.3 Hz), 4.33 (d, 1H, J=13.6 Hz), 3.74-3.69 (m, 2H), 3.66 (d, 1H, J=13.7 Hz), 3.24 (s, 6H), 2.96-2.88 (m, 1H), 2.86-2.71 (m, 4H), 2.42-2.34 (m, 1H), 1.71-1.63 (m, 2H), 1.40-1.28 (m, 4H), 0.92 (t, 3H, J=7.6 Hz); MS ESI 383.2 [M+H]$^+$, calcd for [$C_{19}H_{31}N_2O_4S$+]$^+$ 383.2.

Example S21

3-(carboxymethyl)-3-(4-decylbenzamido)-1-methylpyrrolidinium 2,2,2-trifluoroacetate

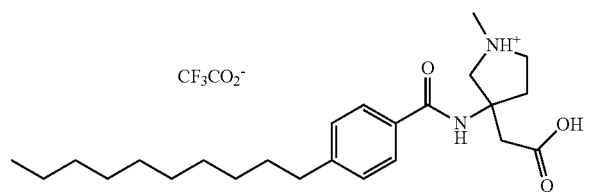 [SMILES: CCCCCCCCCCc1ccc(C(=O)NC2(CC(=O)O)CC[NH+](C)C2)cc1 ; "CF3CO2-"]

a) Benzyl 3-(4-decylbenzamido)-3-(2-ethoxy-2-oxoethyl)pyrrolidine-1-carboxylate To a solution of benzyl 3-amino-3-(2-ethoxy-2-oxoethyl)pyrrolidine-1-carboxylate (260 mg, 0.85 mmol) and p-decylbenzoic acid (267 mg, 1.03 mmol) in CH$_2$Cl$_2$ (10 mL) was added EDC (195 mg, 1.02 mmol) and triethylamine (0.35 mL, 2.55 mmol). The reaction was stirred overnight at room temperature. Methylene chloride (100 mL) was added and the solution was washed with sat. sodium bicarbonate (2×10 mL), H$_2$O (10 mL) dried over MgSO$_4$ and concentrated. The residue was purified by silica gel chromatography (9:1 CH$_2$Cl$_2$/EtOAc) to give the title compound as a yellow solid (127 mg, 26%) $^1$H NMR (400 MHz, CDCl$_3$) δ 7.64 (d, 2H, J=7.8 Hz), 7.41-7.28 (m, 5H), 7.23 (d, 2H, J=7.5 Hz), 6.40 (s, 1H), 5.21-5.10 (m, 2H), 4.10 (q, 2H, J=7.1 Hz), 4.02 (d, 1H, J=11.9 Hz), 3.64 (d, 1H, J=12.4 Hz), 3.60-3.53 (m, 2H), 3.35-2.86 (m, 2H), 2.64 (t, 2H, J=7.6 Hz), 2.14-2.02 (m, 1H), 1.67-1.56 (m, 4H), 1.36-1.24 (m, 14H), 1.21 (t, 3H, J=7.1 Hz), 0.89 (t, 3H, J=6.6 Hz).

b) Ethyl 2-(3-(4-decylbenzamido)pyrrolidin-3-yl)acetate

According to the method described in example 17b, benzyl 3-(4-decylbenzamido)-3-(2-ethoxy-2-oxoethyl)pyrrolidine-1-carboxylate was hydrogenated to give the title compound as a white solid (77 mg, 81%). MS ESI 417.4[M+H]$^+$, calcd for [$C_{25}H_{40}N_2O_3$+H] 417.30.

c) ethyl 2-(3-(4-decylbenzamido)-1-methylpyrrolidin-3-yl)acetate

According to the method described in example 17c, ethyl 2-(3-(4-decylbenzamido)-pyrrolidin-3-yl)acetate was reacted with formalin to give the title compound as a yellow oil (58 mg, 75%). $^1$H NMR (400 MHz, CDCl$_3$) δ 7.67 (d, 2H, J=7.9 Hz), 7.21 (d, 2H, J=8.1 Hz), 6.70 (s, 1H), 4.10 (q, 2H, J=7.1 Hz), 3.17-2.82 (m, 4H), 2.77-2.67 (m, 2H), 2.63 (t, 2H, J=7.8 Hz), 2.37 (s, 3H), 2.35-2.30 (m, 1H), 1.64-1.55 (m, 2H), 1.36-1.24 (m, 14H), 1.20 (t, 3H, J=7.3 Hz), 0.89 (t, 311, J=6.6 Hz); MS ESI 431.4[M+H]$^+$, calcd for [$C_{26}H_{42}N_2O_3$+H] 431.32.

d) 3-(carboxymethyl)-3-(4-decylbenzamido)-1-methylpyrrolidinium 2,2,2-trifluoroacetate According to the method described in example 13b, ethyl 2-(3-(4-decylbenzamido)-1-methylpyrrolidin-3-yl)acetate was hydrolyzed with sodium hydroxide to give the title compound as a white solid (15 mg, 55%). $^1$H NMR (400 MHz, CD$_3$OD) δ 7.75 (d, 2H, J=7.9 Hz), 7.29 (d, 2H, J=8.1 Hz), 4.20-4.15 (m, 1H), 3.80-3.37 (m, 3H), 3.17-3.03 (m, 2H), 2.99 (s, 3H), 2.74-2.63 (m, 3H), 2.44-2.37 (m, 1H), 1.64-1.55 (m, 2H), 1.36-1.24 (m, 14H), 0.90 (t, 3H, J=6.6 Hz); MS ESI 403.3 [M+H]$^+$, calcd for [$C_{24}H_{38}N_2O_3$+H] 403.3.

Example S22

3-(Carboxymethyl)-3-(4-decylbenzamido)-1,1-dimethylpyrrolidinium 2,2,2-trifluoroacetate

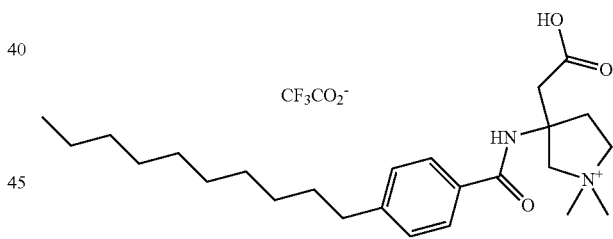

a) 3-(4-decylbenzamido)-3-(2-ethoxy-2-oxoethyl)-1,1-dimethylpyrrolidinium iodide According to the method described in example 2a, ethyl 2-(3-(4-decylbenzamido)-1-methylpyrrolidin-3-yl)acetate (35 mg, 0.08 mmol) was reacted with methyl iodide to give the title compound as a white solid (46 mg, quantitive). MS ESI 445.3 [M]$^+$, calcd for [$C_{27}H_{45}N_2O_3$$^+$] 445.34.

b) 3-(carboxymethyl)-3-(4-decylbenzamido)-1,1-dimethylpyrrolidinium 2,2,2-trifluoroacetate According to the method described in example 17b, 3-(4-decylbenzamido)-3-(2-ethoxy-2-oxoethyl)-1,1-dimethylpyrrolidinium iodide was hydrolyzed with sodium hydroxide to give the title compound as a white solid (31 mg, 74%). $^1$H NMR (400 MHz, CD$_3$OD) δ 7.74 (d, 2H, J=7.9 Hz), 7.29 (d, 2H, J=8.1 Hz), 4.50-4.47 (m, 1H), 3.90-3.75 (m, 3H), 3.29

(s, 6H), 3.23 (s, 2H), 3.02-2.95 (m, 1H), 2.72-2.66 (m, 3H), 1.66-1.62 (m, 2H), 1.36-1.28 (m, 14H), 0.90 (t, 3H, J=6.6 Hz); MS ESI 417.4 [M+H]$^+$, calcd for [C$_{25}$H$_{41}$N$_2$O$_3$+H]$^+$ 417.3.

Example S23

3-(carboxymethyl)-3-(3-(4-octylphenyl)ureido)azetidinium 2,2,2-trifluoroacetate

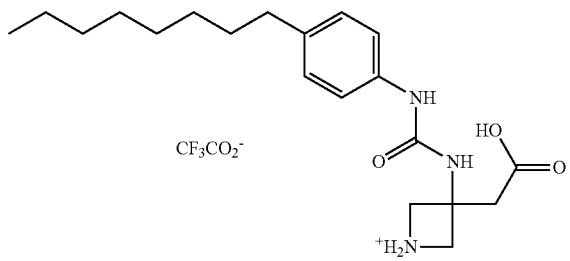 [SMILES: CCCCCCCCc1ccc(NC(=O)NC2(CC(=O)O)C[NH2+]C2)cc1 ; "CF3CO2-"]

a) tert-Butyl 3-(2-ethoxy-2-oxoethyl)-3-(3-(4-octylphenyl)ureido)azetidine-1-carboxylate A stirred solution of tert-butyl 3-amino-3-(2-ethoxy-2-oxoethypazetidine-1-carboxylate (1 equiv.), at room temperature, was treated with NEt$_3$ (3 equiv.), in CH$_2$Cl$_2$ (~0.2M) and isocyanate (1-1.5 equiv.). The reaction was stirred overnight, the solvent removed in vacuo and the product purified by column chromatography to obtained the title compound (271 mg, 63%). $^1$H NMR (400 MHz, CD$_3$OD) δ 7.22 (d, 2H, J=8.4 Hz), 7.07 (d, 2H, J=8.4 Hz), 4.15 (q, 2H, J=6.8 Hz), 4.01 (bs, 4H), 3.07 (s, 2H), 2.55 (t, 2H, J=7.6), 1.61-1.55 (m, 2H), 1.46 (s, 9H), 1.35-1.21 (m, 13H), 0.90 (t, 3H, J=6.4); MS ESI 490.4 [M+H]$^+$, calcd for [C$_{27}$H$_{43}$N$_3$O$_5$+H]$^+$ 490.65.

b) Ethyl 2-(3-(3-(4-octylphenyl)ureido)azetidin-3-yl) acetate

A solution of tent-butyl 3-(2-ethoxy-2-oxoethyl)-3-(3-(4-octylphenyl)ureido)azetidine-1-carboxylate (0.5 mmol) in CH$_2$Cl$_2$ (5 mL) was cooled with an ice/water bath and treated with trifluoroacetic acid (0.5 mL). The reaction was monitored (TLC) to completion (3-4 hrs) at which point the solvent and excess trifluoroacetic acid were removed in vacuo. The residue was purified by column chromatography to obtained the title compound (49 mg, 65%). $^1$H NMR (400 MHz, CD$_3$OD) δ 7.21 (d, 2H, J=8.4 Hz), 7.07 (d, 2H, J=8.4 Hz), 4.14 (q, 2H, J=6.8 Hz), 3.80 (d, 2H, J=9.6 Hz), 3.69 (d, 2H, J=9.6 Hz), 3.11 (s, 2H), 2.55 (t, 2H, J=7.6 Hz), 1.60-1.55 (m, 2H), 1.33-1.21 (m, 13H), 0.90 (t, 3H, J=6.4 Hz); MS ESI 390.3 [M+H]$^+$, calcd for [C$_{22}$H$_{35}$N$_3$O$_3$+H]$^+$ 390.54.

c) 3-(carboxymethyl)-3-(3-(4-octylphenyl)ureido) azetidinium 2,2,2-trifluoroacetate To a solution of ethyl 2-(3-(3-(4-octylphenyl)ureido)azetidin-3-yl)acetate (23 mg, 0.059 mmol) in 5 mL MeOH/water (4:1) was added LiOH (20 mg, 0.836 mmol), at room temperature, and the reaction was stirred overnight. The MeOH was removed in vacuo and the residue dissolved in water and subjected to reverse-phase preparatory-HPLC purification which yielded the title compound (12 mg, 43%). $^1$H NMR (400 MHz, CD$_3$OD) δ 7.27 (d, 2H, J=8.4 Hz), 7.09 (d, 2H, J=8.4 Hz), 4.41 (d, 2H, J=11.2 Hz), 4.22 (d, 2H, J=11.6 Hz), 3.05 (s, 2H), 2.56 (t, 2H, J=7.6 Hz), 1.62-1.56 (m, 2H), 1.36-1.22 (m, 10H), 0.90 (t, 3H, J=6.4 Hz); MS ESI 362.2 [M+H]$^+$, calcd for [C$_{20}$H$_{31}$N$_3$O$_3$+H]$^+$ 362.49.

Example S24

3-(Carboxymethyl)-1,1-dimethyl-3-(3-(4-octylphenyl)ureido)azetidinium 2,2,2-trifluoroacetate

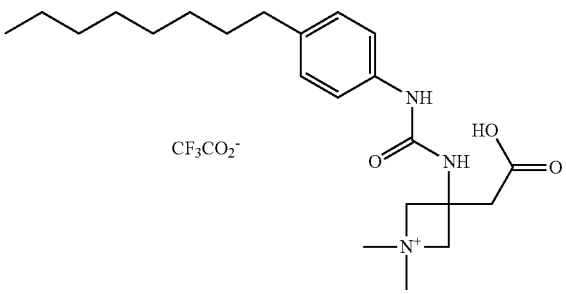 [SMILES: CCCCCCCCc1ccc(NC(=O)NC2(CC(=O)O)C[N+](C)(C)C2)cc1 ; "CF3CO2-"]

A solution of ethyl 2-(3-(3-(4-octylphenyl)ureido)azetidin-3-yl)acetate in DMF was treated with K$_2$CO$_3$ (2.5 equiv.) and MeI (10-20 equiv.) and stirred overnight. The solvent and volatiles were removed in vacuo to yield crude 3-(2-ethoxy-2-oxoethyl)-1,1-dimethyl-3-(3-(4-octylphenyl)ureido)azetidinium iodide; the residue was dissolved with MeOH/water (4:1); LiOH (10 equiv.) was added and the reaction mixture was stirred overnight. The MeOH was removed in vacuo and the residue diluted with water and purified by reverse-phase preparatory HPLC which gave the title compound as trifluoroacetate (TFA) salts. $^1$H NMR (400 MHz, CD$_3$OD) δ 7.44 (d, 2H, J=8.4 Hz), 7.18 (d, 2H, J=8.4 Hz), 3.97 (dd, 2H, J=35.2 Hz, J=10.4 Hz), 3.55 (s, 2H), 3.02 (s, 6H), 2.86 (s, 2H), 2.59 (t, 2H, J=7.2), 1.63-1.57 (m, 2H), 1.34-1.27 (m, 10H), 0.90 (t, 3H, J=6.4); [M+H]$^+$, calcd for [C$_{22}$H$_{36}$N$_3$O$_3$+H]$^+$ 390.54.

Example S25

3-(carboxymethyl)-3-(4-pentylphenylsulfonamido) azetidinium 2,2,2-trifluoroacetate

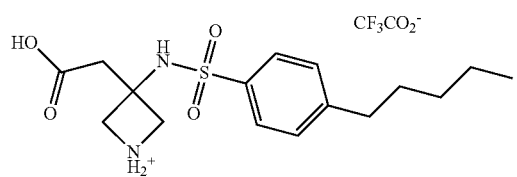 [SMILES: CCCCCc1ccc(S(=O)(=O)NC2(CC(=O)O)C[NH2+]C2)cc1 ; "CF3CO2-"]

a. tert-Butyl 3-(2-ethoxy-2-oxoethyl)-3-(4-pentylphenylsulfonamido)azetidine-1-carboxylate Ethyl 2-(3-aminoazetidin-3-yl)acetate (150 mg, 0.58 mmol) was dissolved into DCM (5 mL). The solution was treated with triethylamine (0.24 mL, 1.74 mmol) and DMAP (7.1 mg, 0.058 mmol) followed by 4-pentylbenzene-1-sulfonyl chloride (429 mg, 1.74 mmol). The mixture was stirred overnight at room temperature. Methylene chloride (75 mL) was added and the solution was washed with saturated sodium bicarbonate (2×10 mL), water (20 mL), dried over MgSO$_4$ and concentrated. The residue was loaded onto a silica gel column and eluted with 1:4 EtOAc/hexane to obtain the title compound as a white powder (119 mg, 44%). $^1$H NMR (400 MHz, CDCl$_3$) δ 7.77 (d, 2H, J=8 Hz), 7.32 (d, 2H, J=8 Hz), 5.59 (s, 1H), 4.12 (d, 2H, J=9.2 Hz), 4.05 (q, 2H, J=7.2 Hz), 3.76 (d, 2H, J=7.2 Hz), 2.96 (s, 2H), 2.68 (t, 2H, J=8 Hz), 1.68-1.62 (m, 2H), 1.42 (s, 9H), 1.34 (bs, 4H), 1.22 (t, 3H, J=7.2 Hz), 0.93 (t, 3H, J=6.8 Hz).

b. ethyl 2-(3-(4-pentylphenylsulfonamido)azetidin-3-yl)acetate tert-Butyl 3-(2-ethoxy-2-oxoethyl)-3-(4-pentylphenylsulfonamido)azetidine-1-carboxylate (79 mg, 0.169 mmol) was dissolved into DCM (4 mL). The solution was treated with TFA (0.3 mL). The mixture was stirred at room temperature for 4 h. DCM was removed under vacuum. Ethyl acetate (25 mL) was added and the solution was washed with saturated sodium bicarbonate (2×5 mL), water (10 mL), brine (10 mL), dried over MgSO$_4$ and concentrated to afford the title compound as a white powder (52 mg, 84%). $^1$H NMR (400 MHz, CDCl$_3$) δ 7.79 (d, 2H, J=8 Hz), 7.31 (d, 2H, J=8 Hz), 4.05 (q, 2H, J=7.2 Hz), 3.94 (d, 2H, J=8.8 Hz), 3.36 (d, 2H, J=8.8 Hz), 3.01 (s, 2H), 2.68 (t, 2H, J=8 Hz), 1.66 (m, 2H), 1.34 (br, 4H), 1.22 (t, 3H, J=7.2 Hz), 0.90 (t, 3H, J=6.8 Hz); MS ESI 369.1 [M+H]$^+$, calcd for [C$_{18}$H$_{28}$N$_2$O$_4$S+H]$^+$ 369.18.

c) 3-(carboxymethyl)-3-(4-pentylphenylsulfonamido)azetidinium 2,2,2-trifluoroacetate Ethyl 2-(3-(4-pentylphenylsulfonamido)azetidin-3-yl)acetate (20 mg, 0.053 mmol) was dissolved into 4:1 MeOH/H$_2$O (5 mL). The solution was treated with LiOH (20 mg, 0.833 mmol). The mixture was stirred at room temperature for 2 d. MeOH was removed under vacuum. The residue was purified by preparatory HPLC to afford the title compound as a white powder (11 mg, 43%). $^1$H NMR (400 MHz, D$_2$O) δ 7.66 (d, 2H, J=8 Hz), 7.35 (d, 2H, J=8 Hz), 4.25 (d, 2H, J=12 Hz), 4.10 (d, 2H, J=12 Hz), 2.84 (s, 2H), 2.61 (t, 2H, J=7.6 Hz), 1.53 (m, 6H), 1.18 (br, 4H), 0.74 (t, 3H, J=6.4 Hz); MS ESI 341.1 [M+H]$^+$, calcd for [C$_{16}$H$_{24}$N$_2$O$_4$S+H]$^+$ 341.15.

Example S26

3-(carboxymethyl)-3-(5-(phenylethynyl)furan-2-carboxamido)-azetidinium 2,2,2-trifluoroacetate

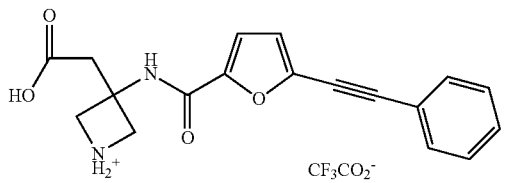

a) tert-butyl 3-(2-ethoxy-2-oxoethyl)-3-(5-(phenylethynyl)furan-2-carboxamido)-azetidine-1-carboxylate A stirred solution of tert-butyl 3-amino-3-(2-ethoxy-2-oxoethyl)azetidine-1-carboxylate (130 mg, 0.503 mmol) in DMF (3 mL) was treated with NEt$_3$ (0.19 mL, 1.37 mmol), and 2,5-dioxopyrrolidin-1-yl 5-(phenylethynyl)furan-2-carboxylate, prepared as described in Preparation 5 (141 mg, 0.457 mmol). The reaction was stirred overnight, at room temperature, then the solvent removed in vacuo and the crude product purified by column chromatography to obtain the title compound (168 mg, 81%). $^1$H NMR (400 MHz, CDCl$_3$) δ 7.57 (m, 2H), 7.40 (m, 3H), 7.12 (s, 1H), 7.04 (s, 1H), 6.70 (s, 1H), 4.17 (m, 4H), 4.03 (d, 2H, J=9.6 Hz), 3.17 (s, 2H), 1.45 (s, 9H), 1.26 (t, 3H, J=7.2 Hz); MS ESI 453.2 [M+H]$^+$, calcd for [C$_{25}$H$_{28}$N$_2$O$_6$+H]$^+$ 453.51.

b) 3-(2-ethoxy-2-oxoethyl)-3-(5-(phenylethynyl)furan-2-carboxamido)azetidinium chloride According to the method described in Example 23 (b), tert-butyl 3-(2-ethoxy-2-oxoethyl)-3-(5-(phenylethynyl)furan-2-carboxamido)azetidine-1-carboxylate (104 mg, 0.230 mmol) was treated with TFA to give the title compound as an off-white solid (45 mg, 45%). $^1$H NMR (400 MHz, CD$_3$OD) δ 7.54 (m, 2H), 7.43 (m, 3H), 7.24 (s, 1H), 6.87 (s, 1H), 4.48 (d, 2H, J=11.6 Hz), 4.32 (d, 2H, J=12 Hz), 4.19 (q, 2H, J=7.2 Hz), 3.20 (s, 2H), 1.26 (t, 3H, J=7.2 Hz); MS ESI 353.1 [M]$^+$, calcd for [C$_{20}$H$_{21}$N$_2$O$_4$]$^+$ 353.39.

c) 3-(carboxymethyl)-3-(5-(phenylethynyl)furan-2-carboxamido)azetidinium 2,2,2-trifluoroacetate Saponification of ethyl 2-(3-(5-(phenylethynyl)furan-2-carboxamido)azetidin-3-yl)acetate hydrochloride salt (7 mg, 0.018 mmol) as described in example 1b using LiOH (20 mg, 0.5 mmol) and MeOH (4 mL) and H$_2$O (1 mL), followed by preparative HPLC purification of the product gave the title compound (5.5 mg, 70%) as white solid. $^1$H NMR (400 MHz, CD$_3$OD) 7.54 (d, 2H, J=8.0 Hz), 7.47-7.39 (m, 3H), 7.24 (dd, 1H, J=3.6 Hz, 1.2 Hz), 6.87 (dd, 1H, J=3.6 Hz, 1.2 Hz), 4.48 (d, 1H, J=11.6 Hz), 4.32 (d, 1H, J=11.6 Hz), 3.16 (s, 2H); MS ESI 325.1 [M+H]$^+$, calcd for [C$_{18}$H$_{16}$N$_2$O$_4$+H]$^+$ 325.12.

Example S27

3-(carboxymethyl)-1-methyl-3-(4-pentylphenylsulfonamido)azetidinium 2,2,2-trifluoroacetate

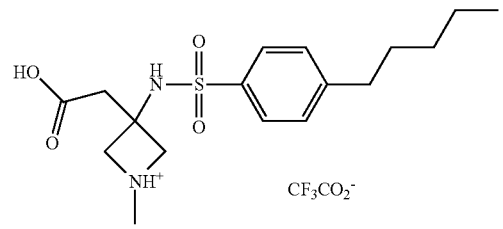

a) Ethyl 2-(1-methyl-3-(4-pentylphenylsulfonamido)azetidin-3-yl)acetate

Ethyl 2-(3-(4-pentylphenylsulfonamido)azetidin-3-yl)acetate (35 mg, 0.095 mmol) was dissolved into formic acid (2 mL). The solution was treated with formaldehyde (16 mg of 36% solution, 0.19 mmol). The mixture was stirred at 110° C. for 2 h. Solvent was removed under vacuum. The residue was added CH$_2$Cl$_2$ (10 mL) and washed with saturated sodium bicarbonate (3×5 mL) and H$_2$O (10 mL) dried over MgSO$_4$ and concentrated. The residue was loaded onto a silica gel column and eluted with EtOAc/hexane (30% to 50%) to obtain the title compound as a white powder (20 mg, 55%). $^1$H NMR (400 MHz, CDCl$_3$) δ 7.76 (d, 2H, J=7.6 Hz), 7.30 (d, 2H, J=7.6 Hz), 4.03 (q, 2H, J=7.2 Hz), 3.36 (d, 2H, J=7.2 Hz), 3.23 (d, 2H, J=7.2 Hz), 2.95 (s, 2H), 2.68 (t, 2H, J=7.6 Hz), 2.30 (s, 3H), 1.67-1.60 (m, 2H), 1.33 (br, 4H), 1.19 (t, 3H, J=7.2 Hz), 0.92 (m, 3H); MS ESI 383.2 [M+H]$^+$, calcd for [C$_{19}$H$_{30}$N$_2$O$_4$S+H]$^+$383.20.

b) 3-(carboxymethyl)-1-methyl-3-(4-pentylphenyl-sulfonamido)-azetidinium 2,2,2-trifluoroacetate According to the method described in example 25, ethyl 2-(1-methyl-3-(4-pentylphenylsulfonamido)azetidin-3-yl) acetate was reacted with LiOH, and the product was purified by preparatory HPLC, to give the title compound as a white powder (8.3 mg, 68%). $^1$H NMR (400 MHz, D$_2$O) δ 7.65 (m, 2H), 7.34 (m, 2H), 4.49-4.37 (dd, 2H, J=12.4, 35.2 Hz), 4.12-4.03 (dd, 2H, J=12.4, 35.2 Hz), 2.86 (d, 3H, J=37.6 Hz), 2.75 (d, 2H, J=12.4 Hz), 2.59 (t, 2H, J=7.2 Hz), 1.51 (m, 2H), 1.20 (m, 4H), 0.74 (m, 3H); MS ESI 355.2 [M+H]$^+$, calcd for [C$_{17}$H$_{26}$N$_2$O$_4$S+H]$^+$ 355.17.

Example S28

3-(carboxymethyl)-3-(N-(4-octylphenyl)sulfamoy-lamino)azetidinium 2,2,2-trifluoroacetate

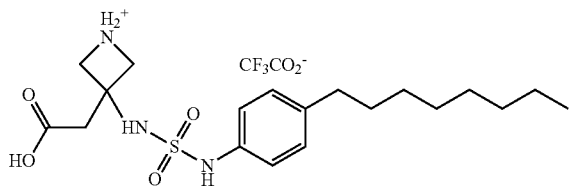

a) Ethyl 2-(3-(N—O-octylphenyl)sulfamoylamino) azetidin-3-yl)acetate

A solution of 2-chloroethyl N-(4-octylphenyl)sulfamoyl-carbamate (467 mg, 1.2 mmol), Et$_3$N (0.42 mL, 3 mmol) and tert-butyl 3-amino-3-(2-ethoxy-2-oxoethyl)azetidine-1-carboxylate (258 mg, 1 mmol) in CH$_3$CN (20 mL) was refluxed for 4 h. and cooled. After removal of the solvent in vacuo, the residue was dissolved in dichloromethane (60 mL) and washed with sat. NaHCO$_3$ (10 mL×2) and dried (Na$_2$SO$_4$). After evaporation, the residue was redissolved in dichlormethane (10 mL) and treated with trifluoroacetic acid (2 mL). The reaction mixture was stirred for 2 h at rt. After evaporation, the residue was diluted with dichloromethane (60 mL) and washed with sat. NaHCO$_3$ (10 mL×2), brine, dried (Na$_2$SO$_4$) and evaporated to give yellow oil which was purified by flash chromatography (EtOAc to EtOAc/MeOH 10:1) to give the title compound (75 mg, 18%) as light yellow oil which was used without further purification. MS ESI 426.2 [M+H]$^+$, calcd for [C$_{21}$H$_{35}$N$_3$O$_4$S+H]$^+$ 426.24.

b) 3-(carboxymethyl)-3-(N-(4-octylphenyl)sulfa-moylamino)azetidinium 2,2,2-trifluoroacetate Saponification of ethyl 2-(3-(N-(4-octylphenyl)sulfamoy-lamino)azetidin-3-yl)acetate (8 mg, 0.019 mmol) as described in example 1b using 1 M NaOH and MeOH, followed by preparative HPLC purification of the product gave the title compound (6.0 mg, 64%) as white solid. $^1$H NMR (400 MHz, CD$_3$OD) δ 7.14 (s, 4H), 4.33 (d, 2H, J=11.6 Hz), 4.16 (d, 2H, J=12.0 Hz), 3.10 (s, 2H), 1.65-1.55 (m, 2H), 1.40-1.23 (m, 10H), 0.90 (t, 3H, J=6.8 Hz); MS ESI 398.2 [M+H]$^+$, calcd for [C$_{19}$H$_{31}$N$_3$O$_4$S+H]$^+$398.21.

Example S29

3-(carboxymethyl)-1,1-dimethyl-3-(4-pentylphenyl-sulfonamido)-azetidinium 2,2,2-trifluoroacetate

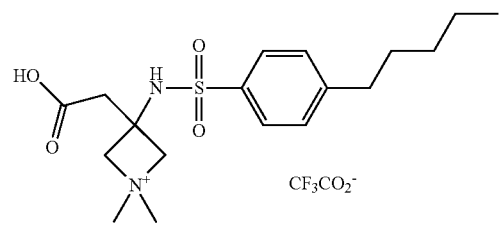

a) 3-(2-ethoxy-2-oxoethyl)-1,1-dimethyl-3-(4-pen-tylphenylsulfonamido)-azetidinium iodide Ethyl 2-(1-methyl-3-(4-pentylphenylsulfonamido)azeti-din-3-yl)acetate (10 mg, 0.026 mmol) was dissolved into CH$_2$Cl$_2$ (2 mL). The solution was treated with methyl iodide (37 mg, 0.26 mmol). The mixture was stirred at room temperature overnight. Solvent was removed under vacuum to obtain the title compound as a yellow solid (10 mg, 77%) which was used in the next step without purification. $^1$H NMR (400 MHz, CDCl$_3$) δ 7.83 (d, 2H, J=8 Hz), 7.33 (d, 2H, J=8 Hz), 5.04 (m, 4H), 3.90 (q, 2H, J=7.2 Hz), 3.64 (s, 3H), 3.58 (m, 3H), 3.14 (s, 2H), 2.66 (t, 2H, J=8 Hz), 1.65-1.58 (m, 2H), 1.32 (br, 4H), 1.10 (t, 3H, J=7.2 Hz), 0.89 (m, 3H); MS ESI 397.2 [M]$^+$, calcd for [C$_{20}$H$_{33}$N$_2$O$_4$S]$^+$ 397.22.

b) 3-(carboxymethyl)-1,1-dimethyl-3-(4-pentylphe-nylsulfonamido)azetidinium trifluororacetate According to the method described in example S25c, 3-(2-ethoxy-2-oxoethyl)-1,1-dimethyl-3-(4-pentylphenylsulfona-mido)azetidinium iodide was reacted with LiOH to give the title compound as a white powder (1.8 mg, 20%).

1H NMR (400 MHz, D$_2$O) δ 7.65 (d, 2H, J=8 Hz), 7.34 (d, 2H, J=8 Hz), 4.65-4.49 (m, 4H), 3.29 (s, 3H), 3.10 (s, 3H), 2.81 (s, 2H), 2.60 (t, 2H, J=7.6 Hz), 1.55-1.48 (m, 2H), 1.17 (br, 4H), 0.75 (t, 3H, J=6.4 Hz); MS ESI 369.2 [M—CF$_3$COO]$^+$, calcd for [C$_{18}$H$_{29}$N$_2$O$_4$S]$^+$ 369.18.

Example S30

3-(carboxymethyl)-1,1-dimethyl-3-(N-methyl-N-(4-octylphenyl)-sulfamoylamino)piperidinium 2,2,2-trifluoroacetate

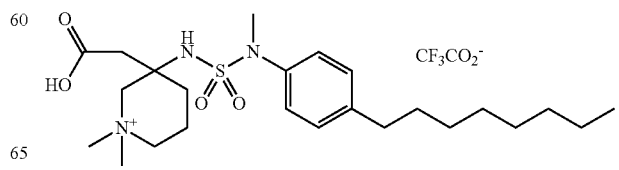

a) Methyl 2-(1-methyl-3-(N-methyl-N-(4-octylphenyl)sulfamoylamino)piperidin-3-yl)acetate To a solution of methyl 2-(3-amino-1-methylpiperidin-3-yl)acetate (186 mg, 1 mmol) and Et$_3$N (0.42 mL, 3 mmol) in CH$_2$Cl$_2$ was added the solution of 2-chloroethyl chlorosulfonylcarbamate in CH$_2$Cl$_2$ (0.77 M, 1.3 mL, 1 mmol). After addition, the resulting mixture was stirred overnight at rt. Evaporation of solvents gave a light yellow oil which was used without further purification. A solution of this crude mixture, N-methyl-4-octylaniline (241 mg, 1.1 mmol) and Et$_3$N (0.42 mL, 3 mmol) in CH$_3$CN (10 mL) was refluxed for 2 h. After cooling to rt and evaporating solvents, the residue was purified by a short column (EtOAc/hexance=10:1) to give the title compound (105 mg, 22%) as white solid. MS ESI 468.3 [M+H]$^+$, calcd for [C$_{24}$H$_{41}$N$_3$O$_4$S+H]$^+$ 468.29.

b) 3-(carboxymethyl)-1,1-dimethyl-3-(N-methyl-N-(4-octyl-phenyl)sulfamoylamino)-piperidinium 2,2,2-trifluoroacetate To a solution of methyl 2-(1-methyl-3-(N-methyl-N-(4-octylphenyl) sulfamoylamino) piperidin-3-yl)acetate (80 mg, 0.17 mmol) in CH$_2$Cl$_2$ (8 mL) was added iodomethane (0.2 mL). The resulting mixture was stirred O/N at rt. Additional CH$_3$I (0.1 mL) was added and after stirring 8 h, additional CH$_3$I (0.1 mL) was added. The resulting mixture was stirred O/N and concentrated to give a white solid which was redissolved in MeOH (15 mL). 1 M NaOH (3 mL, 3 mmol) was added and the mixture was stirred O/N at rt. After removal of MeOH and acidifying with 2 M HCl to slightly acidic, it was purified by preparative HPLC to give the title compound (32 mg, 32%) as white solid in TFA salt form. $^1$H NMR (400 MHz, CD$_3$OD) δ 7.37 (d, 2H, J=8.0 Hz), 7.22 (d, 2H, J=8.0 Hz), 4.04 (d, 1H, J=14.0 Hz), 3.45 (d, 1H, J=12.0 Hz), 3.28-3.15 (m, 4H, including s, 3H), 3.10 (s, 3H), 3.00 (s, 3H), 2.85-2.55 (m, 5H), 2.14-2.00 (m, 1H), 1.81 (d, 1H, J=14.8 Hz), 1.70-1.52 (m, 3H), 1.40-1.20 (m, 10H), 0.91 (t, 3H, J=6.4 Hz); MS ESI 468.3 [M+H]$^+$, calcd for [C$_{24}$H$_{41}$N$_3$O$_4$S+H]$^+$

Example 2

Expression and Preparation of CPT1 Proteins

Nucleotide sequences encoding human CPT1 enzymes were individually cloned into the yeast expression vector pESC-trp at the Cla1 (5' terminus) and Pac1 (3' terminus) restriction sites by PCR amplification of the open reading frame using oligonucleotide primers designed to encode the wild-type CPT1 protein sequence. Standard molecular biology techniques were used to transform and express the CPT1 proteins in the yeast *Saccharomyces cerevisiae*. The yeast cells were lysed by enzymatic degradation of the cell wall by Zymolase, and the mitochondria were isolated by standard biochemical techniques. The integrity of the isolated mitochondria was monitored by determining the activity of succinate dehydrogenase in the mitochondrial preparations. The mitochondrial extracts were stored at −80° C. in buffer containing 10 mM HEPES pH 7.4 and 250 mM sucrose.

Human CPT1 (A, B, C) genes were additionally cloned into the pCDNA3.1 vector individually for expression in cultured mammalian cells. Cells expressing the exogenous CPT1A were identified and grown under standard conditions. Mammalian cells were harvested, and mitochondrial extracts prepared using standard biochemical methods. The mitochondrial extracts were stored at −80° C. in buffer containing 10 mM HEPES pH 7.4 and 250 mM sucrose.

Example 3

Human CPT1A LC/MS Assay

Assays were performed in 96-well plate format. Each 100 μL reaction contained 40 mM KCl, 50 mM TrisHCl pH 7.5, and 250 mM mannitol (Assay Buffer), and 1.6 μg protein of an extract, 20 μM palmitoyl-CoA, 50 μM L-carnitine, and 10 ug/mL BSA. Reactions were incubated at room temperature and stopped after 10 minutes by extraction with 200 μL of water saturated n-butanol containing myristoyl carnitine (500 nM) as an internal standard. The samples were thoroughly mixed, and the phases separated by centrifugation. Samples were prepared for analysis with a 10 fold dilution of the n-butanol phase containing the reaction product palmitoyl carnitine into a 50:50 (acetonitrile:water) solvent for analysis. 5 μL of prepared sample was separated on a Phenomenex Jupiter 5μ C4 reverse-phase column using an Agilent 1100 HPLC with a gradient from 50% acetonitrile (0.5% acetic acid) to 100% acetonitrile and quantified by detection with a Bruker Esquire 3000plus mass spectrometer. The abundance of the palmitoyl carnitine product was determined relative to the internal standard and the actual quantity of palmitoyl carnitine can be determined from a standard curve prepared using the n-butanol solution containing the internal standard.

Compounds were evaluated in two formats, a screening format, and a dose response format. The screening format was performed by adding 25 μL compound in 20% DMSO and Assay Buffer to 25 μL of extract containing 100 μM carnitine and Assay Buffer, followed by a 10 minute incubation at room temperature. 50 μL of 40 μM palmitoyl-CoA in Assay Buffer was added to the reaction mixture, mixed and incubated for 10 minutes at room temperature. A negative control for activity was also performed where the carnitine was omitted from the reaction. A positive control for activity was also performed by omitting compound from the solution containing 20% DMSO and Assay Buffer. The reaction mixture was extracted and analyzed as described above. The inhibition by compound was determined by comparing the control relative activity to the relative activity observed in wells containing the compound. Relative activity was determined by subtracting the relative intensity (area palmitoyl carnitine/area myristoyl carnitine) observed in the negative control from the relative intensity observed in the experimental well, and dividing by the relative activity observed in the positive control.

$$\% \text{ Inhibition} = 1 - \left( \frac{(\text{Experimental Target}/ISTD \text{ ratio})}{(\text{Negative Control Target}/ISTD \text{ ratio})} \bigg/ \frac{(\text{Positive Control Target}/ISTD \text{ ratio})}{(\text{Negative Control Target}/ISTD \text{ ratio})} \right) \times 100$$

Compound characterization by dose response format was performed using the above described assay conditions and a 16 point compound titration in 2 fold compound dilution steps. The DMSO concentration was kept constant at 20% (v/v) for all compound concentrations. The inhibitory activity of a compound was determined using an iterative 4 parameter logistic non linear curve fitting method, and the concentration of compound that inhibits the enzyme reaction by 50% is defined as the IC$_{50}$.

$y=(A+(B/(1+((x/C)^\wedge D))))$ where $A$=background activity

B=dynamic range

C=x value at inflection point

D=stoichiometry parameter

Using the dose response assay the $IC_{50}$ for L-aminocarnitine was determined to be 7.0±2.5 µM (n=17). Similarly, using the dose response assay, the compounds of this invention were determined to have $IC_{50}$ values of less than or equal to about 5 millimolar and greater than 10 nanomolar.

The results of human CPT1A LC/MS assayes are summarized in Table 1 below. In Table 1, $IC_{50}$ values are indicated as "A," "B," "C," "D," "E" and "F" for those of less than or equal to 1 µM; those of greater than 1 µM, and less than or equal to 10 µM; those of greater than 10 µM, and less than or equal to 100 µM; those of greater than 100 µM, and less than or equal to 1,000 µM; those of greater than 1,000 µM, and less than or equal to 2,500 µM those of greater than 2,500 µM, respectively. As shown in Table 1, numerous compounds of the invention were shown to be CPT1A inhibitors.

TABLE 1

$IC_{50}$ Data of CPT1A Inhibitors of the Invention

| Compounds | $IC_{50}$ |
|---|---|
| Example S13. 3-(carboxymethyl)-1-methyl-3-(5-phenethylfuran-2-carboxamido)-piperidinium 2,2,2-trifluoroacetate | D |
| Example S14: 3-(carboxymethyl)-1,1-dimethyl-3-(5-phenethylfuran-2-carboxamido) piperidinium 2,2,2-trifluoroacetate | C |
| Example S9. 3-(Carboxymethyl)-1-methyl-3-(3-(4-octylphenyl)ureido)piperidinium 2,2,2-trifluoroacetate | C |
| Example S10. 3-(carboxymethyl)-1,1-dimethyl-3-(3-(4-octylphenyl)ureido)-piperidinium 2,2,2-trifluoroacetate | C |
| Example S2. 4-(Carboxymethyl)-1,1-dimethyl-4-(3-(4-octylphenyl)ureido)piperidin-ium 2,2,2-trifluoroacetate | C |
| Example S3. 4-(carboxymethyl)-1-methyl-4-(4-pentylphenylsulfonamido)piperidinium 2,2,2-trifluoroacetate | C |
| Example S4. 4-(Carboxymethyl)-1,1-dimethyl-4-(4-pentylphenylsulfonamido)piperidin-ium 2,2,2-trifluoroacetate | A |
| Example S5. 4-(Carboxymethyl)-1,1-dimethyl-4-(5-phenethylfuran-2-carboxamido)-piperidinium 2,2,2-trifluoroacetate | B |
| Example S6. 4-(Carboxymethyl)-1,1-dimethyl-4-(5-(phenylethynyl)furan-2-carboxamido)-piperidinium 2,2,2-trifluoroacetate | D |
| Example S23. 3-(carboxymethyl)-3-(3-(4-octylphenyl)ureido)azetidinium 2,2,2-trifluoroacetate | E |
| Example S11. 3-(carboxymethyl)-1-methyl-3-(4-pentylphenylsulfonamido)piperidinium 2,2,2-trifluoroacetate | B |
| Example S12. 3-(carboxymethyl)-1,1-dimethyl-3-(4-pentylphenylsulfonamido)-piperidinium 2,2,2-trifluoroacetate | A |
| Example S15. 3-(carboxymethyl)-1-methyl-3-(N-(4-octylphenyl)sulfamoylamino)-piperidinium 2,2,2-trifluoroacetate | C |
| Example S16. 3-(carboxymethyl)-1,1-dimethyl-3-(N-(4-octylphenyl)sulfamoylamino)-piperidinium 2,2,2-trifluoroacetate | B |
| Example S24: 3-(Carboxymethyl)-1,1-dimethyl-3-(3-(4-octylphenyl)ureido)azetidinium 2,2,2-trifluoroacetate | C |
| Example S7. 4-(carboxymethyl)-1-methyl-4-(N-(4-octylphenyl)sulfamoylamino)-piperidinium 2,2,2-trifluoroacetate | C |
| Example S8. 4-(carboxymethyl)-1,1-dimethyl-4-(N-(4-octylphenyl)sulfamoylamino) piperidinium 2,2,2-trifluoroacetate | B |
| Example S25. 3-(carboxymethyl)-3-(4-pentylphenylsulfonamido)azetidinium 2,2,2-trifluoroacetate | F |

TABLE 1-continued $IC_{50}$ Data of CPT1A Inhibitors of the Invention

| Compounds | $IC_{50}$ |
|---|---|
| Example S19. 3-(carboxymethyl)-1-methyl-3-(4-pentylphenylsulfonamido)-pyrrolidinium 2,2,2-trifluoroacetate | D |
| Example S20: 3-(carboxymethyl)-1,1-dimethyl-3-(4-pentylphenylsulfonamido)pyrrolidin-ium 2,2,2-trifluoroacetate | B |
| Example S26. 3-(carboxymethyl)-3-(5-(phenylethynyl)furan-2-carboxamido)-azetidinium 2,2,2-trifluoroacetate | D |
| Example S17. 3-(carboxymethyl)-1-methyl-3-(3-(4-octylphenyl)ureido)pyrrolidinium 2,2,2-trifluoroacetate | C |
| Example S18. 3-(carboxymethyl)-1,1-dimethyl-3-(3-(4-octylphenyl)ureido)-pyrrolidinium 2,2,2-trifluoroacetate | C |
| Example S21. 3-(carboxymethyl)-3-(4-decylbenzamido)-1-methylpyrrolidinium 2,2,2-trifluoroacetate | C |
| Example S22. 3-(carboxymethyl)-3-(4-decylbenzamido)-1,1-dimethylpyrrolidinium 2,2,2-trifluoroacetate | B |
| Example S27. 3-(carboxymethyl)-1-methyl-3-(4-pentylphenylsulfonamido)azetidinium 2,2,2-trifluoroacetate | C |
| Example S28. 3-(carboxymethyl)-3-(N-(4-octylphenyl)sulfamoylamino)azetidinium 2,2,2-trifluoroacetate | F |
| Example S29. 3-(carboxymethyl)-1,1-dimethyl-3-(4-pentylphenylsulfonamido)-azetidinium 2,2,2-trifluoroacetate | C |
| Example S30. 3-(carboxymethyl)-1,1-dimethyl-3-(N-methyl-N-(4-octylphenyl)-sulfamoylamino)-piperidinium 2,2,2-trifluoroacetate | C |

Example 4

Cells and Cell Cultures

Human cancer cells (MCF-7, H358, H460, HCT116 $p53^{+/+}$, HCT116 $p53^{-/-}$, A172, PC-3, DU-145 and SW626) were maintained in DMEM medium containing 10% Fetal Bovine Serum (FBS) (Invitrogen, Burlington, ON, Canada) and normal cells HMEC, 184A1, NHBE and PrEC were cultured in MEGM, MEGM plus transferring and cholera toxin, BEGM and PrEGM supplemented with various growth factors (Cambrex, Charles city, Iowa, USA), respectively.

Example 5

Inhibition of Growth of Various Cancer Cell Lines with CPT Inhibitors of the Invention Compounds of Examples S1 to S30, and 4-(carboxymethyl)-4-(6-(3-hexyloxy)phenoxy)hexanoamido)-1,1-dimethylpiperidinium 2,2,2-trifluoroactate ("Compound A") were tested in this example. Each of the tested compounds was dissolved in DMSO and further diluted in cell culture medium for the experiments performed. Cells were seeded into 96-well plates with 1,500-5,000 cells/well according to cell growth rate. After 24 h, DMEM medium containing 10% FBS were changed to DMEM containing 3% FBS for cancer cells. The compound was added into the cell culture at the indicated concentrations, and the final concentration of DMSO was adjusted to a final concentration of 0.1%. Cell viability was assessed by Sulforhodamine B (SRB) assay at Day 6.

Sulforhodamine B (SRB) (Sigma, Oakville, ON, Canada) is a water-soluble dye that binds to the basic amino acids of the cellular proteins. Thus, colorimetric measurement of the bound dye provides an estimate of the total protein mass that is related to the cell number. The cells were fixed in situ by gently aspirating off the culture media and adding 50 ul of cold 10% Tri-chloroacetic Acid (TCA) per well and incubated at 4° C. for 30-60 min. The plates were washed five times with water and allowed to air dry for 5 min. 50 ul of 0.4% (w/v) SRB dissolved in 1% (v/v) acetic acid were added into each well, plates were then incubated at RT for 30 min for staining, washed four times with 1% acetic acid to remove any unbound dye and then allowed to air dry for 5 min. Stain was solubilized with 100 ul of 10 mM Tris pH 10.5 per well. Absorbance was read at 570 nm on a spectrophotometer. $GI_{50}$ (compound concentration required for 50% of growth inhibition) was calculated using GraphPad Prism 4.0 software (GraphPad Software, Inc., San Diego, Calif., USA). Growth inhibition (%) was determined as percentage of cells remaining compared to the DMSO-treated cells as control.

The results are shown in Table 2 and Table 3 for the compounds of Examples S1 to S30, and compound A. The values shown were obtained from triplicated experimental data.

TABLE 2

$GI_{50\ Data}$ of CPT Inhibitors of the Invention

| | | Ex. S15 | Ex. S7 | Ex. S2 | Ex. S16 | Ex. S10 | Ex. S23 | Ex. S24 |
|---|---|---|---|---|---|---|---|---|
| Breast | MCF-7 | 15 mM | 27 mM | 10 mM | 3.9 mM | 5.1 mM | 26 mM | 27 mM |
| | MDA-231 | NT | NT | NT | 0.5 mM | NT | NT | NT |
| | Hs578T | 25 mM | >50 mM | 50 mM | 17 mM | 39 mM | 45 mM | 46 mM |
| Lung | H358 | 12 mM | 20 mM | 3.1 mM | 1.4 mM | 1.0 mM | 14 mM | 19 mM |
| | A549 | 7.5 mM | 52 mM | 99 mM | 6.2 mM | 73 mM | >50 mM | 36 mM |
| | H460 | NT | NT | 1.8 mM | NT | NT | NT | NT |
| Colon | COLO-205 | 21 mM | 74 mM | 1.3 mM | 10 mM | 1.0 mM | 35 mM | 28 mM |
| | HCT-15 | 32 mM | 80 mM | 3.0 mM | 36 mM | 16 mM | 28 mM | 38 mM |
| | SW480 | 36 mM | 68 mM | 0.7 mM | 4.0 mM | 0.7 mM | 28 mM | 29 mM |
| | SW620 | 27 mM | >50 mM | 2.0 mM | 20 mM | 2.5 mM | 43 mM | 44 mM |
| Brain | A172 | 2.7 mM | 15 mM | 1.8 mM | 1.1 mM | 4.6 mM | 7.2 mM | 41 mM |
| | TOV-21G | NT | NT | NT | NT | NT | NT | NT |
| Prostate | PC-3 | 2.8 mM | 6.0 mM | 8.2 mM | 2.1 mM | 0.9 mM | 24 mM | 21 mM |
| Ovarian | SW626 | 33 mM | >50 mM | 2.5 mM | 18 mM | 2.7 mM | 21 mM | 63 mM |
| | Caov-3 | 4.0 mM | 22 mM | NT | 2.5 mM | NT | 17 mM | 45 mM |

| | | Ex. S29 | Ex. S30 | Ex. S4 | Ex. S8 | Ex. S18 | Comp. A |
|---|---|---|---|---|---|---|---|
| Breast | MCF-7 | 44 mM | 3.1 mM | NT | 2.0 mM | 5.9 mM | 14 mM |
| | MDA-231 | >50 mM | NT | NT | NT | NT | >50 mM |
| | Hs578T | >50 mM | 3.0 mM | NT | 26 mM | 26 mM | >50 mM |
| Lung | H358 | 86 mM | 2.9 mM | NT | 0.9 mM | 2.7 mM | 0.4 mM |
| | A549 | >50 mM | 1.0 mM | NT | 10 mM | 38 mM | >50 mM |
| | H460 | NT | NT | NT | NT | 2.2 mM | NT |
| Colon | COLO-205 | 28 mM | 1.6 mM | >50 mM | 5.3 mM | 1.9 mM | 9.3 mM |
| | HCT-15 | >50 mM | 14 mM | >50 mM | 9.0 mM | 5.4 mM | >50 mM |
| | SW480 | >50 mM | 3.5 mM | >50 mM | 2.8 mM | 1.2 mM | 16 mM |
| | SW620 | >77 mM | 3.5 mM | >50 mM | 8.4 mM | 3.1 mM | 49 mM |
| Brain | A172 | >50 mM | 0.6 mM | >50 mM | 2.2 mM | 1.9 mM | >50 mM |
| | TOV-21G | NT | NT | 44 mM | NT | NT | NT |
| Prostate | PC-3 | >50 mM | 0.7 mM | >50 mM | 1.7 mM | 6.6 mM | 1.5 mM |
| Ovarian | SW626 | >50 mM | 21 mM | NT | 15 mM | 3.9 mM | 12 mM |
| | Caov-3 | NT | NT | NT | 2.0 mM | NT | 0.6 mM |

NT: not tested

TABLE 3

Percentage of Growth Inhibition of CPT Inhibitors (at 10 μM) of the Invention

| | | Ex. S1 | Ex. S12 | Ex. S13 | Ex. S14 | Ex. S25 | Ex. S26 | Ex. S27 | Ex. S28 |
|---|---|---|---|---|---|---|---|---|---|
| Breast | MCF-7 | 0.120413 | 0.23515 | NT | NE | 0.14515 | 0.1403 | 0.05347 | 0.04154 |
| | MDA-231 | NT | NT | NT | NT | NT | NT | NT | 0.13384 |
| Lung | H358 | 0.432362 | 0.04495 | NT | 0.39194 | 0.05754 | 0.14368 | 0.07312 | 0.06989 |
| | A549 | NT | NT | NT | NT | NT | NT | 0.06854 | NE |
| | H460 | NT | NT | NT | NT | NT | NT | 0.00556 | NE |
| Colon | COLO-205 | 0.072871 | 0.12811 | NT | NE | NE | 0.18922 | NE | NE |
| | HCT-15 | 0.059106 | NE | NT | NE | 0.00572 | NE | NT | NT |
| | SW480 | 0.084588 | NE | NT | NE | NE | 0.04449 | NT | NT |
| | SW620 | 0.043447 | NE | NT | 0.04122 | NE | 0.0551 | NE | NE |
| | HCT-8 | NT | NT | NT | NT | NT | NT | 0.09153 | 0.06675 |
| Brain | A172 | 0.157052 | 0.07689 | NT | NE | NE | NE | NE | 0.30769 |
| Prostate | PC-3 | 0.192404 | NE | NT | NE | NE | NE | 0.0865 | 0.60429 |
| Ovarian | SW626 | 0.051417 | 0.00486 | NT | NE | 0.07606 | 0.07378 | NE | 0.04727 |

| | | Ex. S3 | Ex. S5 | Ex. S6 | Ex. S9 | Ex. S19 | Ex. S20 | Ex. S22 | Ex. S21 | Ex. S17 |
|---|---|---|---|---|---|---|---|---|---|---|
| Breast | MCF-7 | 0.007318 | 0.02312 | 0.03714 | 0.02731 | 0.08166 | 0.22689 | 0.06486 | 0.01838 | 0.20385 |
| Lung | H358 | 0.463779 | 0.08927 | 0.10737 | NT | NE | 0.27734 | 0.8129 | 0.68016 | 0.66359 |
| | A549 | NT | NT | NT | 0.451 | NT | NT | NT | NT | NT |

TABLE 3-continued

Percentage of Growth Inhibition of CPT Inhibitors (at 10 μM) of the Invention

| Colon | COLO-205 | 0.034242 | 0.12194 | 0.15431 | 0.28521 | NE | 0.36469 | 0.08112 | 0.02151 | 0.11451 |
|---|---|---|---|---|---|---|---|---|---|---|
|  | HCT-15 | 0.065146 | NE | NE | NE | NE | NE | 0.07473 | 0.04235 | 0.03874 |
|  | SW480 | 0.038296 | NE | 0.03677 | 0.00756 | NE | 0.02596 | 0.61412 | 0.09568 | 0.51905 |
|  | SW620 | 0.03948 | 0.05572 | 0.05805 | 0.04904 | NE | 0.01263 | 0.2089 | 0.07327 | 0.06799 |
| Brain | A172 | NE | 0.01342 | 0.05672 | NE | NE | 0.11755 | 0.12492 | 0.14167 | 0.16059 |
| Prostate | PC-3 | NE | NE | 0.03591 | 0.25848 | NE | NE | 0.44356 | 0.15622 | 0.77126 |
| Ovarian | SW626 | NE | 0.03032 | 0.20836 | 0.02424 | NE | 0.07399 | 0.21981 | 0.15399 | 0.35453 |

As can be seen from Tables 2 and 3, a number of compounds of the invention were tested against cancer cell lines from breast, lung, colon, brain, prostate and ovarian cancer. All of the compounds shown in Tables 2 and 3 had activity against at least one cell line ("NT" means not tested; and "NE" means no activity at 10 micromolar—activity at higher concentrations was not measured). Compound S11 was not tested against MDA-231, A549 and H460, HCT-8 cell lines and did not exihibit activity at 10 μM against the other cell lines.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula or a pharmaceutically acceptable salt thereof:

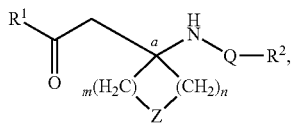

wherein
$R^1$ is —OH or —$OC_{1-6}$ alkyl;
Z is —$N^+(R^4R^5)X^-$—;
Q is —C(=O)—, —C(O)NH—, —S(O)$_2$—, —S(O)$_2$—NH—, or —S(O)$_2$—N($R^3$)—;
each of $R^4$ and $R^5$ independently is $C_{1-6}$ alkyl;
$X^-$ is a pharmaceutically acceptable counter ion;
n and m are each independently 1, or 2,
$R^2$ is an aryl or an heteroaryl group selected from

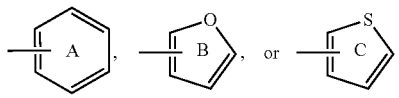

wherein each of rings A-O is optionally and independently substituted with one or more substituents selected from the group consisting of halogen, $Ak^1$, $Ar^1$, —$NO_2$, —CN, —NCS, —C(O)$OR^{10}$, —C(O)$R^{10}$, —C(S)$R^{10}$, —OC(O)$R^{10}$, —C(O)N($R^{11}$)$_2$, —C(S)N($R^{11}$)$_2$, —S(O)$R^{12}$, —S(O)$_2R^{12}$, —$SO_2$N($R^{11}$)$_2$, —$SO_2$N($R^{11}$)—$NR^{11}$, —$OR^{10}$, —$SR^{10}$, —N($R^{11}$)$_2$, —$NR^{11}$C(O)$R^{10}$, —$NR^{11}$S(O)$R^{12}$, —$NR^{11}$C(O)$OR^{12}$, —$NR^{11}$C(O)N($R^{11}$)$_2$, —$NR^{11}SO_2$N($R^{11}$)$_2$, —$NR^{11}SO_2R^{12}$, —O—[$CH_2$]$_p$—O—, —S—[$CH_2$]$_p$—S— and —[$CH_2$]$_q$—; or wherein:
$Ak^1$ is a $C_{1-20}$ aliphatic group
each $R^{10}$ independently is
a $C_{1-20}$ aliphatic group;
each $R^{11}$ independently is $R^{10}$, —$CO_2R^{10}$, —$SO_2R^{10}$ or —C(O)$R^{10}$, or —N($R^{11}$)$_2$ taken together is an optionally substituted non-aromatic heterocyclic group; and
each $R^{12}$ independently is
a $C_{1-20}$ aliphatic group;
$Ar^1$ is a $C_{6-14}$ aryl or a 5-14 membered heteroaryl group;
each p independently is 1, 2, 3 or 4;
each q independently is 3, 4, 5 or 6;
each $R^3$ independently is an unsubstituted $C_1$-$C_{10}$ alkyl group.

2. The compound of claim 1, wherein each of $R^4$ and $R^5$ independently is —$CH_3$.

3. The compound of claim 1, wherein Q is —C(=O)—, or —C(O)NH—.

4. The compound of claim 3, represented by a structural formula selected from the group consisting of:

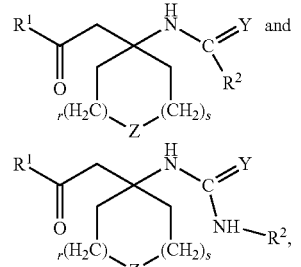

or a pharmaceutically acceptable salt thereof, wherein:
each Y is O; and
each of r and s independently is 0, 1 or 2, provided that the sum of r and s is 1 or 2.

5. A compound represented by a structural formula selected from the group consisting of:

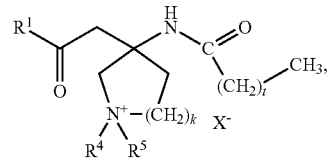

-continued

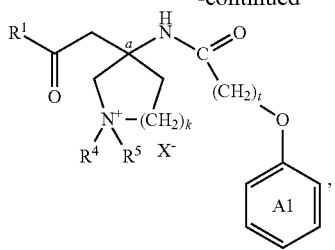

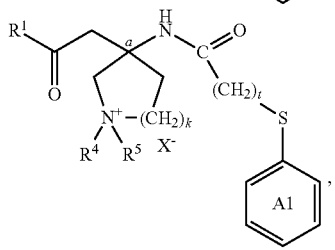

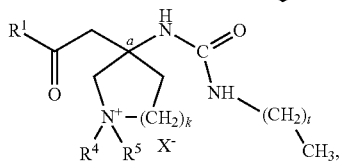

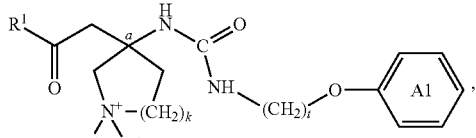

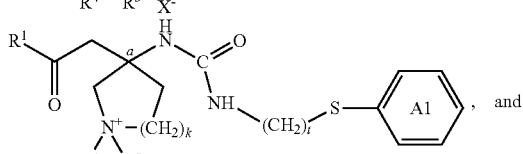, and

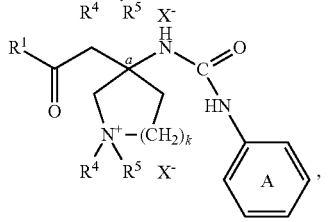

or a pharmaceutically acceptable salt thereof, wherein:
each t is 1, 2, 3, 4, 5, 6, 7, 8, 9, or 10;
each k is 1 or 2;
each ring A1 is optionally substituted with one or more substituents selected from the group consisting of: halogen, $C_{1-6}$ alkyl, $C_{1-6}$ haloalkyl, —O—$C_{1-10}$ alkyl and ($C_{1-6}$ alkoxy) $C_{1-6}$ alkyl;
each ring A is optionally substituted with one or more substituents selected from the group consisting of halogen, $C_{1-15}$ alkyl; $C_{1-15}$ haloalkyl; —$C_{2-10}$ alkynylene-($C_{1-10}$ alkyl); —$C_{2-10}$ alkynyl, —$C_{1-10}$ alkylene-N($R^{21}$)$_2$, —$C_{1-10}$ alkylene-O—$C_{1-5}$ alkyl; —$C_{1-10}$ alkylene-S—$C_{1-5}$ alkyl, —O$C_{1-10}$ alkyl, and —S$C_{1-10}$ alkyl;

$R^1$ is —OH or —O$C_{1-6}$ alkyl; and
each of $R^4$ and $R^5$ independently is —CH$_3$.

6. The compound of claim 1, represented by the following structural formula:

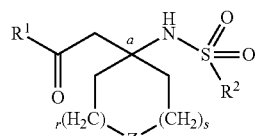

or a pharmaceutically acceptable salt thereof, wherein each of r and s independently is 0, 1 or 2, provided that the sum of r and s is 1 or 2.

7. A compound represented by a structural formula selected from the group consisting of:

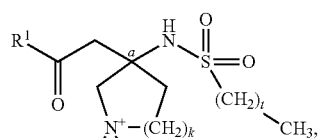

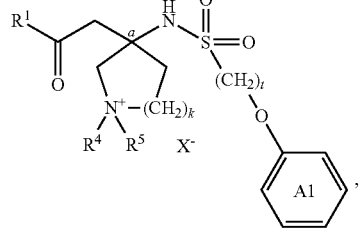

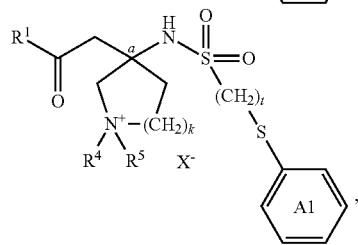, and

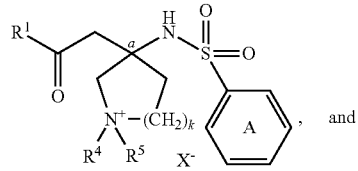

or a pharmaceutically acceptable salt thereof, wherein:
each t is 1, 2, 3, 4, 5, 6, 7, 8, 9 or 10;
each k is 1 or 2; and
each ring A1 is optionally substituted with one or more substituents selected from the group consisting of: halogen, $C_{1-6}$ alkyl, $C_{1-6}$ haloalkyl, —O—$C_{1-10}$ alkyl and ($C_{1-6}$ alkoxy) $C_{1-6}$ alkyl;
each ring A is optionally substituted with one or more substituents selected from the group consisting of halogen, $C_{1-15}$ alkyl; $C_{1-15}$ haloalkyl; —$C_{2-10}$ alkynylene-($C_{1-10}$ alkyl); —$C_{2-10}$ alkynyl, —$C_{1-10}$ alkylene-N($R^{21}$)$_2$, —$C_{1-10}$ alkylene-O—$C_{1-5}$ alkyl; —$C_{1-10}$ alkylene-S—$C_{1-5}$ alkyl, —O$C_{1-10}$ alkyl, and —S$C_{1-10}$ alkyl;

$R^1$ is —OH or —$OC_{1-6}$ alkyl; and each of $R^4$ and $R^5$ independently is —$CH_3$.

8. The compound of claim 1, wherein the compound is represented by a structural formula selected from the group consisting of:

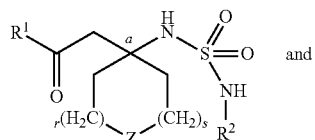

and

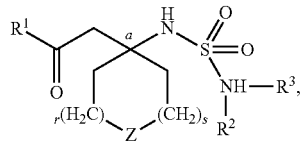

or a pharmaceutically acceptable salt thereof, wherein:
each of r and s independently is 0, 1 or 2, provided that the sum of r and s is 1 or 2.

9. A compound represented by a structural formula selected from the group consisting of:

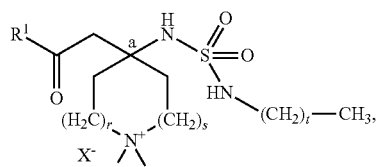

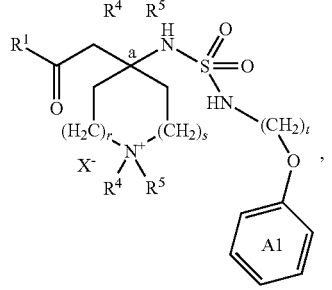

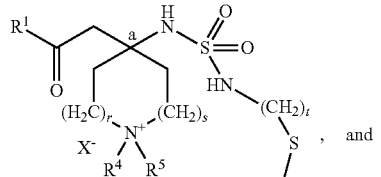

and

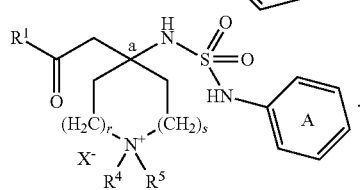

or a pharmaceutically acceptable salt thereof, wherein:
each t is 1, 2, 3, 4, 5, 6, 7, 8, 9 or 10;
each ring A1 is optionally substituted with one or more substituents selected from the group consisting of: halogen, $C_{1-6}$ alkyl, $C_{1-6}$ haloalkyl, —O—$C_{1-10}$ alkyl and ($C_{1-6}$ alkoxy) $C_{1-6}$ alkyl;

each ring A is optionally substituted with one or more substituents selected from the group consisting of halogen, $C_{1-15}$ alkyl; $C_{1-15}$ haloalkyl; —$C_{2-10}$ alkynylene-($C_{1-10}$ alkyl); —$C_{2-10}$ alkynyl, —$C_{1-10}$ alkylene-N($R^{21}$)$_2$, —$C_{1-10}$ alkylene-O—$C_{1-5}$ alkyl; —$C_{1-10}$ alkylene-S—$C_{1-5}$ alkyl, —$OC_{1-10}$ alkyl, and —$SC_{1-10}$ alkyl;

$R^1$ is —OH or —$OC_{1-6}$ alkyl; and each of $R^4$ and $R^5$ is —$CH_3$.

10. A compound represented by a structural formula selected from the group consisting of:

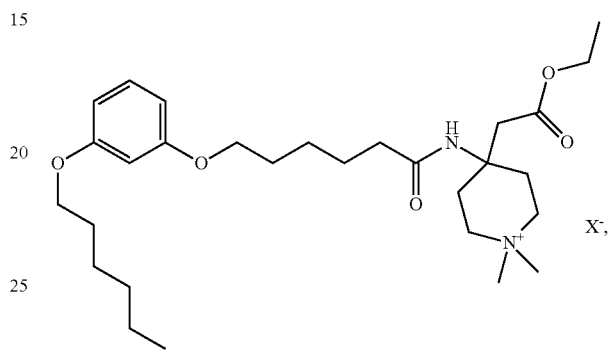

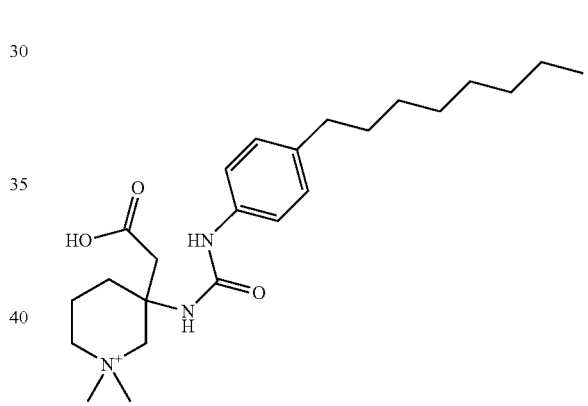

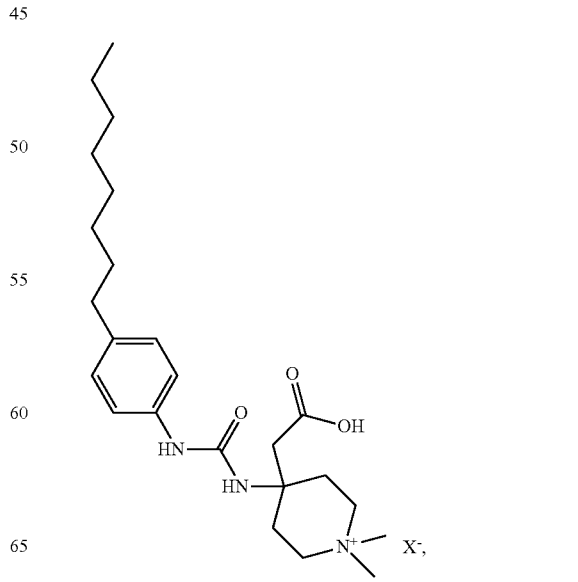

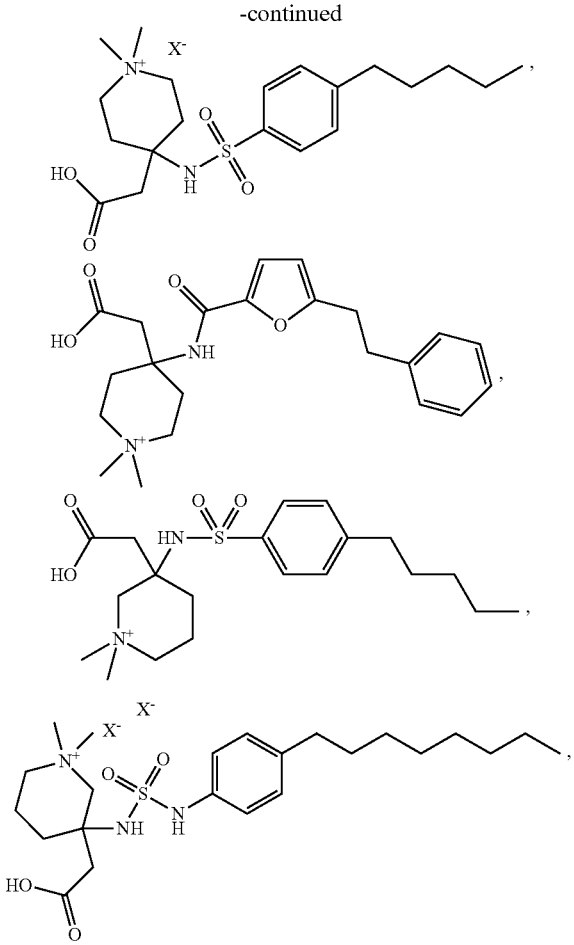
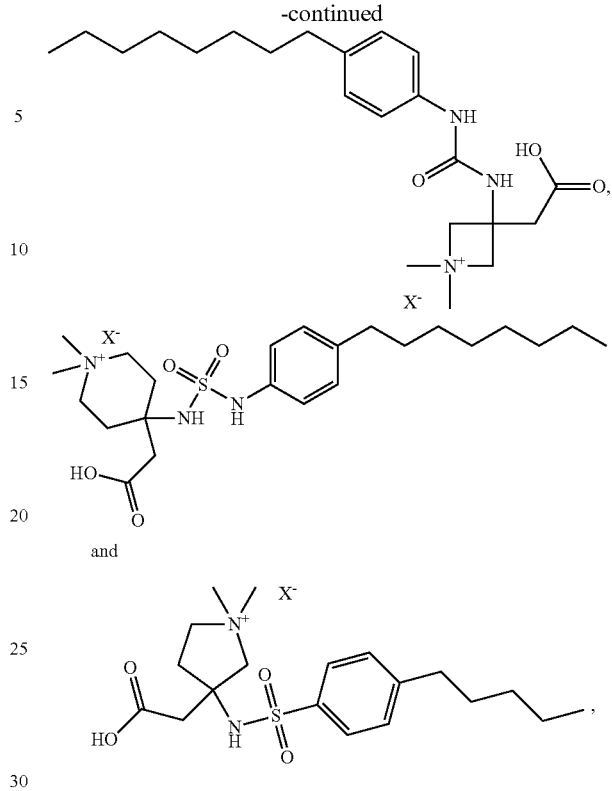
or a pharmaceutically acceptable salt thereof, wherein $X^-$ is a pharmaceutically acceptable counter ion.
11. A pharmaceutical composition, comprising a pharmaceutically acceptable carrier, and the compound of claim 1.
* * * * *

UNITED STATES PATENT AND TRADEMARK OFFICE
CERTIFICATE OF CORRECTION

PATENT NO. : 8,680,282 B2  Page 1 of 1
APPLICATION NO. : 12/671154
DATED : March 25, 2014
INVENTOR(S) : Heinz W. Pauls et al.

It is certified that error appears in the above-identified patent and that said Letters Patent is hereby corrected as shown below:

In the Claims:

At column 83, claim number 1, line number 58, replace "A-O" with -- A-C --;

At column 83, claim number 1, line number 63, add $-SO_3R^{12}$ after $-S(O)_2R^{12}$.

Signed and Sealed this
Eleventh Day of November, 2014

Michelle K. Lee
*Deputy Director of the United States Patent and Trademark Office*